US006881548B2

(12) United States Patent
Serrero

(10) Patent No.: US 6,881,548 B2
(45) Date of Patent: Apr. 19, 2005

(54) METHODS AND KITS FOR DIAGNOSING TUMORIGENICITY AND DETERMINING RESISTANCE TO THE ANTINEOPLASTIC EFFECTS OF ANTIESTROGEN THERAPY

(75) Inventor: Ginette Serrero, Baltimore, MD (US)

(73) Assignee: A&G Pharmaceutical, Inc., Columbia, MD (US)

( * ) Notice: Subject to any disclaimer, the term of this patent is extended or adjusted under 35 U.S.C. 154(b) by 0 days.

(21) Appl. No.: 09/880,842

(22) Filed: Jun. 15, 2001

(65) Prior Publication Data
US 2002/0025543 A1 Feb. 28, 2002

Related U.S. Application Data

(60) Continuation-in-part of application No. 09/456,886, filed on Dec. 8, 1999, now Pat. No. 6,720,159, which is a division of application No. 08/863,079, filed on May 23, 1997, now abandoned.

(51) Int. Cl.[7] .................. G01N 33/543; G01N 33/577; G01N 33/53
(52) U.S. Cl. ...................... 435/7.23; 435/7.1; 436/501; 436/518
(58) Field of Search ............................... 436/501, 518; 530/350; 438/7.1; 435/7.23

(56) References Cited

U.S. PATENT DOCUMENTS

| 6,309,826 B1 | 10/2001 | Serrero |
| 6,511,986 B1 | 1/2003 | Zhang et al. |

FOREIGN PATENT DOCUMENTS

| WO | WO 91 15510 A | 10/1991 |
| WO | WO 91/15510 | * 10/1991 |

OTHER PUBLICATIONS

Tockman et al (Cancer Res., 1992, 52:2711s–2718s).*
*Effect of Testosterone on the Growth Properties and on Epidermal Growth Factor Receptor Expression in the Teratoma–derived Tumorogenic Cell Line 1246–3A*, Serrero, G. et al., Cancer Research 52, 1992, pp. 4242–4247.
*Molecular Biology of the Cell*, Alberts, B., et al., Garland Publishing, Inc., 1983.
*Growth Factors in Development, Transformation, and Tumorigenesis*, Cross, M. et al., Cell, vol. 64, 1991, pp. 271–280.
*Autocrine Secretion and Malignant Transformation of Cells*, Sporn, M.B. et al., The New England Journal of Medicine, vol. 303, 1980, pp. 878–880.
*Purification of an Autocrine Growth Factor Homologous with Mouse Epithelin Precursor from a Highly Tumorigenic Cell Line*; Zhou, J. et al., The Journal of Biological Chemistry, vol. 268, No. 15, 1993, pp. 10863–10869.
*The Epithelin Precursor Encodes Two Proteins with Opposing Activities on Epithelial Cell Growth*, Plowman, G. et al., The Journal of Biological Chemistry, vol. 267, No. 18, 1992, pp. 13073–13078.
*Granulins, a Novel Class of Peptide from Leukocytes*, Bateman, A. et al., Biochemical and Biophysical Research Communications, vol. 173, No. 3, 1990, pp. 1161–1168.
*A Synthetic Fragment of Rat Transforming Growth Factor with Receptor Binding and Antigenic Properties*, Nestor, J. et al., Biochemical and Biophysical Research Communications, vol. 129, No. 1, 1985, pp. 226–232.
*In Vitro Deletional Mutagenesis for Bacterial Production of the 20,000–Dalton Form of Human Pituitary Growth Hormone*, Adelman, J. et al., DNA, vol. 2, No. 3, 1983, pp. 183–193.
*An In Vitro Model to Study Adipose Differentiation in Serum–Free Medium*, Serrero, G. et al., Analytical Biochemistry 120, 1982, pp. 351–359.
*Study of a Teratoma–Derived Adipogenic Cell Line 1246 and Isolation of an Insulin–Independent Variant in Serum–Free Medium*, Serrero–Dave, G., Cancer Center, University of California, pp. 366–376.
*Tumorigenicity Associated with Loss of Differentiation and of Response to Insulin in the Adipogenic Cell Line 1246*, Serrero, G., In Vitro Cellular & Developmental Biology, vol. 21, No. 9, 1985, pp. 537–540.
*Decreased Transformaing Growth Factor–β Response and Binding in Insulin–Independent Teratoma–Derived Cell Lines with Increased Tumorigenic Properties*, Serrero, G. et al., Journal of Cellular Physiology, 149, 1991, pp 503–511.
*Growth Inhibition of Human Breast Cancer Cells in Vitro with an Antibody against the Type I Somatomedin Receptor*, Arteaga, C. et al., Cancer Research 49, 1989, pp. 6237–6241.
*The Biological Effects of a High Molecular Weight Form of IFG II in a Pluripotential Human Teratocarcinoma Cell Line*, Schofield, P. et al., Anticancer Research 14, 1994, pp. 533–538.
*Gene therapy of murine teratocarcinoma: Separate functions for insulin–like growth factors I and II in immunogenicity and differentiation*, Trojan, J. et al., Proc. Natl. Acad. Sci. USA, vol. 91, 1994, pp. 6088–6092.

(Continued)

Primary Examiner—Larry R. Helms
Assistant Examiner—Misook Yu
(74) Attorney, Agent, or Firm—Dickstein Shapiro Morin & Oshinsky LLP

(57) ABSTRACT

Methods and kits for diagnosing tumorigenicity and for determining whether a cancer patient is resistant to the pharmacological effects of antiestrogen therapy. Increased levels of the PCDGF (GP88) growth factor are indicative of tumorigenicity and resistance to the pharmacological effects of antiestrogen therapy. The methods and kits of the invention are useful for assessing the tumorigencity of a biological sample from a patient and determining whether the patient is a candidate for antiestrogen, including tamoxifen, therapy.

35 Claims, 30 Drawing Sheets

OTHER PUBLICATIONS

*Treatment and Prevention of Rat Glioblastoma by Immunogenic C6 Cells Expressing Antisense Insulin–Like Growth Factor I RNA*, Trojan, J. et al., Science, vol. 259, 1993, pp. 94–96.

*Continuous cultures of fused cells secreting antibody of predifined specificity*, Kohler, G. et al., Nature, vol. 256, 1975, pp. 495–497.

*Production of Monoclonal Antibodies: Strategy and Tactics*, de St. Groth, S.F. et al., Journal of Immunology Methods, 35, 1980, pp. 1–21.

*Hybridoma Techniques*, Schreier, M. et al., Cold Spring Harbor Laboratory, 1980.

*Generation of antibody activity from immunoglobulin polypeptide chains produced in Escherichia coli*, Cabilly, S. et al., Proc. Natl. Acad. Sci. USA, vol. 81, 1984, pp. 3273–3277.

*Chimeric human antibody molecules: Mouse antigen–binding domains with human constant region domains*, Morrison, S. et al., Proc. Natl. Acad. Sci. USA, vol. 81, 1984, pp. 6851–6855.

*Chimeric mouse–human IgG1 antibody that can mediate lysis of cancer cells*, Liu, A. et al., Proc. Natl. Acad. Sci. USA, vol. 84, 1987, pp. 3439–3443.

*Escherichia coli Secretion of an Active Chimeric Antibody Fragment*, Better, M. et al., Science, vol. 240, 1988, pp. 1041–1043.

*Reshaping human antibodies for therapy*, Riechmann, L. et al., Nature, vol. 332, 1988, pp. 323–327.

*Antibody Humanization Using Monovalent Phage Display*, Baca, M. et al., J. Biol. Chem., vol. 272, No. 16, 1997, pp. 10678–10684.

*A Combinatorial Library Strategy for the Rapid Humanization of Anticarcinoma BR96 Fab*, Rosok, M.J. et al., J. Biol. Chem., vol. 271, No. 37, 1996, pp. 22611–22618.

*Improved Radioimaging and Tumor Localization with Monoclonal F(ab')$_2$*, Wahl, R.L. et al., The Journal of Nuclear Medicine, vol. 24, No. 4, 1983, pp. 316–325.

*Clinical Use of a Monoclonal Antibody to Bombesin–like Peptide in Patients with Lung Cancer*, Mulshine, J.L., Annals New York Academy of Sciences, pp. 360–372.

*Antisense RNA inhibits splicing of pre–mRNA in vitro*, Munroe, S.H., The EMBO Journal, vol. 7, No. 8, 1988, pp. 2523–2532.

*Specific Synthesis of DNA in Vitro via a Polymerase–Catalyzed Chain Reaction*, Mulis, K.B. et al., Methods in Enzymology, vol. 155, 1987, pp. 335–350.

*Antisense approaches to cancer gene therapy*, Mercola, D. et al., Cancer Gene Therapy, vol. 2, No. 1, 1995, pp. 47–59.,

*Gene inhibition using antisense oligodeoxynucleotides*, Wagner, R. W., Nature, vol. 372, 1994, pp. 333–335.

*Molecular Cloning: A Laboratory Manual*, Maniatis, T. et al., Cold Spring Harbor Laboratory, 1982.

*Design and Application of Antisense Oligonucleotides in Cell Culture, in Vivo, and as Therapeutic Agents*, Brysch, W. et al., Cellular and Molecular Neurobiology, vol. 14, No. 5, 1994, pp. 557–568.

*Rational Design of Sequence–specific Oncogene Inhibitors Based on Antisense and Antigene Oligonucleotides*, Helene, C., Eur. J. Cancer, vol. 27, No. 11, 1991, pp. 1466–1471.

*Optimization of Antisense Oligodeoxynucleotide Structure for Targeting bcr–abl mRNA*, Giles, R.V. et al., Blood, vol. 86, No. 2, 1995, pp. 744–754.

*Extending the chemistry that supports genetic information transfer in vivo: Phosphorothioate DNA, phosphorothioate RNA, 2'–O–methyl RNA, and methylphosphonate DNA*, Thaler, D.S. et al., Proc. Natl. Acad. Sci. USA, vol. 93, 1996, pp. 1352–1356.

*Oligonucleotide N3'–P5' phosphoroamidates as antisense agents*, Gryaznov, S. et al., Nucleic Acids Research, vol. 24, No. 8, 1996, pp. 1508–1514.

*Cationic liposomes improve stability and intracellular delivery of antisense oligonucleotides into CaSki cells*, Lappalainen, K. et al., Biochimica et Biophysica Acta 1196, 1994, pp. 201–208.

*Block of AIDS–Kaposi's Sarcoma (KS) Cell Growth, Angiogenesis, and Lesion Formation in Nuce Mice by Antisense Oligonucleotide Targeting Basic Fibroblast Growth Factor*, Ensoli, B. et al., The Journal of Clinical Investigation, Inc., vol. 94, 1994, pp. 1736–1746.

*Growth Inhibition of Malignant CD5$^+$B (B–1) Cells by Antisense IL–10 Oligonucleotide*, Peng, B. et al., Leukemia Research, vol. 19, No. 3, 1995, pp. 159–167.

*Review: Optimizing inducer and culture conditions for expression of foreign proteins under the control of the lac promoter*, Donovan, R.S. et al., Journal of Industrial Microbiology, 16, 1996, pp. 145–154.

*Prokaryotic gene expression in vitro: Transcription–translation coupled systems*, Cenatiempo, Y., Biochimie, 68, 1986, pp. 505–515.

*Bacterial Regulation: Global Regulatory Networks*, Gottesman, S., Ann, Rev. Genet., 18, 1984, pp. 415–441.

*Regulation In Vivo of a Cloned Mammalian Gene: Cadmium Induces the Transcription of a Mouse Metallothionein Gene in SV40 Vectors*, Hamer, D.H. et al., Journal of Molecular and Applied Genetics, vol. 1, No. 4, 1982, pp. 273–288.

*Functional Relationships between Transcriptional Control Signals of the Thymidine Kinase Gene of Herpes Simplex Virus*, McKnight, S.L., Cell, vol. 31, 1982, pp. 355–365.

*Isolation of the yeast regulatory gene GAL4 and analysis of its dosage effects on the galactose/melibiose regulon*, Johnston, S.A. et al., Proc. Natl. Acad. Sci. USA, 79, 1982, pp. 6971–6975.

*In vivo sequence requirements of the SV40 early promoter region*, Benoist, C. et al., Nature, vol. 290, 1981, pp. 304–310.

*Cloning, Structure, and Expression of the Mitochondrial Cytochrome P–450 Sterol 26–Hydroxylase, a Bile Acid Biosynthetic Enzyme*, Andersson, S. et al., The Journal of Biological Chemistry, vol. 264, No. 14, 1989, pp. 8222–8229.

*Insulin and Insulin–like Growth Factor Signaling Are Defective in the MDA MB–468 Human Breast Cancer Cell Line*, Sepp–Lorenzino, L. et al., Cell Growth & Differentiation, vol. 5, 1994, pp. 1077–1083.

*Biochemical Analysis of the Epithelin Receptor*, Culouscou, J.M. et al., The Journal of Biological Chemistry, vol. 268, No. 14, 1993, pp. 10458–10462.

*Targeted Toxins as Anticancer Agents*, Siegall, C.B., Cancer, Vol. 74, No. 3, 1994, pp. 1006–1012.

*Mediation of estrogen mitogenic effect in human breast cancer MCF–7 cells by PC–cell–derived growth factor (PCDGF/granulin precursor)*, Lu, Runging, et al., PNAS, Jan. 2, 2001, vol. 98, No. 1, pp. 142–147.

Zhang Haidi, "Overexpression of PC cell derived growth factor (PCDGF) contributes to the highly tumorigenic properties of producer cell line PC," Diss. Abstr. Int., vol. 58, No. 11, 1998, p. 5814–B XP001025915, abstract.

Vijay Bandhari and Andrew Bateman, "Structure and Chromosomal Location of the human granulin gene," Biochemical and Biophysical Research Communications, vol. 188, No. 1, 1992, pp. 57–63, XP001018991, abstract, figure 2.

Bhandari et al., "The Complementary Deoxyribonucleic Acid Sequence, Tissue Distribution, and Cellular Localization of the Rat Granulin Precursor," Endocrinology, vol. 133, No. 6, 1993, pp. 2682–2689, XP001021601.

Haidi Zhang and Ginette Serrero, "Inhibition of tumorigenicity of the teratoma PC cell line by transfection with antisense cDNA for PC cell–derived growth factor (PCDGF, epithelin/granulin precursor)," PNAS, vol. 95, Nov. 1998 (1998–11), pp. 14202–14207, XP002177206.

European Search Report dated Oct. 23, 2001.

Zhang, Haidi—"Overexpression of PC Cell Derived Growth Factor (PCDGF) Contributes To The Highly Tumorogenic Properties Of Producer Cell Line PC" a Dissertation submitted in partial fulfillment of the requirements for the degree of Doctor of Philosophy, Chemistry, Fall of 1997, 143 pages, Clarkson University.

Vijay Bhandari, et al.—"Isolation and sequence of the granulin precursor cDNA from human bone marrow reveals tandem cysteine–rich granulin domans," Proc. Natl. Acad. Sci. USA, vol. 89, Mar. 1992, pp. 1715–1719.

Runging Lue, et al.—"Inhibition of PC cell–derived growth factor (PCDGF, epithelin/granulin precursor) expression by antisense PCDGF cDNA transfection inhibits tumorigenicity of the human breast carcinoma cell line MDA–MB–468," PNAS, vol. 97, No. 8, Apr. 11, 2000, pp. 3993–3998.

Zhiheng He, et al.—"Progranulin Gene Expression Regulates Epthelial Cell Growth and Promotes Tumor Growth in Vivo[1]," Cancer Research 59, Jul. 1, 1999, pp. 3222–3229.

International Search Report dated May 13, 2003.

* cited by examiner

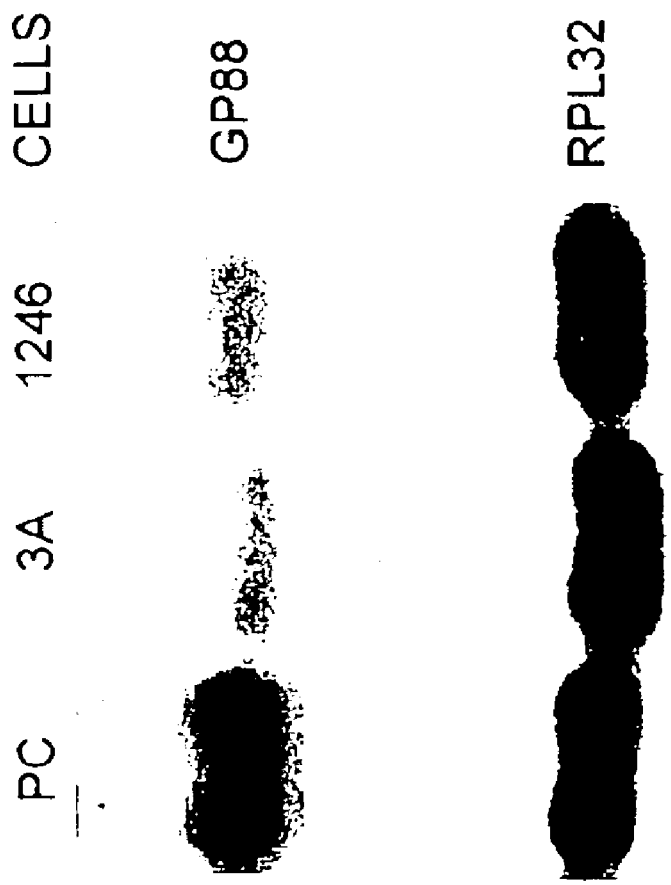

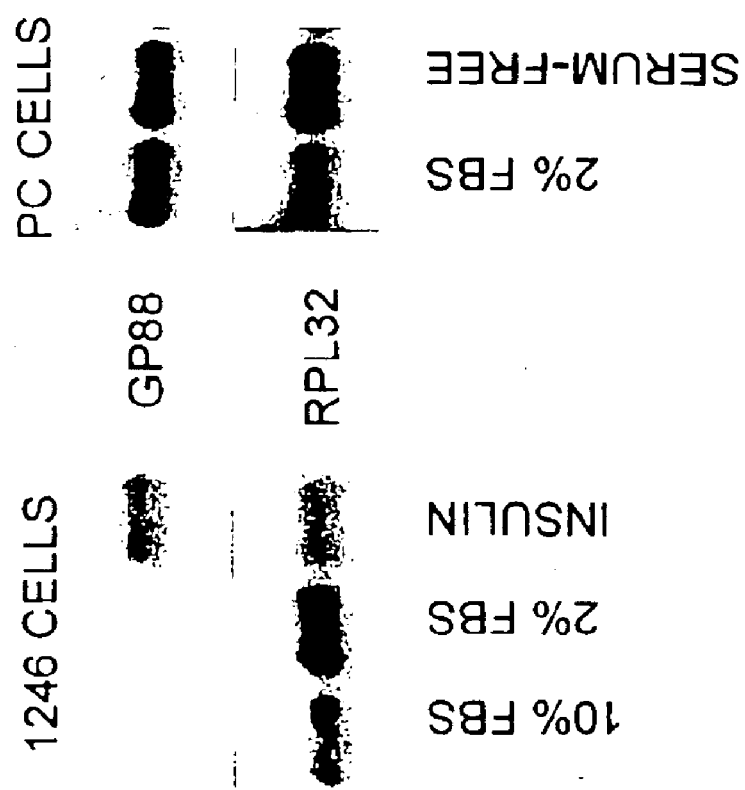

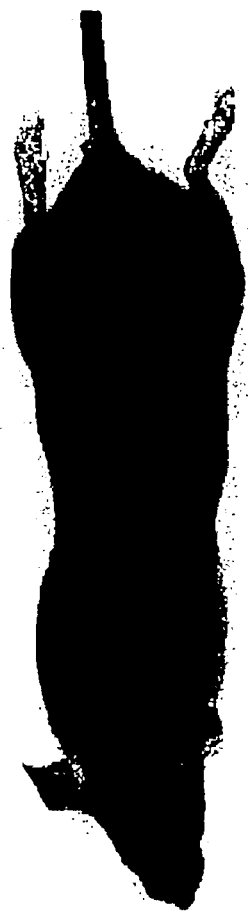
ABSENCE OF TUMOR FORMATION IN C3H MICE BY INHIBITION OF GP88 EXPRESSION
GP88 ANTISENSE TRANSFECTED PC CELLS
CONTROL TRANSFECTED PC CELLS
FIG. 3

FIG. 5 GP88 mRNA EXPRESSION IN ESTROGEN-DEPENDENT AND INDEPENDENT HUMAN MAMMARY CARCINOMA CELLS Mouse GP88 cDNA

```
 C GGA CCC CGA CGC AGA CAG ACC ATG TGG GTC CTG ATG AGC TGG CTG    46
                                 M   W   V   L   M   S   W   L     8

GCC TTC GCG GCA GGG CTG GTA GCC GGA ACA CAG TGT CCA GAT GGG CAG    94
 A   F   A   A   G   L   V   A   G   T   Q   C   P   D   G   Q    24

TTC TGC CCT GTT GCC TGC TGC CTT GAC CAG GGA GGA GCC AAC TAC AGC   142
 F   C   P   V   A   C   C   L   D   Q   G   G   A   N   Y   S    40

TGC TGT AAC CCT CTT CTG GAC ACA TGG CCT AGA ATA ACG AGC CAT CAT   190
 C   C   N   P   L   L   D   T   W   P   R   I   T   S   H   H    56

CTA GAT GGC TCC TGC CAG ACC CAT GGC CAC TGT CCT GCT GGC TAT TCT   238
 L   D   G   S   C   Q   T   H   G   H   C   P   A   G   Y   S    72

TGT CTT CTC ACT GTG TCT GGG ACT TCC AGC TGC TGC CCG TTC TCT AAG   286
 C   L   L   T   V   S   G   T   S   S   C   C   P   F   S   K    88

GGT GTG TCT TGT GGT GAT GGC TAC CAC TGC TGC CCC CAG GGC TTC CAC   334
 G   V   S   C   G   D   G   Y   H   C   C   P   Q   G   F   H   104

TGT AGT GCA GAT GGG AAA TCC TGC TTC CAG ATG TCA GAT AAC CCC TTG   382
 C   S   A   D   G   K   S   C   F   Q   M   S   D   N   P   L   120

GGT GCT GTC CAG TGT CCT GGG AGC CAG TTT GAA TGT CCT GAC TCT GCC   430
 G   A   V   Q   C   P   G   S   Q   F   E   C   P   D   S   A   136

ACC TGC TGC ATT ATG GTT GAT GGT TCG TGG GGA TGT TGT CCC ATG CCC   478
 T   C   C   I   M   V   D   G   S   W   G   C   C   P   M   P   152

CAG GCC TCT TGC TGT GAA GAC AGA GTG CAT TGC TGT CCC CAT GGG GCC   526
 Q   A   S   C   C   E   D   R   V   H   C   C   P   H   G   A   168

TCC TGT GAC CTG GTT CAC ACA CGA TGC GTT TCA CCC ACG GGC ACC CAC   574
 S   C   D   L   V   H   T   R   C   V   S   P   T   G   T   H   184

ACC CTA CTA AAG AAG TTC CCT GCA CAA AAG ACC AAC AGG GCA GTG TCT   622
 T   L   L   K   K   F   P   A   Q   K   T   N   R   A   V   S   200

TTG CCT TTT TCT GTC GTG TGC CCT GAT GCT AAG ACC CAG TGT CCC GAT   670
 L   P   F   S   V   V   C   P   D   A   K   T   Q   C   P   D   216
```

FIG.8A

Mouse GP88 cDNA (continued)

```
GAT TCT ACC TGC TGT GAG CTA CCC ACT GGG AAG TAT GGC TGC TGT CCA    718
 D   S   T   C   C   E   L   P   T   G   K   Y   G   C   C   P    232

ATG CCC AAT GCC ATC TGC TGT TCC GAC CAC CTG CAC TGC TGC CCC CAG    766
 M   P   N   A   I   C   C   S   D   H   L   H   C   C   P   Q    248

GAC ACT GTA TGT GAC CTG ATC CAG AGT AAG TGC CTA TCC AAG AAC TAC    814
 D   T   V   C   D   L   I   Q   S   K   C   L   S   K   N   Y    264

ACC ACG GAT CTC CTG ACC AAG CTG CCT GGA TAC CCA GTG AAG GAG GTG    862
 T   T   D   L   L   T   K   L   P   G   Y   P   V   K   E   V    280

AAG TGC GAC ATG GAG GTG AGC TGC CCT GAA GGA TAT ACC TGC TGC CGC    910
 K   C   D   M   E   V   S   C   P   E   G   Y   T   C   C   R    296

CTC AAC ACT GGG GCC TGG GGC TGC TGT CCA TTT GCC AAG GCC GTG TGT    958
 L   N   T   G   A   W   G   C   C   P   F   A   K   A   V   C    312

TGT GAG GAT CAC ATT CAT TGC TGC CCG GCA GGG TTT CAG TGT CAC ACA   1006
 C   E   D   H   I   H   C   C   P   A   G   F   Q   C   H   T    328

GAG AAA GGA ACC TGC GAA ATG GGT ATC CTC CAA GTA CCC TGG ATG AAG   1054
 E   K   G   T   C   E   X   G   I   L   Q   V   P   W   M   K    344

AAG GTC ATA GCC CCC CTC CGC CTG CCA GAC CCA CAG ATC TTG AAG AGT   1102
 K   V   I   A   P   L   R   L   P   D   P   Q   I   L   K   S    360

GAT ACA CCT TGT GAT GAC TTC ACT AGG TGT CCT ACA AAC AAT ACC TGC   1150
 D   T   P   C   D   D   F   T   R   C   P   T   N   N   T   C    376

TGC AAA CTC AAT TCT GGG GAC TGG GGC TGC TGT CCC ATC CCA GAG GCT   1198
 C   K   L   N   S   G   D   W   G   C   C   P   I   P   E   A    392

GTC TGC TGC TCA GAC AAC CAG CAT TGC TGC CCT CAG GGC TTC ACA TGT   1246
 V   C   C   S   D   N   Q   H   C   C   P   Q   G   F   T   C    408

CTG GCT CAG GGG TAC TGT CAG AAG GGA GAC ACA ATG GTG GCT GGC CTG   1294
 L   A   Q   G   Y   C   Q   K   G   D   T   M   V   A   G   L    424

GAG AAG ATA CCT GCC CGC CAG ACA ACC CCG CTC CAA ATT GGA GAT ATC   1342
 E   K   I   P   A   R   Q   T   T   P   L   Q   I   G   D   I    440
```

FIG.8B

Mouse GP88 cDNA (continued)

```
GGT TGT GAC CAG CAT ACC AGC TGC CCA GTA GGG CAA ACC TGC TGC CCA    1390
 G   C   D   Q   H   T   S   C   P   V   G   Q   T   C   C   P     456

AGC CTC AAG GGA AGT TGG GCC TGC TGC CAG CTG CCC CAT GCT GTG TGC    1438
 S   L   K   G   S   W   A   C   C   Q   L   P   H   A   V   C     472

TGT GAG GAC CGG CAG CAC TGT TGC CCG GCC GGG TAC ACC TGC AAC GTG    1486
 C   E   D   R   Q   H   C   C   P   A   G   Y   T   C   N   V     488

AAG GCG AGG ACC TGT GAG AAG GAT GTC GAT TTT ATC CAG CCT CCC GTG    1534
 K   A   R   T   C   E   K   D   V   D   F   I   Q   P   P   V     504

CTC CTG ACC CTC GGC CCT AAG GTT GGG AAT GTG GAG TGT GGA GAA GGG    1582
 L   L   T   L   G   P   K   V   G   N   V   E   C   G   E   G     520

CAT TTC TGC CAT GAT AAC CAG ACC TGT TGT AAA GAC AGT GCA GGA GTC    1630
 H   F   C   H   D   N   Q   T   C   C   K   D   S   A   G   V     536

TGG GCC TGC TGT CCC TAC CTA AAG GGT GTC TGC TGT AGA GAT GGA CGT    1678
 W   A   C   C   P   Y   L   K   G   V   C   C   R   D   G   R     552

CAC TGT TGC CCC GGT GGC TTC CAC TGT TCA GCC AGG GGA ACC AAG TGT    1726
 H   C   C   P   G   G   F   H   C   S   A   R   G   T   K   C     568

TTG CGA AAG AAG ATT CCT CGC TGG GAC ATG TTT TTG AGG GAT CCG GTC    1774
 L   R   K   K   I   P   R   W   D   M   F   L   R   D   P   V     584

CCA ACA CCG CTA CTG TAA GGA AGG GCT ACA GAC TTA AGG AAC TCC ACA    1822
 P   T   P   L   L   *                                              589

GTC CTG GGA ACC CTG TTC CGA GGG TAC CCA CTA CTC AGG CCT CCC TAG    1870
CGC CTC CTC CCC TAA CGT CTC CCC GGC CTA CTC ATC CTG AGT CAC CCT    1918
ATC ACC ATG GGA GGT GGA GCC TCA AAC TAA AAC CTT CTT TTA TGG AAA    1966
GAA GGC TGT GGC CAA AAG CCC CGT ATC AAA CTG CCA TTT CTT CCG GTT    2014
TCT GTG GAC CTT GTG GCC AGG TGC TCT TCC CGA GCC ACA GGT GTT CTG    2062
TGA GCT TGC TTG TGT GTG TGT GCG CGT GTG CGT GTG TTG CTC CAA TAA    2110
AGT TTG TAC GCT TTC TGA AAA AAA AAA                                2137
```

FIG.8C

Nucleotide sequence of human granulin/epithelin precursor (human GP88).
Human Granulin Genbank M75161$

```
cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgcccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgttatggt cgatggctcc tgggggtgct gccccatgcc ccaggcttcc
tgctgtgaag acagggtgca ctgctgtccg cacggtgcct tctgcgacct ggttcacacc
cgctgcatca cacccacggg cacccacccc ctggcaaaga agctccctgc cagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctataccctgc
tgccgtctac agtcgggggc ctggggctgc tgccctttta cccaggctgt gtgctgtgag
gaccacatac actgctgtcc gcggggttt acgtgtgaca cgcagaaggg tacctgtgaa
caggggcccc accaggtgcc ctggatggag aaggccccag ctcacctcag cctgccagac
ccacaagcct tgaagagaga tgtcccctgt gataatgtca gcagctgtcc ctcctccgat
acctgctgcc aactcacgtc tggggagtgg gctgctgtc aatcccaga ggctgtctgc
tgctcggacc accagcactg ctgcccccag cgatacacgt gtgtagctga ggggcagtgt
cagcgaggaa gcgagatcgt ggctggactg gagaagatgc ctgcccgccg cggttcctta
tcccaccccca gagacatcgg ctgtgaccag cacaccagct gcccggtggg cggaacctgc
tgcccgagcc agggtgggag ctgggcctgc tgccagttgc ccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata accagacctg ctgccgagac
aaccgacagg gctgggcctg ctgtcctac gcccagggcg tctgttgtgc tgatcggcgc
cactgctgtc ctgctggctt ccgctgcgca cgcagggta ccaagtgttt gcgcagggag
gccccgcgct gggacgcccc tttgagggac ccagccttga cagctgctg tgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct ccccctaacc aaattctccc tggaccccat tctgagctcc ccatcaccat
gggaggtggg gcctcaatct aaggccttc cctgtcagaa gggggttgag gcaaaagccc
attacaagct gccatcccct ccccgtttca gtggaccctg tggccaggtg cttttcccta
tccacagggg tgtttgtgtg ttgggtgtgc tttcaataaa gtttgtcact ttctt*
```

FIG.9A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPWMEKAPAHLSLPDPQALKRDVPCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRCA
RRGTKCLRREAPRWDAPLRDPALRQLL*

FIG.9B mouse GP88 protein sequence

MVLMSWLAFAAGLVAG    17

TQCPDGQF·CPVA··CCLDQG·GANYSCCNPLLDTWPRITSHHL    57

DGSC·QTHGHCPAGY·SCLLTVSGTS·SCCPPFSKGVSCGDGYHCCPQGFHCSADGKSCFQMSDNPL    120

GAVQCPGSQFECPDSATCCIMVD·G·SWGCCPMPQASCCEDRVHCCPHGASCDLVHTRCVSPTGIHTLLKKFPAQKTNAAVSLPFS    204    g

VVCPDAKIQCPDDSTCCELP·TGK·YGCCPMPNAICCSDHLHCCPQDTVCDLIQSKCLSKNYTTDLLTKLPGYPVK    278    f

EVKC·DMEVSCPEGYTCCALN·TGA·WGCCPFAKAVCCEDHIHCCPAGFQCHTEKGTCEMGILQVPWMKKVIAPRRLPDPQILKS    360    2.B 1.A

DIPCDDFTR·CPTNNTCCKLN·SGD·WGCCPIPEAVCCSDNQHCCPQGFTCLAQGY·CQKGDTMVAGLEKIPARQTTPLQIG    438    C

DIGCDuHT·SCPVGQTCCPSLK·G·SWACCQLPHAVCCEDRQHCCPAGYTCNVKARTCEKDVDFIQPPVLLTLGPKVG    513    D

NVECGEGHF·CHDNQTCCKDSA·GV·WACCPYLKGVCCRDGRHCCPGGFHCSARGTKCLAKKIPRWDMFLADPVPRPLL    589    e

Consensus sequence:

C......C.....CC.......G.......CC........CC.D..HCCP....C.......C 1,2:mouse epithelin 1,2.
A,B,C,D,e,f,g: granulin A,B,C,D,E,F,G;N-terminus of granulin A,B,C,D have been sequenced.
mouse epithelin precursor sequence is from Plowman et al.(1992).

FIG.10

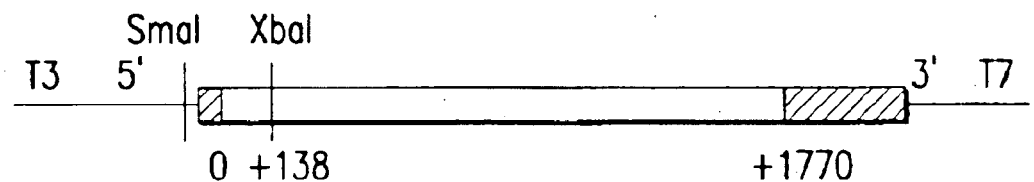
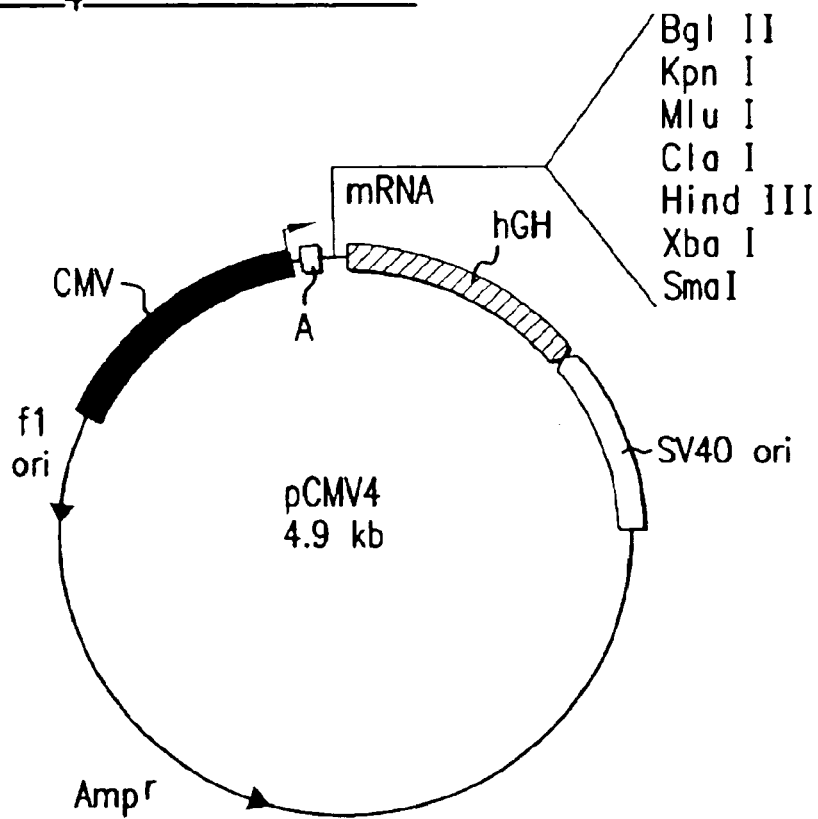
FIG.11

GP88 EXPRESSION IN NON TUMORIGENIC (MCF 10A) AND MALIGNANT (MCF 7, MDA-468) HUMAN MAMMARY EPITHELIAL CELLS

GP88 EXPRESSION IS INHIBITED BY ANTISENSE GP88 cDNA TRANSFECTION IN HUMAN BREAST CARCINOMA MDA-468

FIG. 21
GP88 STAINING WITH ANTI-GP88 ANTIBODY ON PARAFFIN EMBEDDED BREAST CANCER BIOPSIES BY IMMUNOHISTOCHEMISTRY (IHC)
DUCTAL INVASIVE CARCINOMA
BENIGN LESION

SEQUENCE LISTING

<160> NUMBER OF SEQ ID NOS: 17

<210> SEQ ID NO 1
<211> LENGTH: 2137
<212> TYPE: DNA
<213> ORGANISM: Mouse epithelin/granulin
<220> FEATURE:
<221> NAME/KEY: CDS
<222> LOCATION: (23)..(1789)
<223> OTHER INFORMATION: The sequence is identical to that of the
      published mouse granulin except for one nucleotide (T instead
      of G) at position 1071 of GP88 cDNA (position 1056 of
      mouse granulin).

<400> SEQUENCE: 1

```
cggaccccga cgcagacaga cc atg tgg gtc ctg atg agc tgg ctg gcc ttc        52
                         Met Trp Val Leu Met Ser Trp Leu Ala Phe
                          1               5                  10 gcg gca ggg ctg gta gcc gga aca cag tgt cca gat ggg cag ttc tgc       100
Ala Ala Gly Leu Val Ala Gly Thr Gln Cys Pro Asp Gly Gln Phe Cys
             15                  20                  25 cct gtt gcc tgc tgc ctt gac cag gga gga gcc aac tac agc tgc tgt       148
Pro Val Ala Cys Cys Leu Asp Gln Gly Gly Ala Asn Tyr Ser Cys Cys
         30                  35                  40 aac cct ctt ctg gac aca tgg cct aga ata acg agc cat cat cta gat       196
Asn Pro Leu Leu Asp Thr Trp Pro Arg Ile Thr Ser His His Leu Asp
     45                  50                  55 ggc tcc tgc cag acc cat ggc cac tgt cct gct ggc tat tct tgt ctt       244
Gly Ser Cys Gln Thr His Gly His Cys Pro Ala Gly Tyr Ser Cys Leu
 60                  65                  70 ctc act gtg tct ggg act tcc agc tgc tgc ccg ttc tct aag ggt gtg       292
Leu Thr Val Ser Gly Thr Ser Ser Cys Cys Pro Phe Ser Lys Gly Val
 75                  80                  85                  90 tct tgt ggt gat ggc tac cac tgc tgc ccc cag ggc ttc cac tgt agt       340
```

-continued

| | | | | | | | | | | | | | | | |
|---|---|---|---|---|---|---|---|---|---|---|---|---|---|---|---|
| Ser | Cys | Gly | Asp | Gly | Tyr | His | Cys | Cys | Pro | Gln | Gly | Phe | His | Cys | Ser |
| | | | | 95 | | | | 100 | | | | | 105 | | |

| gca | gat | ggg | aaa | tcc | tgc | ttc | cag | atg | tca | gat | aac | ccc | ttg | ggt | gct | 388 |
|---|---|---|---|---|---|---|---|---|---|---|---|---|---|---|---|---|
| Ala | Asp | Gly | Lys | Ser | Cys | Phe | Gln | Met | Ser | Asp | Asn | Pro | Leu | Gly | Ala | |
| | | | 110 | | | | | 115 | | | | | 120 | | | |

| gtc | cag | tgt | cct | ggg | agc | cag | ttt | gaa | tgt | cct | gac | tct | gcc | acc | tgc | 436 |
|---|---|---|---|---|---|---|---|---|---|---|---|---|---|---|---|---|
| Val | Gln | Cys | Pro | Gly | Ser | Gln | Phe | Glu | Cys | Pro | Asp | Ser | Ala | Thr | Cys | |
| | | 125 | | | | | 130 | | | | | 135 | | | | |

| tgc | att | atg | gtt | gat | ggt | tcg | tgg | gga | tgt | tgt | ccc | atg | ccc | cag | gcc | 484 |
|---|---|---|---|---|---|---|---|---|---|---|---|---|---|---|---|---|
| Cys | Ile | Met | Val | Asp | Gly | Ser | Trp | Gly | Cys | Cys | Pro | Met | Pro | Gln | Ala | |
| | 140 | | | | | 145 | | | | | 150 | | | | | |

| tct | tgc | tgt | gaa | gac | aga | gtg | cat | tgc | tgt | ccc | cat | ggg | gcc | tcc | tgt | 532 |
|---|---|---|---|---|---|---|---|---|---|---|---|---|---|---|---|---|
| Ser | Cys | Cys | Glu | Asp | Arg | Val | His | Cys | Cys | Pro | His | Gly | Ala | Ser | Cys | |
| 155 | | | | | 160 | | | | | 165 | | | | | 170 | |

| gac | ctg | gtt | cac | aca | cga | tgc | gtt | tca | ccc | acg | ggc | acc | cac | acc | cta | 580 |
|---|---|---|---|---|---|---|---|---|---|---|---|---|---|---|---|---|
| Asp | Leu | Val | His | Thr | Arg | Cys | Val | Ser | Pro | Thr | Gly | Thr | His | Thr | Leu | |
| | | | | 175 | | | | | 180 | | | | | 185 | | |

| cta | aag | aag | ttc | cct | gca | caa | aag | acc | aac | agc | gca | gtg | tct | ttg | cct | 628 |
|---|---|---|---|---|---|---|---|---|---|---|---|---|---|---|---|---|
| Leu | Lys | Lys | Phe | Pro | Ala | Gln | Lys | Thr | Asn | Ser | Ala | Val | Ser | Leu | Pro | |
| | | | | 190 | | | | | 195 | | | | | 200 | | |

| ttt | tct | gtc | gtg | tgc | cct | gat | gct | aag | acc | cag | tgt | ccc | gat | gat | tct | 676 |
|---|---|---|---|---|---|---|---|---|---|---|---|---|---|---|---|---|
| Phe | Ser | Val | Val | Cys | Pro | Asp | Ala | Lys | Thr | Gln | Cys | Pro | Asp | Asp | Ser | |
| | | 205 | | | | | 210 | | | | | 215 | | | | |

| acc | tgc | tgt | gag | cta | ccc | act | ggg | aag | tat | ggc | tgc | tgt | cca | atg | ccc | 724 |
|---|---|---|---|---|---|---|---|---|---|---|---|---|---|---|---|---|
| Thr | Cys | Cys | Glu | Leu | Pro | Thr | Gly | Lys | Tyr | Gly | Cys | Cys | Pro | Met | Pro | |
| | 220 | | | | | 225 | | | | | 230 | | | | | |

| aat | gcc | atc | tgc | tgt | tcc | gac | cac | ctg | cac | tgc | tgc | ccc | cag | gac | act | 772 |
|---|---|---|---|---|---|---|---|---|---|---|---|---|---|---|---|---|
| Asn | Ala | Ile | Cys | Cys | Ser | Asp | His | Leu | His | Cys | Cys | Pro | Gln | Asp | Thr | |
| 235 | | | | | 240 | | | | | 245 | | | | | 250 | |

| gta | tgt | gac | ctg | atc | cag | agt | aag | tgc | cta | tcc | aag | aac | tac | acc | acg | 820 |
|---|---|---|---|---|---|---|---|---|---|---|---|---|---|---|---|---|
| Val | Cys | Asp | Leu | Ile | Gln | Ser | Lys | Cys | Leu | Ser | Lys | Asn | Tyr | Thr | Thr | |
| | | | | 255 | | | | | 260 | | | | | 265 | | |

| gat | ctc | ctg | acc | aag | ctg | cct | gga | tac | cca | gtg | aag | gag | gtg | aag | tgc | 868 |
|---|---|---|---|---|---|---|---|---|---|---|---|---|---|---|---|---|
| Asp | Leu | Leu | Thr | Lys | Leu | Pro | Gly | Tyr | Pro | Val | Lys | Glu | Val | Lys | Cys | |
| | | | 270 | | | | | 275 | | | | | 280 | | | |

| gac | atg | gag | gtg | agc | tgc | cct | gaa | gga | tat | acc | tgc | tgc | cgc | ctc | aac | 916 |
|---|---|---|---|---|---|---|---|---|---|---|---|---|---|---|---|---|
| Asp | Met | Glu | Val | Ser | Cys | Pro | Glu | Gly | Tyr | Thr | Cys | Cys | Arg | Leu | Asn | |
| | | 285 | | | | | 290 | | | | | 295 | | | | |

| act | ggg | gcc | tgg | ggc | tgc | tgt | cca | ttt | gcc | aag | gcc | gtg | tgt | tgt | gac | 964 |
|---|---|---|---|---|---|---|---|---|---|---|---|---|---|---|---|---|
| Thr | Gly | Ala | Trp | Gly | Cys | Cys | Pro | Phe | Ala | Lys | Ala | Val | Cys | Cys | Asp | |
| | 300 | | | | | 305 | | | | | 310 | | | | | |

| gat | cac | att | cat | tgc | tgc | ccg | gca | ggg | ttt | cag | tgt | cac | aca | gag | aaa | 1012 |
|---|---|---|---|---|---|---|---|---|---|---|---|---|---|---|---|---|
| Asp | His | Ile | His | Cys | Cys | Pro | Ala | Gly | Phe | Gln | Cys | His | Thr | Glu | Lys | |
| 315 | | | | | 320 | | | | | 325 | | | | | 330 | |

| gga | acc | tgc | gaa | atg | ggt | atc | ctc | caa | gta | ggg | tgg | atg | aag | aag | gtc | 1060 |
|---|---|---|---|---|---|---|---|---|---|---|---|---|---|---|---|---|
| Gly | Thr | Cys | Glu | Met | Gly | Ile | Leu | Gln | Val | Gly | Trp | Met | Lys | Lys | Val | |
| | | | | 335 | | | | | 340 | | | | | 345 | | |

| ata | gcc | ccc | ctc | cgc | ctg | cca | gac | cca | cag | atc | ttg | aag | agt | gat | aca | 1108 |
|---|---|---|---|---|---|---|---|---|---|---|---|---|---|---|---|---|
| Ile | Ala | Pro | Leu | Arg | Leu | Pro | Asp | Pro | Gln | Ile | Leu | Lys | Ser | Asp | Thr | |
| | | | 350 | | | | | 355 | | | | | 360 | | | |

| cct | tgt | gat | gac | ttc | act | agg | tgt | cct | aca | aac | aat | acc | tgc | tgc | aaa | 1156 |
|---|---|---|---|---|---|---|---|---|---|---|---|---|---|---|---|---|
| Pro | Cys | Asp | Asp | Phe | Thr | Arg | Cys | Pro | Thr | Asn | Asn | Thr | Cys | Cys | Lys | |
| | | | 365 | | | | | 370 | | | | | 375 | | | |

| ctc | aat | tct | ggg | gac | tgg | ggc | tgc | tgt | ccc | atc | cca | gag | gct | gtc | tgc | 1204 |
|---|---|---|---|---|---|---|---|---|---|---|---|---|---|---|---|---|
| Leu | Asn | Ser | Gly | Asp | Trp | Gly | Cys | Cys | Pro | Ile | Pro | Glu | Ala | Val | Cys | |
| | | 380 | | | | | 385 | | | | | 390 | | | | |

| tgc | tca | gac | aac | cag | cat | tgc | tgc | cct | cag | ggc | ttc | aca | tgt | ctg | gct | 1252 |
|---|---|---|---|---|---|---|---|---|---|---|---|---|---|---|---|---|
| Cys | Ser | Asp | Asn | Gln | His | Cys | Cys | Pro | Gln | Gly | Phe | Thr | Cys | Leu | Ala | |
| 395 | | | | | 400 | | | | | 405 | | | | | 410 | |

-continued

| | | |
|---|---|---|
| cag ggg tac tgt cag aag gga gac aca atg gtg gct ggc ctg gag aag<br>Gln Gly Tyr Cys Gln Lys Gly Asp Thr Met Val Ala Gly Leu Glu Lys<br>415 420 425 | | 1300 |
| ata cct gcc cgc cag aca acc ccg ctc caa att gga gat atc ggt tgt<br>Ile Pro Ala Arg Gln Thr Thr Pro Leu Gln Ile Gly Asp Ile Gly Cys<br>430 435 440 | | 1348 |
| gac cag cat acc agc tgc cca gta ggg caa acc tgc tgc cca agc ctc<br>Asp Gln His Thr Ser Cys Pro Val Gly Gln Thr Cys Cys Pro Ser Leu<br>445 450 455 | | 1396 |
| aag gga agt tgg gcc tgc tgc cag ctg ccc cat gct gtg tgc tgt gag<br>Lys Gly Ser Trp Ala Cys Cys Gln Leu Pro His Ala Val Cys Cys Glu<br>460 465 470 | | 1444 |
| gac cgg cag cac tgt tgc ccg gcc ggg tac acc tgc aac gtg aag gcg<br>Asp Arg Gln His Cys Cys Pro Ala Gly Tyr Thr Cys Asn Val Lys Ala<br>475 480 485 490 | | 1492 |
| agg acc tgt gag aag gat gtc gat ttt atc cag cct ccc gtg ctc ctg<br>Arg Thr Cys Glu Lys Asp Val Asp Phe Ile Gln Pro Pro Val Leu Leu<br>495 500 505 | | 1540 |
| acc ctc ggc cct aag gtt ggg aat gtg gag tgt gga gaa ggg cat ttc<br>Thr Leu Gly Pro Lys Val Gly Asn Val Glu Cys Gly Glu Gly His Phe<br>510 515 520 | | 1588 |
| tgc cat gat aac cag acc tgt tgt aaa gac agt gca gga gtc tgg gcc<br>Cys His Asp Asn Gln Thr Cys Cys Lys Asp Ser Ala Gly Val Trp Ala<br>525 530 535 | | 1636 |
| tgt tgt ccc tac cta aag ggt gtc tgc tgt aga gat gga cgt cac tgt<br>Cys Cys Pro Tyr Leu Lys Gly Val Cys Cys Arg Asp Gly Arg His Cys<br>540 545 550 | | 1684 |
| tgc ccc ggt ggc ttc cac tgt tca gcc agg gga acc aag tgt ttg cga<br>Cys Pro Gly Gly Phe His Cys Ser Ala Arg Gly Thr Lys Cys Leu Arg<br>555 560 565 570 | | 1732 |
| aag aag att cct cgc tgg gac atg ttt ttg agg gat ccg gtc cca aga<br>Lys Lys Ile Pro Arg Trp Asp Met Phe Leu Arg Asp Pro Val Pro Arg<br>575 580 585 | | 1780 |
| ccg cta ctg taaggaaggg ctacagactt aaggaactcc acagtcctgg<br>Pro Leu Leu | | 1829 |
| gaaccctgtt ccgagggtac ccactactca ggcctcccta gcgcctcctc ccctaacgtc | | 1889 |
| tccccggcct actcatcctg agtcacccta tcaccatggg aggtggagcc tcaaactaaa | | 1949 |
| accttctttt atgaaagaa ggctctggcc aaaagccccg tatcaaactg ccatttcttc | | 2009 |
| cggtttctgt ggaccttgtg ccaggtgct cttcccgagc acaggtgtt ctgtgagctt | | 2069 |
| gcttgtgtgt gtgtgcgcgt gtgcgtgtgt tgctccaata agtttgtac gctttctgaa | | 2129 |
| aaaaaaaa | | 2137 |

<210> SEQ ID NO 2
<211> LENGTH: 589
<212> TYPE: PRT
<213> ORGANISM: Mouse epithelin/granulin

<400> SEQUENCE: 2

Met Trp Val Leu Met Ser Trp Leu Ala Phe Ala Ala Gly Leu Val Ala
1               5                   10                  15

Gly Thr Gln Cys Pro Asp Gly Gln Phe Cys Pro Val Ala Cys Cys Leu
            20                  25                  30

Asp Gln Gly Gly Ala Asn Tyr Ser Cys Cys Asn Pro Leu Leu Asp Thr
        35                  40                  45

Trp Pro Arg Ile Thr Ser His His Leu Asp Gly Ser Cys Gln Thr His
    50                  55                  60

-continued

```
Gly His Cys Pro Ala Gly Tyr Ser Cys Leu Leu Thr Val Ser Gly Thr
 65                  70                  75                  80

Ser Ser Cys Cys Pro Phe Ser Lys Gly Val Ser Cys Gly Asp Gly Tyr
             85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
        115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Ser Ala Val Ser Leu Pro Phe Ser Val Val Cys Pro
        195                 200                 205

Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300

Cys Pro Phe Ala Lys Ala Val Cys Cys Asp Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Gly Trp Met Lys Lys Val Ile Ala Pro Leu Arg Leu
            340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
            420                 425                 430

Thr Pro Leu Gln Ile Gly Asp Ile Gly Cys Asp Gln His Thr Ser Cys
        435                 440                 445

Pro Val Gly Gln Thr Cys Cys Pro Ser Leu Lys Gly Ser Trp Ala Cys
    450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
```

```
                    485                 490                 495
Val Asp Phe Ile Gln Pro Pro Val Leu Leu Thr Leu Gly Pro Lys Val
                500                 505                 510
Gly Asn Val Glu Cys Gly Glu Gly His Phe Cys His Asp Asn Gln Thr
            515                 520                 525
Cys Cys Lys Asp Ser Ala Gly Val Trp Ala Cys Cys Pro Tyr Leu Lys
        530                 535                 540
Gly Val Cys Cys Arg Asp Gly Arg His Cys Cys Pro Gly Gly Phe His
545                 550                 555                 560
Cys Ser Ala Arg Gly Thr Lys Cys Leu Arg Lys Lys Ile Pro Arg Trp
                565                 570                 575
Asp Met Phe Leu Arg Asp Pro Val Pro Arg Pro Leu Leu
            580                 585
```

<210> SEQ ID NO 3
<211> LENGTH: 19
<212> TYPE: PRT
<213> ORGANISM: mouse granulin
<220> FEATURE:
<221> NAME/KEY: PEPTIDE
<222> LOCATION: (1)..(19)
<223> OTHER INFORMATION: Internal peptide of mouse GP88 used to raise
      the antisera against the GP88 used in the immunoaffinity step.

<400> SEQUENCE: 3

```
Lys Lys Val Ile Ala Pro Arg Arg Leu Pro Asp Pro Gln Ile Leu Lys
 1               5                  10                  15
Ser Asp Thr
```

<210> SEQ ID NO 4
<211> LENGTH: 12
<212> TYPE: PRT
<213> ORGANISM: mouse granulin
<220> FEATURE:
<221> NAME/KEY: PEPTIDE
<222> LOCATION: (1)..(12)
<223> OTHER INFORMATION: Internal peptide of mouse GP88 used to raise
      the antisera against the GP88 used in the immunoaffinity step.

<400> SEQUENCE: 4

```
Pro Asp Ala Lys Thr Gln Cys Pro Asp Asp Ser Thr
 1               5                  10
```

<210> SEQ ID NO 5
<211> LENGTH: 14
<212> TYPE: PRT
<213> ORGANISM: mouse granulin
<220> FEATURE:
<221> NAME/KEY: PEPTIDE
<222> LOCATION: (1)..(14)
<223> OTHER INFORMATION: Internal peptide of mouse GP88 used to raise
      the antisera against the GP88 used in the immunoaffinity step.

<400> SEQUENCE: 5

```
Ser Ala Arg Gly Thr Lys Cys Leu Arg Lys Lys Ile Pro Arg
 1               5                  10
```

<210> SEQ ID NO 6
<211> LENGTH: 19
<212> TYPE: PRT
<213> ORGANISM: Human granulin
<220> FEATURE:
<221> NAME/KEY: PEPTIDE
<222> LOCATION: (1)..(19)
<223> OTHER INFORMATION: Internal peptide of human GP88 used to develop -continued neutralizing anti-human GP88 monoclonal antibody.

<400> SEQUENCE: 6

Glu Lys Ala Pro Ala His Leu Ser Leu Pro Asp Pro Gln Ala Leu Lys
 1               5                  10                  15

Arg Asp Val

<210> SEQ ID NO 7
<211> LENGTH: 14
<212> TYPE: PRT
<213> ORGANISM: Human granulin
<220> FEATURE:
<221> NAME/KEY: PEPTIDE
<222> LOCATION: (1)..(14)
<223> OTHER INFORMATION: Internal peptide of human GP88 used to develop
      neutralizing anti-human GP88 monoclonal antibody.

<400> SEQUENCE: 7

Ala Arg Arg Gly Thr Lys Cys Leu Arg Arg Glu Ala Pro Arg
 1               5                  10

<210> SEQ ID NO 8
<211> LENGTH: 24
<212> TYPE: DNA
<213> ORGANISM: mammalian
<220> FEATURE:
<221> NAME/KEY: primer
<222> LOCATION: (1)..(24)
<223> OTHER INFORMATION: Internal peptide of CMV promoter used as PCR
      primer.

<400> SEQUENCE: 8
cctacttggc agtacatcta cgta                                          24

<210> SEQ ID NO 9
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: GP88 cDNA start codon used as oligonucleotide
      PCR primer.

<400> SEQUENCE: 9
cgagaattca ggcagaccat gtgggtc                                       27

<210> SEQ ID NO 10
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: Antisense primer oligonucleotide primer

<400> SEQUENCE: 10
cgagaattca ggcagaccat gtgggtc                                       27

<210> SEQ ID NO 11
<211> LENGTH: 23
<212> TYPE: DNA
<213> ORGANISM: mammalian
<220> FEATURE:
<221> NAME/KEY: primer
<222> LOCATION: (1)..(23)
<223> OTHER INFORMATION: Antisense primer oligonucleotide primer -continued

```
<400> SEQUENCE: 11
ctgacggttc actaaacgag ctc                                             23

<210> SEQ ID NO 12
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: primer

<400> SEQUENCE: 12
ggatccacgg agttgttacc tgatc                                           25

<210> SEQ ID NO 13
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: oligonucleotide PCR primer

<400> SEQUENCE: 13
gaattcgcag gcagaccatg tggac                                           25

<210> SEQ ID NO 14
<211> LENGTH: 21
<212> TYPE: DNA
<213> ORGANISM: mammalian
<220> FEATURE:
<221> NAME/KEY: primer
<222> LOCATION: (1)..(21)
<223> OTHER INFORMATION: Antisense oligonucleotide to human GP88

<400> SEQUENCE: 14
gggtccacat ggtctgcctg c                                               21

<210> SEQ ID NO 15
<211> LENGTH: 24
<212> TYPE: DNA
<213> ORGANISM: mammalian
<220> FEATURE:
<221> NAME/KEY: primer
<222> LOCATION: (1)..(24)
<223> OTHER INFORMATION: Antisense oligonucleotide to human GP88

<400> SEQUENCE: 15
gccaccagcc ctgctgttaa ggcc                                            24

<210> SEQ ID NO 16
<211> LENGTH: 2095
<212> TYPE: DNA
<213> ORGANISM: Human GP88 cDNA
<220> FEATURE:
<221> NAME/KEY: CDS
<222> LOCATION: (13)..(1791)
<223> OTHER INFORMATION: Nucleotide sequence of human granulin/
      epithelin precursor (human GP88).  Human Granulin Genebank
      M75161.

<400> SEQUENCE: 16
cgcaggcaga cc atg tgg acc ctg gtg agc tgg gtg gcc tta aca gca ggg    51
              Met Trp Thr Leu Val Ser Trp Val Ala Leu Thr Ala Gly
                1               5                   10 ctg gtg gct gga acg cgg tgc cca gat ggt cag ttc tgc cct gtg gcc     99
```

| | | |
|---|---|---|
| Leu Val Ala Gly Thr Arg Cys Pro Asp Gly Gln Phe Cys Pro Val Ala<br>15                  20                  25 | | |
| tgc tgc ctg gac ccc gga gga gcc agc tac agc tgc tgc cgt ccc ctt<br>Cys Cys Leu Asp Pro Gly Gly Ala Ser Tyr Ser Cys Cys Arg Pro Leu<br>30                  35                  40                  45 | | 147 |
| ctg gac aaa tgg ccc aca aca ctg agc agg cat ctg ggt ggc ccc tgc<br>Leu Asp Lys Trp Pro Thr Thr Leu Ser Arg His Leu Gly Gly Pro Cys<br>              50                  55                  60 | | 195 |
| cag gtt gat gcc cac tgc tct gcc ggc cac tcc tgc atc ttt acc gtc<br>Gln Val Asp Ala His Cys Ser Ala Gly His Ser Cys Ile Phe Thr Val<br>                  65                  70                  75 | | 243 |
| tca ggg act tcc agt tgc tgc ccc ttc cca gag gcc gtg gca tgc ggg<br>Ser Gly Thr Ser Ser Cys Cys Pro Phe Pro Glu Ala Val Ala Cys Gly<br>              80                  85                  90 | | 291 |
| gat ggc cat cac tgc tgc cca cgg ggc ttc cac tgc agt gca gac ggg<br>Asp Gly His His Cys Cys Pro Arg Gly Phe His Cys Ser Ala Asp Gly<br>                  95                  100                 105 | | 339 |
| cga tcc tgc ttc caa aga tca ggt aac aac tcc gtg ggt gcc atc cag<br>Arg Ser Cys Phe Gln Arg Ser Gly Asn Asn Ser Val Gly Ala Ile Gln<br>110                 115                 120                 125 | | 387 |
| tgc cct gat agt cag ttc gaa tgc ccg gac ttc tcc acg tgc tgt gtt<br>Cys Pro Asp Ser Gln Phe Glu Cys Pro Asp Phe Ser Thr Cys Cys Val<br>              130                 135                 140 | | 435 |
| atg gtc gat ggc tcc tgg ggg tgc tgc ccc atg ccc cag gct tcc tgc<br>Met Val Asp Gly Ser Trp Gly Cys Cys Pro Met Pro Gln Ala Ser Cys<br>                  145                 150                 155 | | 483 |
| tgt gaa gac agg gtg cac tgc tgt ccg cac ggt gcc ttc tgc gac ctg<br>Cys Glu Asp Arg Val His Cys Cys Pro His Gly Ala Phe Cys Asp Leu<br>              160                 165                 170 | | 531 |
| gtt cac acc cgc tgc atc aca ccc acg ggc acc cac ccc ctg gca aag<br>Val His Thr Arg Cys Ile Thr Pro Thr Gly Thr His Pro Leu Ala Lys<br>                  175                 180                 185 | | 579 |
| aag ctc cct gcc cag agg act aac agg gca gtg gcc ttg tcc agc tcg<br>Lys Leu Pro Ala Gln Arg Thr Asn Arg Ala Val Ala Leu Ser Ser Ser<br>190                 195                 200                 205 | | 627 |
| gtc atg tgt ccg gac gca cgg tcc cgg tgc cct gat ggt tct acc tgc<br>Val Met Cys Pro Asp Ala Arg Ser Arg Cys Pro Asp Gly Ser Thr Cys<br>              210                 215                 220 | | 675 |
| tgt gag ctg ccc agt ggg aag tat ggc tgc tgc cca atg ccc aac gcc<br>Cys Glu Leu Pro Ser Gly Lys Tyr Gly Cys Cys Pro Met Pro Asn Ala<br>                  225                 230                 235 | | 723 |
| acc tgc tgc tcc gat cac ctg cac tgc tgc ccc caa gac act gtg tgt<br>Thr Cys Cys Ser Asp His Leu His Cys Cys Pro Gln Asp Thr Val Cys<br>              240                 245                 250 | | 771 |
| gac ctg atc cag agt aag tgc ctc tcc aag gag aac gct acc acg gac<br>Asp Leu Ile Gln Ser Lys Cys Leu Ser Lys Glu Asn Ala Thr Thr Asp<br>255                 260                 265 | | 819 |
| ctc ctc act aag ctg cct gcg cac aca gtg ggc gat gtg aaa tgt gac<br>Leu Leu Thr Lys Leu Pro Ala His Thr Val Gly Asp Val Lys Cys Asp<br>270                 275                 280                 285 | | 867 |
| atg gag gtg agc tgc cca gat ggc tat acc tgc tgc cgt cta cag tcg<br>Met Glu Val Ser Cys Pro Asp Gly Tyr Thr Cys Cys Arg Leu Gln Ser<br>              290                 295                 300 | | 915 |
| ggg gcc tgg ggc tgc tgc cct ttt acc cag gct gtg tgc tgt gag gac<br>Gly Ala Trp Gly Cys Cys Pro Phe Thr Gln Ala Val Cys Cys Glu Asp<br>              305                 310                 315 | | 963 |
| cac ata cac tgc tgt ccc gcg ggg ttt acg tgt gac acg cag aag ggt<br>His Ile His Cys Cys Pro Ala Gly Phe Thr Cys Asp Thr Gln Lys Gly<br>              320                 325                 330 | | 1011 |

```
acc tgt gaa cag ggg ccc cac cag gtg ccc tgg atg gag aag gcc cca    1059
Thr Cys Glu Gln Gly Pro His Gln Val Pro Trp Met Glu Lys Ala Pro
        335                 340                 345 gct cac ctc agc ctg cca gac cca caa gcc ttg aag aga gat gtc ccc    1107
Ala His Leu Ser Leu Pro Asp Pro Gln Ala Leu Lys Arg Asp Val Pro
350                 355                 360                 365 tgt gat aat gtc agc agc tgt ccc tcc tcc gat acc tgc tgc caa ctc    1155
Cys Asp Asn Val Ser Ser Cys Pro Ser Ser Asp Thr Cys Cys Gln Leu
            370                 375                 380 acg tct ggg gag tgg ggc tgt tgt cca atc cca gag gct gtc tgc tgc    1203
Thr Ser Gly Glu Trp Gly Cys Cys Pro Ile Pro Glu Ala Val Cys Cys
                385                 390                 395 tcg gac cac cag cac tgc tgc ccc cag cga tac acg tgt gta gct gag    1251
Ser Asp His Gln His Cys Cys Pro Gln Arg Tyr Thr Cys Val Ala Glu
            400                 405                 410 ggg cag tgt cag cga gga agc gag atc gtg gct gga ctg gag aag atg    1299
Gly Gln Cys Gln Arg Gly Ser Glu Ile Val Ala Gly Leu Glu Lys Met
415                 420                 425 cct gcc cgc cgc ggt tcc tta tcc cac ccc aga gac atc ggc tgt gac    1347
Pro Ala Arg Arg Gly Ser Leu Ser His Pro Arg Asp Ile Gly Cys Asp
430                 435                 440                 445 cag cac acc agc tgc ccg gtg ggc gga acc tgc tgc ccg agc cag ggt    1395
Gln His Thr Ser Cys Pro Val Gly Gly Thr Cys Cys Pro Ser Gln Gly
            450                 455                 460 ggg agc tgg gcc tgc tgc cag ttg ccc cat gct gtg tgc tgc gag gat    1443
Gly Ser Trp Ala Cys Cys Gln Leu Pro His Ala Val Cys Cys Glu Asp
                465                 470                 475 cgc cag cac tgc tgc ccg gct ggc tac acc tgc aac gtg aag gct cga    1491
Arg Gln His Cys Cys Pro Ala Gly Tyr Thr Cys Asn Val Lys Ala Arg
            480                 485                 490 tcc tgc gag aag gaa gtg gtc tct gcc cag cct gcc acc ttc ctg gcc    1539
Ser Cys Glu Lys Glu Val Val Ser Ala Gln Pro Ala Thr Phe Leu Ala
495                 500                 505 cgt agc cct cac gtg ggt gtg aag gac gtg gag tgt ggg gaa gga cac    1587
Arg Ser Pro His Val Gly Val Lys Asp Val Glu Cys Gly Glu Gly His
510                 515                 520                 525 ttc tgc cat gat aac cag acc tgc tgc cga gac aac cga cag ggc tgg    1635
Phe Cys His Asp Asn Gln Thr Cys Cys Arg Asp Asn Arg Gln Gly Trp
            530                 535                 540 gcc tgc tgt ccc tac gcc cag ggc gtc tgt tgt gct gat cgg cgc cac    1683
Ala Cys Cys Pro Tyr Ala Gln Gly Val Cys Cys Ala Asp Arg Arg His
                545                 550                 555 tgc tgt cct gct ggc ttc cgc tgc gca cgc agg ggt acc aag tgt ttg    1731
Cys Cys Pro Ala Gly Phe Arg Cys Ala Arg Arg Gly Thr Lys Cys Leu
            560                 565                 570 cgc agg gag gcc ccg cgc tgg gac gcc cct ttg agg gac cca gcc ttg    1779
Arg Arg Glu Ala Pro Arg Trp Asp Ala Pro Leu Arg Asp Pro Ala Leu
575                 580                 585 aga cag ctg ctg tgagggacag tactgaagac tctgcagccc tcgggacccc        1831
Arg Gln Leu Leu
590 actcggaggg tgccctctgc tcaggcctcc ctagcacctc cccctaacca aattctccct  1891 ggaccccatt ctgagctccc catcaccatg ggaggtgggg cctcaatcta aggcccttcc  1951 ctgtcagaag ggggttgagg caaaagccca ttacaagctg ccatccctc cccgtttcag   2011 tggaccctgt ggccaggtgc ttttccctat ccacaggggt gtttgtgtgt tgggtgtgct  2071 ttcaataaag tttgtcactt tctt                                        2095
```

<210> SEQ ID NO 17
<211> LENGTH: 593
<212> TYPE: PRT
<213> ORGANISM: Human GP88 cDNA

<400> SEQUENCE: 17

```
Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380
```

-continued

```
Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Gly Ser Leu Ser His Pro Arg Asp Ile Gly Cys Asp Gln His Thr
            435                 440                 445

Ser Cys Pro Val Gly Gly Thr Cys Cys Pro Ser Gln Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
                500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
            530                 535                 540

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu
```

METHODS AND KITS FOR DIAGNOSING TUMORIGENICITY AND DETERMINING RESISTANCE TO THE ANTINEOPLASTIC EFFECTS OF ANTIESTROGEN THERAPY

This application is a continuation-in-part of U.S. application Ser. No. 09/456,886, filed Dec. 8, 1999, now U.S. Pat. No. 6,720,159 which is a divisional of U.S. application Ser. No. 08/863,079, filed May 23, 1997, now abandoned.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression. Typically, growth factors are produced in one cell and act on another cell to stimulate proliferation. However, certain malignant cells, in culture, demonstrate a greater or absolute reliance on an autocrine growth mechanism. Malignant cells which observe this autocrine behavior circumvent the regulation of growth factor production by other cells and are therefore unregulated in their growth.

Study of autocrine growth control advances understanding of cell growth mechanisms and leads to important advances in the diagnosis and treatment of cancer. Toward this end, a number of growth factors have been studied, including insulin-like growth factors ("IGF1" and "IGF2"), gastrin-releasing peptide ("GRP"), transforming growth factors alpha and beta ("TGF-a" and "TGF"), and epidermal growth factor ("EGF").

The present invention is directed to a recently discovered growth factor. This growth factor was first discovered in the culture medium of highly tumorigenic "PC cells," an insulin-independent variant isolated from the teratoma derived adipogenic cell line 1246. This growth factor is referred to herein as "GP88." GP88 has been purified and structurally characterized. Amino acid sequencing of GP88 indicates that GP88 has amino acid sequence similarities with the mouse granulin/epithelin precursor.

Granulins/epithelins ("grn/epi") are 6 kDa polypeptides and belong to a novel family of double cysteine rich polypeptides. U.S. Pat. No. 5,416,192 (Shoyab et al.) is directed to 6 kDa epithelins, particularly epithelin 1 and epithelin 2. According to Shoyab, both epithelins are encoded by a common 63.5 kDa precursor, which is processed into smaller forms as soon as it is synthesized, so that the only natural products found in biological samples are the 6 kDa forms. Shoyab et al. teaches that the epithelin precursor is biologically inactive.

Contrary to the teachings of Shoyab et al., the present inventor's laboratory has demonstrated that the precursor is not always processed as soon as it is synthesized. Studies, conducted in part by this inventor, have demonstrated that the precursor (i.e., GP88) is in fact secreted as an 88 kDa glycoprotein with an N-linked carbohydrate moiety of 20 kDa. Analysis of the N-terminal sequence of GP88 indicates that GP88 starts at amino acid 17 of the grn/epi precursor, demonstrating that the first 17 amino acids from the protein sequence deduced from the precursor cDNA correspond to a signal peptide compatible with targeting for membrane localization or for secretion. In contrast to the teachings of Shoyab et al., GP88 is biologically active and has growth promoting activity, particularly as an autocrine growth factor for the producer cells.

Breast cancer is a major worldwide cause of morbidity and mortality among women. Estrogen is known to be a primary stimulator for estrogen receptor positive ($ER^+$) human breast cancer cell growth in vivo and in vitro. Although estrogen is initially required for establishment and proliferation of breast tumors, the development of estrogen-independent tumors during the course of breast cancer is indicative of poor prognosis. It has been postulated that the mitogenic effect of estrogen in breast cancer cells is mediated, at least partially, by autocrine growth factors, including growth factors regulated by estrogen. Thus, the identification and characterization of estrogen-responsive genes, particularly genes encoding growth factors, contributes to the understanding of the effects of estrogen in breast cancer cells.

Tamoxifen citrate ("tamoxifen") is a nonsteroidal antiestrogen commonly prescribed to patients suffering from breast cancer that has demonstrated potent antiestrogenic and antineoplastic properties. See U.S. Pat. No. 4,536,516. Tamoxifen is an estrogen receptor antagonist that competes with estrogen for binding to estrogen receptors. Other antiestrogens include, raloxifene, aromatase inhibitors (e.g., Arimidex® (anastrozole), Femera®), and estrogen receptor down-regulators (e.g., Faslodex®). The antiestrogenic effects of tamoxifen may be related to its ability to compete with estrogen for binding sites in target tissues. Other antiestrogens, such as aromatase inhibitors, inhibit or reduce the amount of estrogen available. For example, aromatase inhibitors prevent the conversion of androgen into estrogen thereby reducing the amount of estrogen available. Estrogen receptor down regulators inhibit or reduce the number of estrogen receptors on the cell.

Tamoxifen is currently available in 10 and 20 mg tablets from AstraZeneca and Barr Laboratories under the brand name Nolvadex® and is indicated for metastatic breast cancer, adjuvant therapy of breast cancer, ductal carcinoma in situ, and reduction of breast cancer incidence in women at high risk for breast cancer. Thus, tamoxifen can be used to treat and prevent various cancers and particularly breast cancer.

Tamoxifen administration, however, carries with it potentially serious risks for the patient. For example, tamoxifen administration has been associated with an increased risk of ovarian cancer. Moreover, some patients exhibit resistance to the intended beneficial effects of tamoxifen. Therefore, administration of tamoxifen to a patient who is resistant to its benefits causes unnecessary harm to the patient by increasing the risk of ovarian cancer and at the same time delaying or causing the patient to forego more effective treatments.

Accordingly, tamoxifen administration should be limited to those patients who are most likely to benefit from treatment with tamoxifen. An accurate determination of whether a patient will be susceptible or resistant to the antineoplastic effects of tamoxifen administration, before embarking on such a treatment course, would be a valuable diagnostic tool.

The art currently teaches that the absence of estrogen receptor in a patient corresponds with tamoxifen resistance. Cancer patients are routinely tested for the presence or absence of the estrogen receptor in an attempt to predict whether the patient's will be resistant or responsive to tamoxifen therapy. Based on the current test, cancer patients who tests positive for the presence of estrogen receptors ("ER$_+$," or "estrogen receptor positive patients") are typically prescribed tamoxifen.

However, a significant number of ER$_+$ patients are in fact resistant to tamoxifen. Thus, routinely prescribing tamoxifen for ER$_+$ patients may be harmful, and increase the patient's risk of developing ovarian or other forms of cancer.

SUMMARY OF INVENTION

The inventor has now unexpectedly discovered that a glycoprotein (GP88), which is expressed in a tightly regulated fashion in normal cells, is overexpressed and unregulated in highly tumorigenic cells derived from the normal cells, that GP88 acts as a stringently required growth stimulator for the tumorigenic cells and that inhibition of GP88 expression or action in the tumorigenic cells results in an inhibition of the tumorigenic properties of the overproducing cells. Furthermore, the level of GP88 in a cell directly correlates with the tumorigenicity of the cell.

The inventor has further unexpectedly discovered that the level of GP88 expression indicates whether a patient will be resistant to the pharmacological effects of antiestrogenic compounds such as tamoxifen. The estrogen receptor status of tumor cells in breast cancer patients does not provide sufficient information to determine whether tamoxifen is an appropriate or preferable treatment course in breast cancer patients. The instant invention provides a more accurate tool for determining whether a subject is tamoxifen resistant and therefore represents a valuable advancement in the treatment of cancer.

Preferred embodiments of the invention provide methods for diagnosing tumorigenicity comprising obtaining a biological sample containing cells from a patient, detecting GP88 in the cells of the sample, determining the number of GP88 positive or stained cells in the sample, and determining the ratio of GP88 positive or stained cells to the total number of cells in said biological sample. The ratio is indicative of tumorigenicity.

The present invention also provides methods of determining whether a subject is resistant to the anti-neoplastic effects of antiestrogens. According to a particularly preferred embodiment, GP88 is detected in a biological sample containing cells from a patient and the amount of GP88 in the sample is determined. The amount of GP88 in the biological sample is indicative of resistance to the antineoplastic effects of antiestrogen therapy. In another preferred embodiment, the number of GP88 positive or stained cells in a biological sample is determined, and the ratio of GP88 positive or stained cells to the total number of cells in the biological sample is determined. The ratio is indicative of resistance to the antineoplastic effects of antiestrogen therapy.

Preferred embodiments of the invention also provide kits for diagnosing tumorigenicity and determining whether a patient is resistant to the anti-neoplastic effects of antiestrogens. Such kits preferably comprise a container and a compound or compounds for detecting GP88 (e.g., anti-GP88 antibodies, and anti-GP88 nucleotide probes).

Another preferred embodiment of the invention provides methods of treating or preventing cancer. According to one preferred embodiment, the amount of GP88 in a biological sample obtained from a patient is determined and antiestrogen therapy is administered to the patient if the amount of GP88 in the sample is less than about 5%. Alternatively, antiestrogen therapy is administered to an estrogen receptor positive patient if the amount of GP88 in the biological samples is less than about 10%. In another preferred embodiment, the percentage of GP88 positive cells in a biological sample obtained from a patient is determined and antiestrogen therapy is administered to the patient in an amount sufficient to treat or prevent the cancer if the percentage of GP88 positive or stained cells in the biological sample is less than about 5%. Alternatively, antiestrogen therapy is administered to an estrogen receptor positive patient if the percentage of GP88 positive or stained cells in the biological sample is less than about 10%.

The present invention provides compositions for diagnosis and treatment of diseases such as, but not limited to, cancer in which cells exhibit an altered expression of GP88 or altered response to GP88. Use of the term "altered expression" herein means increased expression or overexpression of GP88 by a factor of at least two-fold, and at times by a factor of 10 or more, based on the level of mRNA or protein as compared to corresponding normal cells or surrounding peripheral cells. The term "altered expression" also means expression which became unregulated or constitutive without being necessarily elevated. Use of the terms increased or altered "response" to GP88 means a condition wherein increase in any of the biological functions (e.g., growth, differentiation, viral infectivity) conferred by GP88 results in the same or equivalent condition as altered expression of GP88.

"Neoplasia" refers to abnormal cell or tumor cell growth that persists in the absence of the original growth stimulus. The term "anti-neoplastic effect" refers to the property of reversing or inhibiting neoplasia. The term "cancer" refers to any disease caused by abnormal cell growth and includes, but is not limited to, breast, ovarian, kidney, bone, pancreatic, testicular, liver, brain, and skin cancer. The term "tumorigenicity" refers to the degree to which a cell or tissue exhibits the characteristics of neoplasia.

As used herein, "ER" refers to estrogen receptor, unless otherwise stated. "PR" refers to progesterone receptor, unless otherwise stated.

"GP88 positive cells" or "GP88 stained cells" refers to those cells in which GP88 is detected. As used herein, "GP88 negative cells" refers to those cells in which GP88 is not detected. Whether a cell is GP88 positive or negative may depend, in part, on the sensitivity of the detection method (i.e., immunostaining, in situ hybridization, imaging). "Total number of cells" refers to the total number of cells analyzed in a biological sample and may include all or some of the cells present in a particular portion of a biological sample.

The term "biological sample" refers to material derived from the body of a vertebrate animal, including, but not limited to, blood, serum, plasma, urine, nipple aspirate, cerebrospinal fluid, liver, kidney, breast, bone, bone marrow, testes or ovaries and brain, colon, and lung.

As used herein, a subject who is "resistant to" antiestrogen therapy is a patient that is nonresponsive to or has reduced or limited response to the antineoplastic effects of antiestrogen therapy.

The term "antiestrogen therapy" refers to administration of compounds that prevent the formation or interfere with the function of estrogen or estrogen analogs. Examples of compounds used for antiestrogen therapy are referred to herein as "antiestrogens" and include, but are not limited to, tamoxifen, raloxifene, aromatase inhibitors (e.g., Arimidex®, Femera®), and estrogen receptor down-regulators (e.g., Faslodex®).

Use of the term "GP88" herein means epithelin/granulin precursor in cell extracts and extracellular fluids, and is intended to include not only GP88 according to the amino acid sequences included in FIGS. 8 or 9, which are of mouse and human origins, but also GP88 of other species. In addition, the term also includes functional derivatives thereof having additional components such as a carbohydrate moiety including a glycoprotein or other modified structures. The terms "GP88" and "PCDGF" are used interchangeably herein. Also intended by the term GP88 is any polypeptide fragment having at least 10 amino-acids present in the above mentioned sequences. Sequences of this length are useful as antigens and for making immunogenic conjugates with carriers for the production of antibodies specific for various epitopes of the entire protein. Such polypeptides are useful in screening such antibodies and in the methods directed to detection of GP88 in biological fluids. It is well known in the art that peptides are useful in generation of antibodies to larger proteins. In one embodiment of this invention, it is shown that peptides from 12–19 amino-acids in length have been successfully used to develop antibodies that recognize the full length GP88.

The polypeptide of this invention may exist covalently or non-covalently bound to another molecule. For example, it may be fused to one or more other polypeptides via one or more peptide bonds such as glutathione transferase, poly-histidine, green fluorescent protein, myc tag, or other tagged compounds (e.g., biotin).

The polypeptide is sufficiently large to comprise an antigenetically distinct determinant or epitope which can be used as an immunogen to reproduce or test antibodies against GP88 or a functional derivative thereof.

One embodiment includes the polypeptide substantially free of other mammalian peptides. GP88 of the present invention can be biochemically or immunochemically purified from cells, tissues or a biological fluid. Alternatively, the polypeptide can be produced by recombinant means in a prokaryotic or eukaryotic expression system and host cells.

A "fragment" of GP88 refers to any subset of the molecule that is a shorter peptide. This corresponds for example but is not limited to regions such as K19T and S14R for mouse GP88, and E19V and A14R (equivalent to murine K19T and S14R, respectively) for human GP88.

"variant" of GP88 refers to a molecule substantially similar to either the entire peptide or a fragment thereof. Variant peptides may be prepared by direct chemical synthesis of the variant peptide using methods known in the art.

Alternatively, amino acid sequence variants of the peptide can be prepared by modifying the DNA which encodes the synthesized protein or peptide. Such variants include, for example, deletions, insertions, or substitutions of residues within the amino-acid sequence of GP88. Any combination of deletion, insertion, and substitution may also be made to arrive at the final construct, provided the final construct possesses the desired activity. The mutation that will be made in the DNA encoding the variant peptide must not alter the reading frame and preferably will not create complementary regions that could produce secondary mRNA structures. At the genetic level these variants are prepared by site directed mutagenesis (8) of nucleotides in the DNA encoding the peptide molecule thereby producing DNA encoding the variant, and thereafter expressing the DNA in recombinant cell culture. The variant typically exhibits the same qualitative biological activity as the nonvariant peptide.

An "analog" of GP88 protein refers to a non-natural molecule substantially similar to either the entire molecule or a fragment thereof.

The antibodies of the invention (neutralizing and others) are preferably used as a treatment for cancer or other diseases in cells which exhibit an increased expression of GP88. By the term "neutralizing" it shall be understood that the antibody has the ability to inhibit or block the normal biological activity of GP88, including, but not limited to, GP88's ability to stimulate cell proliferation, increase cell survival, block apoptosis, or to induce tumor growth in experimental animals and in humans. An effective amount of anti-GP88 antibody is administered to an animal, including humans, by various routes. In an alternative embodiment, the anti-GP88 antibody is used as a diagnostic to detect cells which exhibit an altered (increased) expression of GP88 as occurring in diseases such as but not limited to cancers, and to identify diseased cells whose growth is dependent on GP88 and which will respond to GP88 antagonizing therapy. In yet another embodiment, the anti-GP88 antibody is used to deliver compounds such as cytotoxic factors or antisense oligonucleotides to cells expressing or responsive to GP88.

It is to be understood that the application of the teachings of the present invention to a specific problem or environment will be within the capabilities of one having ordinary skill in the art in light of the teachings contained herein. The accompanying drawings, which are incorporated in and constitute a part of this specification, illustrate embodiments of the invention and, together with the description, serve to explain the principles of the invention. Examples of the products of the present invention and processes for their use appear in the following examples.

BRIEF DESCRIPTION OF THE DRAWINGS

FIG. 1B compares the level of GP88 mRNA expression in the 1246, 1246-3A and PC cell lines. mRNA for RPL32 is used as an internal control for equal amounts of RNA loading.

FIG. 1C compares the expression of GP88 mRNA in 1246 cells (left panel) and in PC cells (right panel) in serum-free and serum containing medium. The results show that GP88 expression in 1246 cells is inhibited by the addition of fetal bovine serum whereas such inhibition is not observed in the highly tumorigenic PC cells.

FIG. 3 shows C3H mice injected subcutaneously with $10^6$ antisense GP88 transfected PC cells (bottom) and with empty vector transfected control PC cells (top).

FIG. 5 shows GP88 mRNA expression levels in estrogen receptor positive and estrogen receptor negative human mammary carcinoma cell lines.

FIG. 8 shows the nucleotide and deduced amino-acid sequence of mouse GP88. (SEQ ID NOS 1 & 2 respectively) Peptide regions used as antigens to raise anti-GP88 antibodies K19T and S14R are underlined. The region cloned in the antisense orientation in the pCMV4 mammalian expression vector is indicated between brackets.

FIG. 9A shows the nucleotide sequence of human GP88 cDNA (SEQ ID NOS 16 & 17, respectively). Indicated between brackets is the region cloned in the antisense orientation into the pcDNA3 mammalian expression system; and FIG. 9B shows the deduced amino-acid sequence of human GP88. The E19V region used as antigen to develop anti-human GP88 neutralizing antibody is underlined. It also indicates the region A14R equivalent to the mouse S14R region.

FIG. 10 shows the amino-acid sequence of mouse GP88 (SEQ ID NO: 2) arranged to show the 7 and one-half repeats defined as granulins g, f, B, A, C, D and e (right side). This representation shows that the region K19T and S14R used to raise GP88 antibodies for developing anti-GP88 neutralizing antibodies is found between two epithlin/granulin repeats in what is considered a variant region. Indicated on the right hand side is the granulin classification of the repeats according to Bateman et al (6) Granulin B and granulin A are also defined as epithelin 2 and epithelin 1 respectively according to Plowman et al., 1992 (5).

FIG. 11 shows a schematic representation of pCMV4 and a GP88 cDNA clone indicating the restriction sites used to clone GP88 antisense cDNA into the expression vector.

FIG. 16 shows the effect of PCDGF on the proliferation of MCF-7 cells.

FIG. 17 shows the effect of inhibiting PCDGF expression on the E2 mitogenic effect.

FIG. 18 shows that overexpression of PCDGF in MCF-7 cells results in cells that are able to proliferate in the absence of E2 and are resistant to tamoxifen.

FIG. 19 shows the determination of PCDGF signaling pathway in MCF-7 cells.

FIG. 20 shows the effect of PCDGF on cyclin D1 and c-myc expression in MCF-7 cells.

FIG. 21 shows GP88 staining instensity with anti-GP88 antibody on paraffin embedded breast cancer biopsies by immunohistochemistry (IHC).

DETAILED DESCRIPTION OF THE INVENTION

Reference will now be made in detail to the presently preferred embodiments of the invention, which, together with the following examples, serve to explain the principles of the invention.

Biological Activity of GP88

The invention relates to GP88 and antitumor and antiviral compositions useful for treating and diagnosing diseases linked to altered (increased) expression of GP88. Alternatively this invention is used for treating and diagnosing diseases linked to increased responsiveness to GP88. Using a murine model system consisting of three cell lines, the inventor has shown that cells which overexpress GP88 form tumors. The parent cell line, 1246, is a C3H mouse adipogenic cell line which proliferates and differentiates into adipocytes in a defined medium under stringent regulation by insulin. The 1246 cells cannot form tumors in a syngeneic animal (C3H mouse) even when injected at a high cell density. An insulin independent cell line, 1246-3A, was isolated from 1246 cells maintained in insulin-free medium. The 1246-3A cells lost the ability to differentiate and form tumors when $10^6$ are injected subcutaneously in syngeneic mice. A highly tumorigenic cell line, PC, was developed from 1246-3A cells by an in vitro-in vivo shuttle technique. The PC cells formed tumors when $10^4$ cells were injected into syngeneic mice.

Figure 1A:
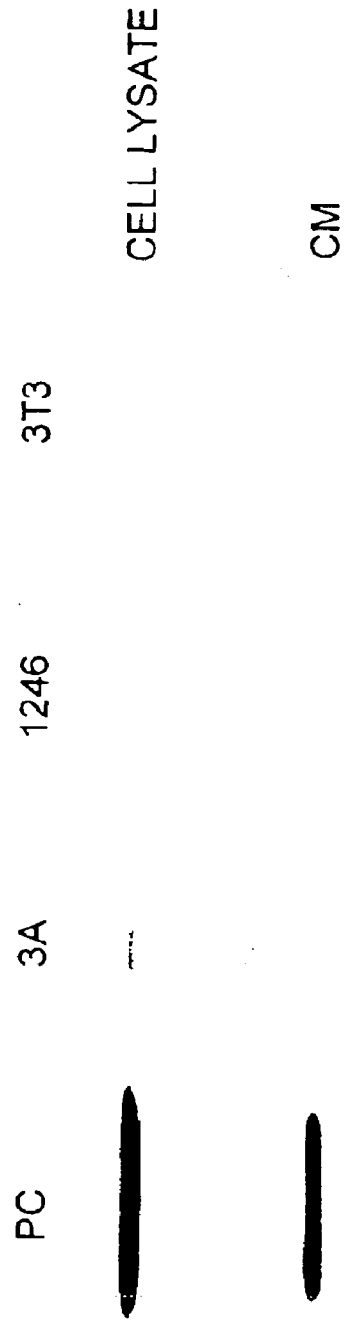
FIG. 1A compares the level of expression of GP88 protein in the 1246, 1246-3A and PC cell lines. Cells were cultured in DME-F12 medium supplemented with 2% fetal bovine serum (FBS). GP88 expression levels were measured by immunoprecipitation and Western blot analysis with anti-K19T antibody.

GP88 is overexpressed in the insulin-independent tumorigenic cell lines relative to the parent non-tumorigenic insulin-dependent cell line. Moreover, the degree of overexpression of GP88 positively correlates with the degree of tumorigenicity of these cells, demonstrating for the first time that GP88 is important in tumorigenesis (FIG. 1). With reference to FIG. 1, since GP88 is synthesized by cells but also secreted in culture medium, the level of GP88 was determined in cell lysates and in culture medium (CM). Al cells were cultivated in DME/F12 nutrient medium supplemented with 2% fetal bovine serum. When cells reached confluency, culture medium (CM) was collected and cell lysates were prepared by incubation in buffer containing detergent followed by a 10,000×g centrifugation. Cell lysate and conditioned medium were normalized by cell number.

Samples from cell lysate and conditioned medium were analyzed by Western blot analysis using an anti-GP88 antibody, as explained below.

Figure 2:
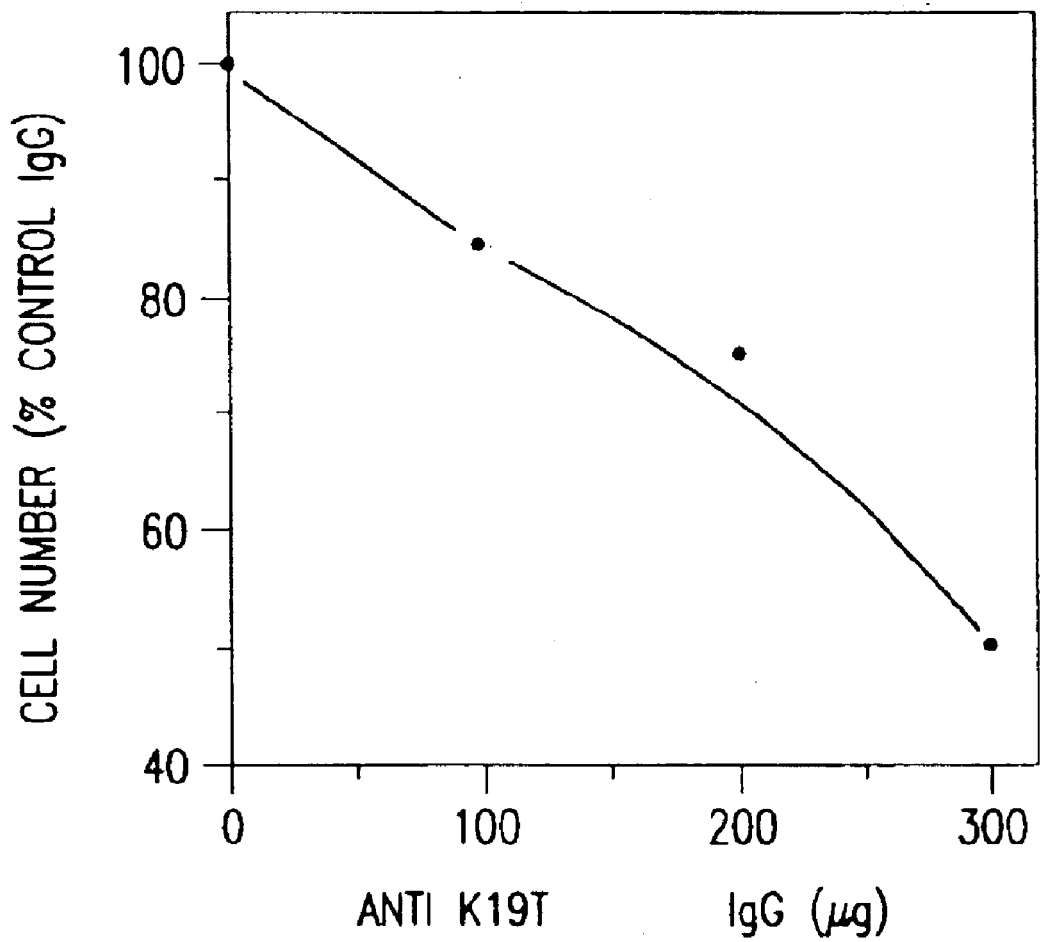
FIG. 2 illustrates the effect of treatment of the highly tumorigenic PC cells with increasing concentrations of anti-GP88 neutralizing antibody.

The development of a neutralizing antibody confirmed GP88's key role in tumorigenesis. When an anti-GP88 antibody directed to the K19T region of mouse GP88 was added to the culture medium, the growth of highly tumorigenic PC cells was inhibited in a dose dependent fashion (FIG. 2). With reference to FIG. 2, PC cells were cultivated in 96 well plates at a density $2 \times 10^4$ cells/well in DME/F12 medium supplemented with human fibronectin (2 μg/ml) and human transferrin (10 μg/ml). Increasing concentrations of anti-GP88 IgG fraction were added to the wells after the cells were attached. Control cells were treated with equivalent concentrations of non-immune IgG. Two days later, 0.25 mCi of $^3$H-thymidine was added per well for 6 hrs. Cells were then harvested to count $^3$H-thymidine incorporated into DNA as a measure for cell proliferation.

Moreover, when the expression of GP88 was specifically inhibited by antisense GP88 cDNA in PC cells, the production of GP88 was reduced and these PC cells could no longer form tumors in syngeneic C3H mouse. In addition, these PC cells regained responsiveness to insulin. With reference to FIG. 3 and Tables 1 and 2, C3H female mice were injected subcutaneously with $10^6$ antisense GP88 transfected PC cells (as explained below) or $10^6$ empty vector transfected PC cells. Mice were monitored daily for tumor appearance. Photographs were taken 45 days after injection of the cells. The results show that mice injected with antisense GP88 PC cells do not develop tumors, in contrast to the mice injected with empty vector transfected PC cells used as control.

TABLE 1

COMPARISON OF TUMORIGENIC PROPERTIES OF GP88 ANTISENSE TRANSFECTED CELLS, CONTROL TRKNSFECTED CELLS AND PC CELLS

| CELLS INJECTED | AVERAGE DAY OF TUMOR DETECTION | NUMBER OF MICE WITH TUMORS | AVERAGE TUMOR WEIGHT (g) |
| --- | --- | --- | --- |
| PC | 15 ± 3.0 | 5/5 | 9.0 ± 3.2 |
| P14 | 15 ± 3.7 | 5/5 | 7.8 ± 2.7 |
| ASGP88 | — | 0/5 | — |

PC: Control non-transfected cells
P-14: Empty vector control transfected PC cells
ASGP88: PC cells transfected with expression vector containing GP88 antisense cDNA Tumors were excised and weighed at 45 days. —indicates no tumor formation.

TABLE 2

COMPARISON OF PROPERTIES OF 1246, PC CELLS AND GP88 ANTISENSE CELLS

| 1246 cells | PC cells | Antisense GP 88 cells |
| --- | --- | --- |
| Insulin responsive for growth and differentiation | insulin-independent for growth differentiation deficient | Recovery of insulin responsiveness for growth (differentiation?) |
| | Autocrine production of insulin-related factor | |
| Cell surface insulin receptor expression high | cell surface insulin receptor expression very low | cell surface insulin receptor expression elevated |
| GP88 expression low | GP88 expression constitutively high | GP88 expression inhibited by antisense |
| GP88 expression inhibited by serum | No inhibition by serum | |
| GP88 expression regulated by insulin | GP88 expression constitutive | Recovery of insulin regulation for endogenous GP88 expression |
| Non-tumorigenic | highly tumorigenic | non-tumorigenic |

Figure 4:
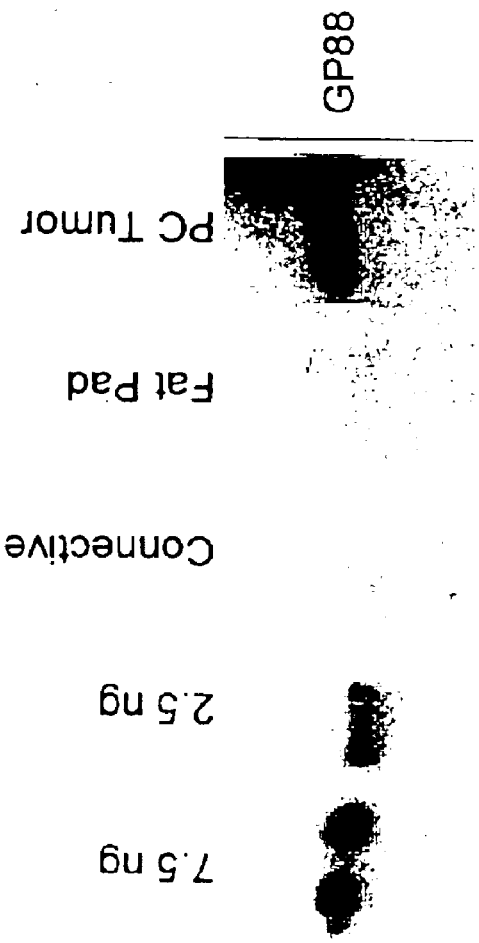
FIG. 4 shows in vivo GP88 expression levels in C3H mice tumor tissues and in surrounding normal tissues.

Comparison of the expression of GP88 indicates that in vivo GP88 levels in tumors is dramatically higher than in normal tissues (FIG. 4). C3H mice were injected with $10^6$ PC cells. Tumor bearing mice were euthanized. Tumors, fat pads and connective tissue were collected. Cell lysates were prepared by incubation in buffer containing detergent as described above for FIG. 1. Protein concentration of tissue extracts was determined, and equivalent amounts of proteins for each sample were analyzed by SDS-PAGE followed by Western blot analysis using anti-GP88 antibody to measure the content of GP88 in tissue extracts. The results showed that the level of GP88 in tumor extracts is at least 10-fold higher than in surrounding connective and fat tissues.

In normal cells (1246 cells, fibroblasts), the expression of GP88 is regulated, in particular by insulin, and inhibited by fetal bovine serum. In tumorigenic cells, a loss of regulation of normal growth leads to the increased expression of GP88 and the acquisition of GP88 dependence for growth. Therefore, inhibition of GP88 expression and/or action is an effective approach to suppression of tumorigenesis. Detection of an elevated GP88 expression in biopsies provides diagnostic analysis of tumors that are responsive to GP88 inhibition therapy.

Figure 6A:
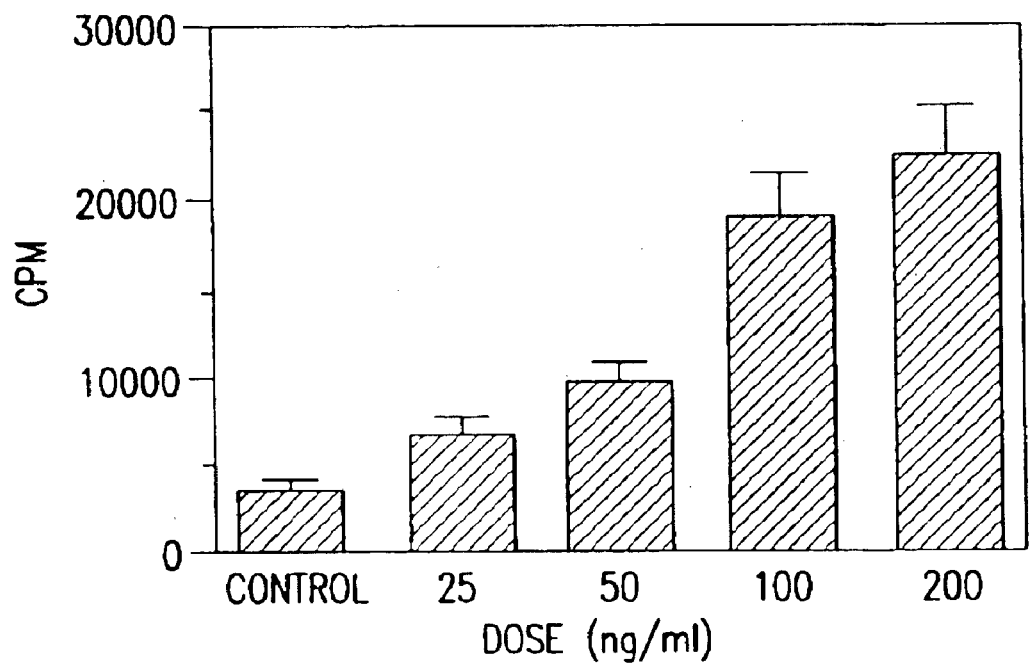
FIG. 6 shows the effect of increasing concentrations of GP88 on the growth of the mouse mammary epithelial cell line C57.
Figure 6B:
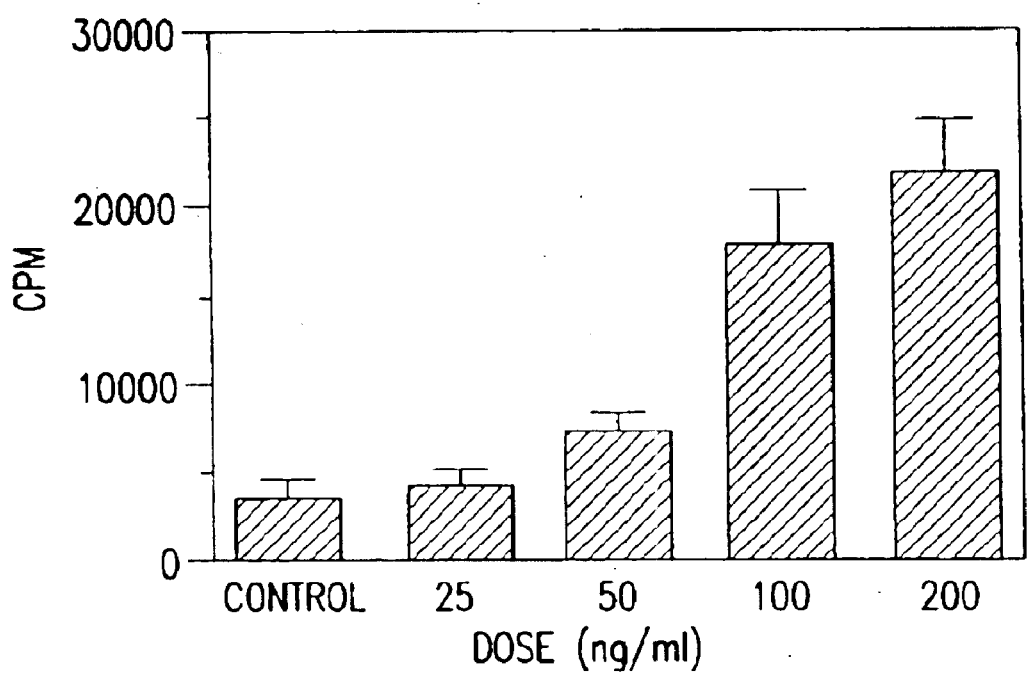
Figure 7:
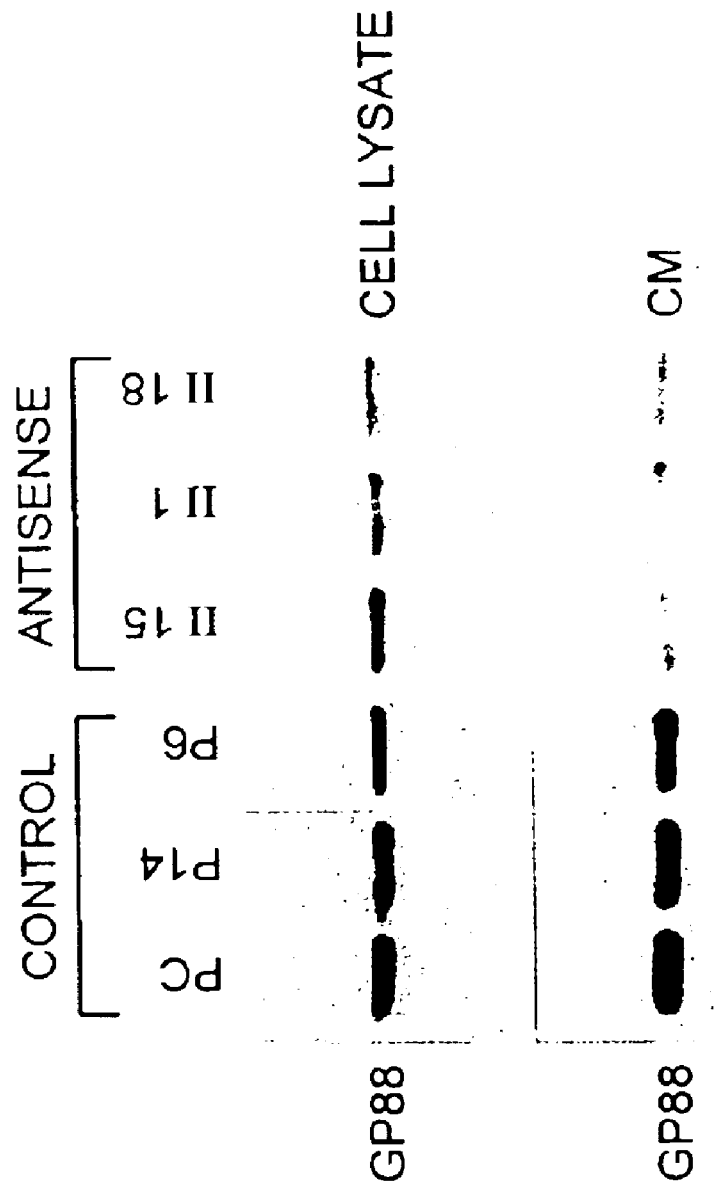
FIG. 7 shows the growth properties and tumorigenic ability of PC cells transfected with a cytomegalovirus promoter controlled expression vector containing GP88 in antisense orientation and PC cells transfected with an empty vector.
Figure 12:
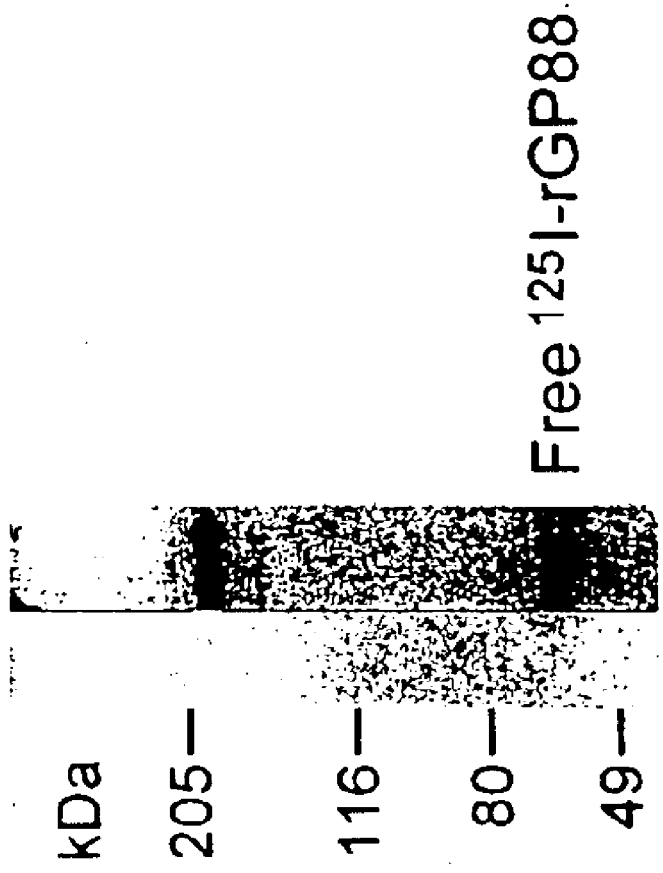
FIG. 12 shows the cross-linking of $^{125}$I-rGP88 to GP88 cell surface receptors on CCL-64 cells. The cross-linking reaction was carried out with disuccinimidyl suberate (DSS). Reaction products were analyzed by SDS-PAGE on a 7% polyacrylamide gel.
Figure 13:
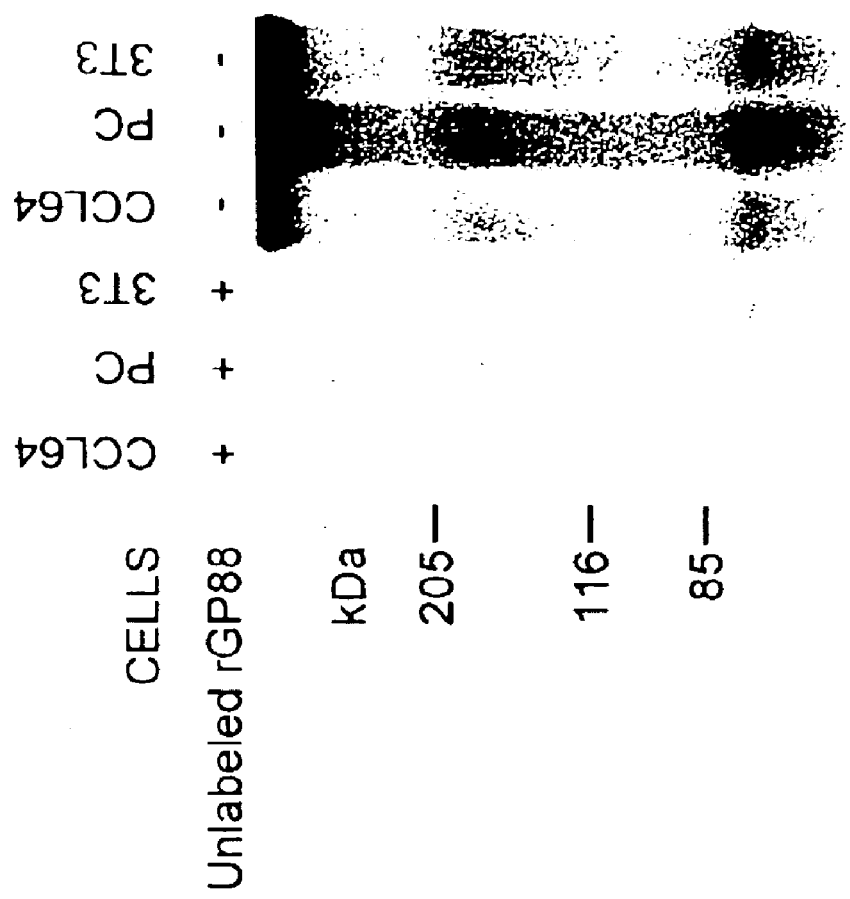
FIG. 13 shows the cross-linking of $^{125}$I-rGP88 to GP88 cell surface receptors on 3T3 fibroblasts, PC cells and C57MG mammary epithelial cells. The results show that these various cell lines display GP88 cell surface receptors of similar molecular weight as the ones on CCL64 cells (FIG. 12).
Figure 14:
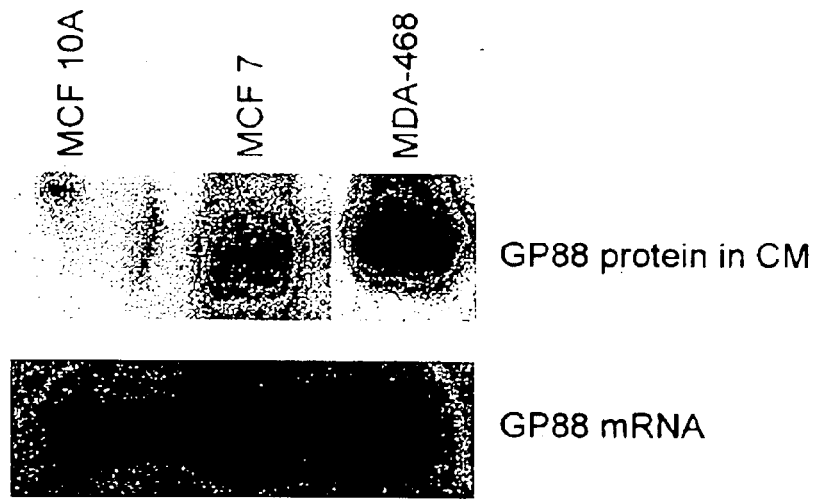
FIG. 14 shows GP88 expression levels in non-tumorigenic MCF 10A and in malignant (MCF 7, MDA-MB-468) human mammary epithelial cells.
Figure 15:
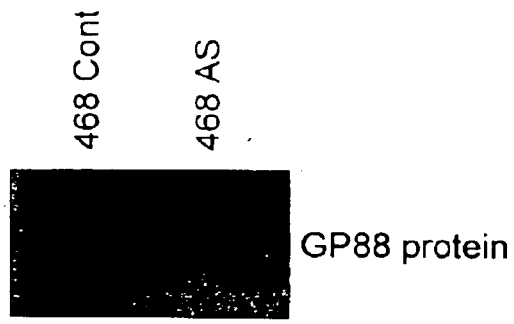
FIG. 15 shows that GP88 expression is inhibited by antisense GP88 cDNA transfection in human breast carcinoma, estrogen receptor negative MDA-MB-468 cells.

GP88 is also a tumor inducing factor in human cancers. As seen in the 1246-3A cell line, a loss of responsiveness to insulin (or to IGF-I) and a concurrent increase in malignancy has been well documented (13, 14) in several human cancers including but not limited to breast cancers. Specifically, breast carcinoma is accompanied by the acquisition of an insulin/IGF-I autocrine loop, which is also the starting point of the development of tumorigenic properties in the mouse model system discussed above. Furthermore, GP88 expression is elevated in human breast carcinomas. More specifically, with reference to FIG. 5, human GP88 was highly expressed in estrogen receptor positive and also in estrogen receptor negative insulin/IGF-I independent highly malignant cells. Also, GP88 is a potent growth factor for mammary epithelial cells (FIG. 6). The data in FIG. 5 was obtained by cultivating MCF7, MDA-MB-453 and MDA-MB-468 cells in DME/F12 medium supplemented with 10% fetal bovine serum (FBS). RNA was extracted from each cell line by the RNAzol method and poly-A$^+$ RNA prepared. GP88 mRNA expression was examined by Northern blot analysis with 3 μg of poly-A$^+$ RNA for each cell line using a $^{32}$P-labeled GP88 cDNA probe.

For Northern blot analysis of GP88 mRNA expression in rodent cells or tissues (mouse and rats), we used a mouse GP88 cDNA probe 311 bp in length starting at nucleotide 551 to 862 (corresponding to amino-acid sequence 160 to 270). RNA can be extracted by a variety of methods (Sambrook, Molecular Biology manual: 35) well known to people of ordinary skill in the art. The method of choice was to extract RNA using RNAzol (Cinnabiotech) or Trizol (Gibco-BRL) solutions which consists of a single step extraction by guanidinium isothiocyanate and phenol -chloroform.

For Northern blot analysis of GP88 mRNA expression in human cell lines, a 672 bp human GP88 cDNA probe was developed corresponding to nucleotide 1002 to 1674 (corresponding to amino-acid sequence 334–558) of human GP88.

With respect to FIG. 6, C57MG cells were cultivated in the presence of increasing concentrations of GP88 purified from PC cells conditioned medium (top panel), and recombinant GP88 expressed in insect cells (bottom panel), to demonstrate the growth stimulating effect of increasing concentrations of GP88 on the growth of the mouse mammary epithelial cell line C57MG.

A correlation between IGF-1 autocrine production and increased malignancy has also been well established for glioblastomas, teratocarcinomas and breast carcinomas. In these cancers, GP88 expression is also elevated in human tumors when compared to non-tumorigenic human fibroblasts and other human cell lines. GP88 promotes the growth of mammary carcinoma cells.

Anti-GP88 Antibodies

The invention provides compositions for treating and diagnosing diseases linked to increased expression of GP88. This also will apply to treatment and diagnosis of diseases linked to increased responsiveness to GP88. The compositions of this invention include anti-GP88 antibodies which neutralize the biological activity of GP88.

The present invention is also directed to an antibody specific for an epitope of GP88 and the use of such antibody to detect the presence or measure the quantity or concentration of GP88 molecule, a functional derivative thereof or a homologue from different animal species in a cell, a cell or tissue extract, culture medium or biological fluid. Moreover, antibody can be used to target cytotoxic molecules to a specific site.

For use as antigen for development of antibodies, the GP88 protein naturally produced or expressed in recombinant form or functional derivative thereof, preferably having at least 9 amino-acids, is obtained and used to immunize an animal for production of polyclonal or monoclonal antibody. An antibody is said to be capable of binding a molecule if it is capable of reacting with the molecule to thereby bind the molecule to the antibody. The specific reaction is meant to indicate that the antigen will react in a highly selective manner with its corresponding antibody and not with the multitude of other antibodies which may be evoked by other antigens.

The term antibody herein includes but is not limited to human and non-human polyclonal antibodies, human and non-human monoclonal antibodies (mAbs), chimeric antibodies, anti-idiotypic antibodies (anti-IdAb) and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by methods known to those skilled in the art (e.g., U.S. Pat. No. 4,376,110). Such antibodies may be of any immunological class including IgG, IgM, IgE, IgA, IgD and any subclass thereof. The hybridoma producing human and non-human antibodies to GP88 may be cultivated in vitro or in vivo. For production of a large amount of InAbs, in vivo is the presently preferred method of production. Briefly, cells from the individual hybridomas are injected intraperitoneally into pristane primed Balb/c mice or Nude mice to produce ascites fluid containing high concentrations of the desired mAbs. mAbs may be purified from such ascites fluids or from culture supernatants using standard chromatography methods well known to those of skill in the art.

Human monoclonal Ab to human GP88 can be prepared by immunizing transgenic mice expressing human immunoglobulin genes. Hybridoma produced by using lymphocytes from these transgenic animals will produce human immunoglobulin instead of mouse immunoglobulin.

Since most monoclonal antibodies are derived from murine source and other non-human sources, their clinical efficiency may be limited due to the immunogenicity of rodent mAbs administered to humans, weak recruitment of effector function and rapid clearance from serum. To circumvent these problems, the antigen-binding properties of murine antibodies can be conferred to human antibodies through a process called humanization. A humanized antibody contains the amino-acid sequences for the 6 complementarity-determining regions (CDRs) of the parent murine mAb which are grafted onto a human antibody framework. The low content of non-human sequences in humanized antibodies (around 5%) has proven effective in both reducing the immunogenicity and prolonging the serum half life in humans. Methods such as the ones using monovalent phage display and combinatorial library strategy for humanization of monoclonal antibodies are now widely applied to the humanization of a variety of antibodies and are known to people skilled in the art. These humanized antibodies and human antibodies developed with transgenic animals as described above are of great therapeutic use for several diseases including but not limited to cancer.

Hybridoma supernatants and sera are screened for the presence of antibody specific for GP88 by any number of immunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art will know how to prepare and screen such hybridomas without undue experimentation in order to obtain a desired polyclonal or mAb.

Chimeric antibodies have different portions derived from different animal species. For example, a chimeric antibody might have a variable region from a murine mAb and a human immunoglobulin constant region. Chimeric antibodies and methods for their production are also known to those skilled in the art.

An anti-idiotypic ("anti-IdAb") is an antibody which recognizes unique determinants generally associated with the antigen-binding site of an antibody. An anti-IdAb can be prepared by immunizing an animal of the same species and genetic type (e.g., mouse strain) as the source of the mAb with the mAb to which an anti-IdAb is being prepared. The immunized animal will recognize and respond to the idiotypic determinants of the immunizing antibody by producing antibody to these idiotypic determinants (the anti-IdAb). The anti-IdAb may also be used as an immunogen to produce an immune response in yet another animal, producing a so-called anti-anti-IdAb. The anti-anti-IdAb may be epitopically identical to the original m-Ab which induced the anti-IdAb. Thus by using antibodies to the idiotypic determinants of a mAb, it is possible to identify other clones expressing antibodies of identical specificity.

Accordingly, mAbs generated against GP88 may be used to induce human and non-human anti-IdAbs in suitable animals. Spleen cells from such immunized mice are used to produce hybridomas secreting human or non-human anti-Id mAbs. Further, the anti-Id mabs can be coupled to a carrier such as Keyhole Limpet Hemocyanin (KLH) or bovine serum albumin (BSA) and used to immunize additional mice. Sera from these mice will contain human or non-human anti-anti-IdAb that have the binding properties of the original mAb specific for a GP88 polypeptide epitope. The anti-Id mAbs thus have their own idiotypic epitopes or idiotypes structurally similar to the epitope being evaluated.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation and may have less non-specific tissue binding than an intact antibody. Such fragments are typically produced by proteolytic cleavage, using enzymes such as papain (to generate Fab fragments) and pepsin (to generate F(ab')2 fragments). It will be appreciated that Fab and F(ab')2 and other fragments of the antibodies useful in the present invention may be used for the detection or quantitation of GP88, and for treatment of pathological states related to GP88 expression, according to the methods disclosed herein for intact antibody molecules.

According to the present invention, antibodies that neutralize GP88 activity in vitro can be used to neutralize GP88 activity in vivo to treat diseases associated with increased GP88 expression or increased responsiveness to GP88, such as but not limited to cancer and viral infection. A subject, preferably a human subject, suffering from disease associated with increased GP88 expression is treated with an antibody to GP88. Such treatment may be performed in conjunction with other anti-cancer or anti-viral therapy. A typical regimen comprises administration of an effective amount of the antibody specific for GP88 administered over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or excipients known in the art. Pharmaceutical compositions such as tablets and capsules can also be prepared according to routine methods. It is understood that the dosage of will be dependent upon the age, sex and weight of the recipient, kind of concurrent treatment, if any, frequency of treatment and the nature of the effect desired. The ranges of effective doses provided below are not intended to limit the invention and merely represent preferred dose ranges. However the most preferred dosage will be tailored to the individual subject as is understood and determinable by one skilled in the art. The total dose required for each treatment may be administered by multiple doses or in a single dose. Effective amounts of antibody are from about 0.01 $\mu$g to about 100 mg/kg body weight and preferably from about 10 $\mu$g to about 50 mg/kg. Antibody may be administered alone or in conjunction with other therapeutics directed to the same disease.

According to the present invention and concerning the neutralizing antibody, GP88 neutralizing antibodies can be used in all therapeutic cases where it is necessary to inhibit GP88 biological activity, even though there may not necessarily be a change in GP88 expression, including cases where there is an overexpression of GP88 cell surface receptors and this in turn results in an increased biological activity, or where there is an alteration in GP88 signaling pathways or receptors leading to the fact that the signaling pathways are always "turned on." Neutralizing antibodies to growth factor and to growth factor receptors have been successfully used to inhibit the growth of cells whose proliferation is dependent on this growth factor. This has been the case for IGF-I receptor in human breast carcinoma cells and bombesin for lung cancer. The antibody to GP88 can also be used to deliver compounds such as, but not limited to, cytotoxic reagents such as toxins, oncotoxins, mitotoxins and immunotoxins, or antisense oligonucleotides, in order to specifically target them to cells expressing or responsive to GP88 (30).

One region that allows antigen to develop a neutralizing antibody to GP88 is the 19 amino-acid region defined as K19T in the mouse GP88, and E19V in the human GP88 which is not located within the epithelin/granulin 6 kDa repeats but between these repeats, specifically between granulin A (epithelin 1) and granulin C (5) in what is considered a variant region (see FIG. 10). Without wishing to be bound by theory, it is believed that the region important for the biological activity of GP88 lies outside of the epithelin repeats.

The antibodies or fragments of antibodies useful in the present invention may also be used to quantitatively or qualitatively detect the presence of cells which express the GP88 protein. This can be accomplished by immunofluorescence techniques employing a fluorescently labeled antibody (see below) with fluorescent microscopic, flow cytometric, or fluorometric detection. The reaction of antibodies and polypeptides of the present invention may be detected by immunoassay methods well known in the art.

The antibodies of the present invention may be employed histologically as in light microscopy, immunofluorescence or immunoelectron microscopy, for in situ detection of the GP88 protein in tissues samples or biopsies. In situ detection may be accomplished by removing a histological specimen from a patient and applying the appropriately labeled antibody of the present invention. The antibody (or fragment) is preferably provided by applying or overlaying the labeled antibody (or fragment) to the biological sample. Through the use of such a procedure, it is possible to determine not only the presence of the GP88 protein but also its distribution in the examined tissue. Using the present invention, those of ordinary skill in the art will readily perceive that any wide variety of histological methods (such as staining procedures) can be modified in order to achieve such in situ detection.

Assays for GP88 typically comprise incubating a biological sample such as a biological fluid, a tissue extract, freshly harvested or cultured cells or their culture medium in the presence of a detectably labeled antibody capable of identifying the GP88 protein and detecting the antibody by any of a number of techniques well known in the art.

The biological sample may be treated with a solid phase support or carrier such as nitrocellulose or other solid support capable of immobilizing cells or cell particles or soluble proteins. The support may then be washed followed by treatment with the detectably labeled anti-GP88 antibody. This is followed by wash of the support to remove unbound antibody. The amount of bound label on said support may then be detected by conventional means. By solid phase support is intended any support capable of binding antigen or antibodies such as but not limited to glass, polystyrene polypropylene, nylon, modified cellulose, or polyacrylamide.

The binding activity of a given lot of antibody to the GP88 protein may be determined according to well known methods. Those skilled in the art will be able to determine operative and optimal assay conditions for each determination by employing routine experimentation.

Detection of the GP88 protein or functional derivative thereof and of a specific antibody for the protein may be accomplished by a variety of immunoassays well known in the art such as enzyme linked immunoassays (ELISA) or radioimmunoassays (RIA). Such assays are well known in the art and one of skill will readily know how to carry out such assays using the anti-GP88 antibodies and GP88 protein of the present invention.

Such immunoassays are useful to detect and quantitate GP88 protein in serum or other biological fluid as well as in tissues, cells, cell extracts, or biopsies. In a preferred embodiment, the concentration of GP88 is measured in a tissue specimen as a means for diagnosing cancer or other disease associated with increased expression of GP88.

The presence of certain types of cancers and the degree of malignancy are said to be "proportional" to an increase in the level of the GP88 protein. The term "proportional" as used herein is not intended to be limited to a linear or constant relationship between the level of protein and the malignant properties of the cancer. The term "proportional" as used herein, is intended to indicate that an increased level of GP88 protein is related to appearance, recurrence or display of malignant properties of a cancer or other disease associated with increased expression of GP88 at ranges of concentration of the protein that can be readily determined by one skilled in the art.

Another embodiment of the invention relates to evaluating the efficacy of anti-cancer or anti-viral drug or agent by measuring the ability of the drug or agent to inhibit the expression or production of GP88. The antibodies of the present invention are useful in a method for evaluating anti-cancer or anti-viral drugs in that they can be employed to determine the amount of the GP88 protein in one of the above-mentioned immunoassays. Alternatively, the amount of the GP88 protein produced is measured by bioassay (cell proliferation assay ) as described herein. The bioassay and immunoassay can be used in combination for a more precise assessment.

An additional embodiment is directed to an assay for diagnosing cancers or other diseases associated with an increase in GP88 expression based on measuring in a tissue or biological fluid the amount of mRNA sequences present that encode GP88 or a functional derivative thereof, preferably using an RNA-DNA hybridization assay. The presence of certain cancers and the degree of malignancy is proportional to the amount of such mRNA present. For such assays the source of mRNA will be biopsies and surrounding tissues. The preferred technique for measuring the amount of mRNA is a hybridization assay using DNA of complementarity base sequence.

Another related embodiment is directed to an assay for diagnosing cancers or other diseases associated with an increase in GP88 responsiveness based on measuring on a tissue biopsy whether treatment with anti-GP88 neutralizing antibody will inhibit its growth or other biological activity.

Another related embodiment is a method for measuring the efficacy of anti-cancer or anti-viral drug or agent which comprises the steps of measuring the agent's effect on inhibiting the expression of mRNA for GP88. Similarly such method can be used to identify or evaluate the efficacy of GP88 antagonizing agents by measuring the ability of said agent to inhibit the production of GP88 mRNA.

Nucleic acid detection assays, especially hybridization assays, can be based on any characteristic of the nucleic acid molecule such as its size, sequence, or susceptibility to digestion by restriction endonucleases. The sensitivity of such assays can be increased by altering the manner in which detection is reported or signaled to the observer. A wide variety of labels have been extensively developed and used by those of ordinary skill in the art, including enzymatic, radioisotopic, fluorescent, chemical labels and modified bases.

One method for overcoming the sensitivity limitation of a nucleic acid for detection is to selectively amplify the nucleic acid prior to performing the assay. This method has been referred as the "polymerase chain reaction" or PCR (U.S. Pat. Nos. 4,683,202 and 4,582,788). The PCR reaction provides a method for selectively increasing the concentration of a particular nucleic acid sequence even when that sequence has not been previously purified and is present only in a single copy in a particular sample.

GP88 Antisense Components

This invention also provides GP88 antisense components. The constitutive expression of antisense RNA in cells has been shown to inhibit the expression of more than 20 genes and the list continues to grow. Possible mechanisms for antisense effects are the blockage of translation or prevention of splicing, both of which have been observed in vitro. Interference with splicing allows the use of intron sequences which should be less conserved and therefore result in greater specificity, inhibiting expression of a gene product of one species but not its homologue in another species.

The term antisense component corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. The action of the antisense RNA results in specific inhibition of gene expression in the cells.

According to the present invention, transfection of tumorigenic cells with DNA antisense to the GP88 cDNA inhibits endogenous GP88 expression and inhibits tumorigenicity of the antisense cDNA transfected cells. This antisense DNA must have sufficient complementarity, about 18–30 nucleotides in length, to the GP88 gene so that the antisense RNA can hybridize to the GP88 gene (or mRNA) and inhibit GP88 gene expression regardless of whether the action is at the level of splicing, transcription, or translation. The degree of inhibition is readily discernible to one skilled in the art without undue experimentation given the teachings herein and preferably is sufficient to inhibit the growth of cells whose proliferation is dependent on the expression of GP88. One of ordinary skill in the art will recognize that the antisense RNA approach is but a number of known mechanisms which can be employed to block specific gene expression.

The antisense components of the present invention may be hybridizable to any of several portions of the target GP88 cDNA, including the coding sequence, 3' or 5' untranslated regions, or other intronic sequences, or to GP88 mRNA. As is readily discernible by one of ordinary skill in the art, the minimal amount of homology required by the present invention is that sufficient to result in hybridization to the GP88 DNA or mRNA and in inhibition of transcription of the DNA, or translation or function of the mRNA, preferably without affecting the function of other mRNA molecules and the expression of other unrelated genes.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. Stable transfection of various antisense expression vectors containing GP88 cDNA fragments in the antisense orientation have been performed. One can also deliver antisense components to cells using a retroviral vector. Delivery can also be achieved by liposomes.

For purpose of antisense technology for in vivo therapy, the currently preferred method is to use antisense oligonucleotides, instead of performing stable transfection of an antisense cDNA fragment constructed into an expression vector. Antisense oligonucleotides having a size of 15–30 bases in length and with sequences hybridizable to any of several portions of the target GP88 cDNA, including the coding sequence, 3' or 5' untranslated regions, or other intronic sequences, or to GP88 mRNA, are preferred. Sequences for the antisense oligonucleotides to GP88 are preferably selected as being the ones that have the most potent antisense effects. Factors that govern a target site for the antisense oligonucleotide sequence are related to the length of the oligonucleotide, binding affinity, and accessibility of the target sequence. Sequences may be screened in vitro for potency of their antisense activity by measuring inhibition of GP88 protein translation and GP88 related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred GP88 antisense oligonucleotides are those oligonucleotides which are stable, have a high resilience to nucleases (enzymes that could potentially degrade oligonucleotides), possess suitable pharmacokinetics to allow them to traffic to disease tissue at non-toxic doses, and have the ability to cross through membranes.

Phosphorothioate antisense oligonucleotides may be used. Modifications of the phosphodiester linkage as well as of the heterocycle or the sugar may provide an increase in efficiency. With respect to modification of the phosphodiester linkage, phophorothioate may be used. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo. Cell culture and in vivo tumor experiments using these types of oligonucleotides targeted to c-raf-1 resulted in enhanced potency.

The delivery route will be the one that provides the best antisense effect as measured according to the criteria described above. In vitro cell culture assays and in vivo tumor growth assays using antisense oligonucleotides have shown that delivery mediated by cationic liposomes, by retroviral vectors and direct delivery are efficient. Another possible delivery mode is targeting using antibody to cell surface markers for the tumor cells. Antibody to GP88 or to its receptor may serve this purpose.

Recombinant GP88

The present invention is also directed to DNA expression systems for expressing a recombinant GP88 polypeptide or a functional derivative thereof substantially free of other mammalian DNA sequences. Such DNA may be double or single stranded. The DNA sequence should preferably have about 20 or more nucleotides to allow hybridization to another polynucleotide. In order to achieve higher specificity of hybridization, characterized by the absence of hybridization to sequences other than those encoding the GP88 protein or a homologue or functional derivative thereof, a length of at least 50 nucleotides is preferred.

The present invention is also directed to the above DNA molecules, expressible vehicles or vectors as well as hosts transfected or transformed with the vehicles and capable of expressing the polypeptide. Such hosts may be prokaryotic, preferably bacteria, or eukaryotic, preferably yeast or mammalian cells. A preferred vector system includes baculovirus expressed in insect cells. The DNA can be incorporated into host organisms by transformation, transduction, transfection, infection or related processes known in the art. In addition to DNA and mRNA sequences encoding the GP88 polypeptide, the invention also provides methods for expression of the nucleic acid sequence. Further, the genetic sequences and oligonucleotides allow identification and cloning of additional polypeptides having sequence homology to the polypeptide GP88 described here.

An expression vector is a vector which (due to the presence of appropriate transcriptional and/or translational control sequences) is capable of expressing a DNA (or cDNA) molecule which has been cloned into the vector and thereby produces a polypeptide or protein. Expression of the cloned sequence occurs when the expression vector is introduced into an appropriate host cell. If a prokaryotic expression vector is employed, then the appropriate host cell would be any prokaryotic cell capable of expressing the cloned sequence. Similarly, if an eukaryotic expression system is employed, then the appropriate host cell would be any eukaryotic cell capable of expressing the cloned sequence. Baculovirus vector, for example, can be used to clone GP88 cDNA and subsequently express the cDNA in insect cells.

A DNA sequence encoding GP88 polypeptide or its functional derivatives may be recombined with vector DNA in accordance with conventional techniques including blunt-ended or staggered ended termini for ligation, restriction enzyme digestion to provide appropriate termini, filling in cohesive ends as appropriate, alkaline phosphatase treatment to avoid undesirable joining, and ligation with proper enzyme ligases. Techniques for such manipulations are discussed in (35).

A nucleic acid molecule is capable of expressing a polypeptide if it contains nucleotide sequences which contain transcriptional and translational regulatory information and such sequences are operably linked to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism but shall in general include a promoter region, which in prokaryotes contains both the promoter (which directs the initiation of RNA transcription) as well as the DNA sequences which when transcribed into RNA will signal the initiation of protein synthesis. Such regions will normally include those 5' non-coding sequences involved with the initiation of transcription, translation such as the TATA box, capping sequence, CAAT sequence and the like.

If desired, the 3' non-coding region to the gene sequence encoding the protein may be obtained by described methods (screening appropriate cDNA library or PCR amplification). This region may be retained for the presence of transcriptional termination regulatory sequences such as termination and polyadenylation. Thus, by retaining the 3' region naturally contiguous to the DNA sequence coding for the protein, the transcriptional termination signals may be provided. Where the transcription termination signals are not provided or satisfactorily functional in the expression host cells, then a 3' region from another gene may be substituted.

Two DNA sequences such as a promoter region sequence and GP88 encoding sequence are said to be operably linked if the nature of the linkage between the sequences does not result in the introduction of a frame-shift mutation or interfere with the ability of the promoter sequence to direct transcription of the polypeptide gene sequence.

The promoter sequences may be prokaryotic, eukaryotic or viral. Suitable promoters are inducible, repressible or constitutive. Examples of suitable prokaryotic promoters are reviewed by.

Eukaryotic promoters include but are not limited to the promoter for the mouse methallothionein I gene, the TK promoter of Herpes Virus, the gene gal4 promoter, the SV40 early promoter, the mouse mammary tumor virus (MMTV) promoter, and the cytomegalovirus (CMV) promoter. Strong promoters are preferred. Examples of such promoters are those which recognize the T3, SP6 and T7 polymerases, the PL promoter of bacteriophage lambda, the recA promoter, the promoter of the mouse methallothionein I gene, the SV40 promoter and the CMV promoter.

Diagnostic Methods

The invention also provides GP88 diagnostic methods for determining tumorigenicity and also diagnostic methods for determining whether a patient is resistant to the antineoplastic effects of antiestrogen therapy. As described above, elevated levels of GP88 are indicative of increased tumorigenicity. In addition, the inventors have unexpectedly discovered that increased levels of GP88 are indicative of resistance to the antineoplastic effects of antiestrogens.

Antiestrogen therapy interferes or inhibits the function or synthesis of estrogen. For example, tamoxifen interferes with the binding of estrogen to its receptor. Aromatase inhibitors, such as anastrozole, interfere with enzymes that catalzye the conversion of androgens to estrogens thereby decreasing the levels of estrogen.

While not wishing to be bound by theory, we believe that elevated levels of GP88 contribute to the conversion of a cell from estrogen dependent to estrogen independent growth. Estrogen independent cells are insensitive to the presence or absence of estrogen and therefore are unaffected by antiestrogen therapy. Previously, the presence of the estrogen receptor was used as a much needed prognostic marker for resistance to antiestrogen therapy. However, as GP88 levels increase and the cell achieves estrogen independent growth, presence or absence of the estrogen receptor will no longer be sufficient to indicate whether the patient will be responsive to antiestrogen therapy. The level of GP88, and concomitantly and theoretically, estrogen independence, rather than the presence of the estrogen receptor, serves as an enhanced and more accurate, earlier and reliable prognostic marker for whether a patient will be resistant or responsive to antiestrogen therapy. As explained above, this new prognostic marker is particularly valuable given the well known propensity for antiestrogens such as tamoxifen to cause ovarian cancer in patients, particularly those that are, until the current invention, unknowingly resistant to the antineoplastic effects of antiestrogen therapy.

Preferred embodiments of the invention are directed to methods of determining whether a patient is resistant to the antineoplastic effects of antiestrogen therapy. GP88 protein or polynucleotide encoding GP88 is detected in biological sample(s) obtained from a patient, and the number of GP88 positive cells in the sample and the ratio of GP88 positive cells compared to the total number of cells are determined. The ratio of GP88 positive cells to the total number of cells is indicative of whether the patient is resistant to the antineoplastic effects of antiestrogen therapy. Alternatively, the amount of GP88 in a biological sample can be determined by detecting GP88 in a biological sample and extrapolating the amount of GP88 from a standard curve generated from detecting known amounts of GP88 protein or nucleic acid ("standard curve technique"). The standard curve technique is a preferred method for measuring the amount of GP88 in a biological sample not readily amenable to detecting GP88 in a discrete number of cells. For example, the amount of GP88 in a biological fluid (e.g., serum or cerebrospinal fluid) can be determined using the standard curve technique. The amount of GP88 in a biological sample is indicative of whether the patient is resistant to the antineoplastic effects of antiestrogen therapy.

Preferred biological samples include, but are not limited to, blood, cerebrospinal fluid, serum, plasma, urine, nipple aspirate, liver, kidney, breast, bone, bone marrow smears, testes, brain, ovary, skin, or lung. The biological sample may be of any size, shape or tissue type and include any number of cells and/or cell types. The biological sample can comprise non-tumorigenic cells and tumorigenic cells. Non-tumorigenic cells can include, without limitation, stromal or epithelial cells from normal tissue, peripheral tissue, benign lobular carcinoma, epithelial hyperplasia and any other benign lesion. The biological sample may comprise biological fluid containing cells or tissue.

As described above, GP88 protein can be detected by any suitable method, including immunostaining (e.g., immunohistochemical staining), western blot, chromatography, microarray, cell sorter using an anti-GP88 antibody. Preferably, the anti GP88 antibody is labeled (e.g., fluorescent dye, biotin, enzymatic, radioisotopic, fluorescent, and chemical labels) for use in a suitable detection system. Detection of GP88 protein or functional derivatives thereof may also be accomplished by a variety of diagnostic imaging techniques. The term "diagnostic imaging" refers to any technique for diagnosing a disease employing a labelled molecule for detection of a marker protein or nucleic acid in an imaging system (e.g., magnetic resonance imaging, ultrasound etc.). Antibody imaging using radiolabelled monoclonal antibodies is available for diagnosis of a variety of cancers (e.g., colon, prostate, lung, and ovarian cancer). Examples of diagnostic imaging systems include monoclonal antibody imaging systems such as the OncoScint® monoclonal antibody imaging system which is currently used to scan or image the body for diagnosis of cancer. Monoclonal antibodies may be employed in conventional scanning technologies such as MRI or ultrasound to specifically detect GP88 and determine the amount of GP88 or the number of GP88 positive cells in a biological sample.

GP88 nucleic acid can be detected with an antisense GP88 nucleic acid by any suitable detection assay (e.g., in situ hybridization, fluorescent in situ hybridization, Reverse Transcriptase-Polymerase Chain Reaction, Northern Blot, Southern blot, Southwestern blot, RNAse protection assay, microarray ) with anti-GP88 nucleic acid (e.g., GP88 cDNA probe). Preferably, the anti-GP88 nucleic acid is labeled using, for example, an enzymatic, radioisotopic, fluorescent, or chemical label.

GP88 positive cells can be counted by any suitable method known to those of skill in the art (e.g., microscopic examination, MRI, ultrasound, FACS analysis, luminex detection, antibody microarray, digital scanner, and cell sorter systems). For example, the number of GP88 positive cells in a biological sample can be determined by constructing a GP88 index in a manner similar to the Ki-67 index. Ki-67 is a DNA polymerase marker indicative of the proliferation rate of tissues. The number of Ki-67 positive cells is determined, and expressed as the percentage of Ki-67 positively staining cells per 1000 cells counted. Preferably, cells staining positive for GP88 are counted and expressed as the percentage of GP88 positively staining cells per 1000 cells counted. However, any number of cells can be counted. For example, counting more than 1000 cells may be preferred in order to obtain a more representative sample of cells from a patient. Counting fewer than 1000 cells may be preferred if the sample appears to be representative of various cell types and limited amount of sample is available for analysis.

For methods of determining whether a patient is resistant to the antineoplastic effects of antiestrogen therapy, the presence and intensity of GP88 staining in a biological sample is preferably graded as follows: less than about 5% GP88 positive cells is considered negative; about 10–25% GP88 positive cells is considered weakly positive (1+); about 25–50% GP88 positive cells (2+) is considered moderately positive; and more than about 50% GP88 positive cells is considered strongly positive (3+) for GP88. The percentage of GP88 positive cells for each grade may be readjusted depending on the size of the biological sample pool and/or the detection technique used to identify GP88 (e.g., immunostaining, in situ hybridization, fluorescent in situ hybridiation (FISH), reverse polymerase chain reaction, northern blot, western blot, southwestern blot, etc.). For example, the percentage of GP88 positive or stained cells for each grade may be adjusted downward when using a more sensitive technique for detecting GP88 or a larger biological sample pool. In accordance with a preferred embodiment of the invention, a percentage of GP88 positive or stained cells of at least about 5%, more preferably 10% and most preferably 25% is indicative of resistance to the antineoplastic effects of antiestrogen therapy. In another preferred embodiment, a percentage of at least about 10% GP88 positive or stained cells in estrogen receptor positive patients is indicative of resistance to the antineoplastic effects of antiestrogen therapy.

The invention also provides methods for diagnosing tumorigenicity comprising obtaining a biological sample from a patient, detecting GP88 protein or polynucleotide encoding GP88 in the biological sample, determining the number of GP88 positive or stained cells in the sample and the ratio of GP88 positive or stained cells compared to the total number of cells in a given sample. The ratio of GP88 positive or stained cells to the total number of cells is indicative of tumorigenicity. Detection of GP88 in biological samples is preferably carried out as described above with reference to methods of determining whether a patient is resistant to the antineoplastic effects of antiestrogen therapy.

In a preferred embodiment of the invention, a grading scale of GP88 staining intensity is constructed based on the percentage of GP88 positive cells according to standard intensity scale techniques known in the art. For methods of diagnosing tumorigenicity, the intensity of GP88 staining in a biological sample is preferably graded as follows: less than about 1% GP88 stained cells is considered negative or 0; about 1–5% GP88 stained cells is considered weakly positive for GP88 (1+); about 5–25% GP88 stained cells (2+) is considered moderately positive; and more than about 25% GP88 stained cells (3+) is considered strongly positive for GP88. The percentage of GP88 stained cells for each grade is readjusted depending on the size of the biological sample pool and the detection technique used to identify GP88 (e.g., immunostaining, in situ hybridization, fluorescent in situ hybridiation (FISH), reverse polymerase chain reaction, northern blot, western blot, southwestern blot, etc.). For example, the percentage of stained cells for each grade may be adjusted downward when using a more sensitive technique for detecting GP88 or when the biological sample pool is increased. In accordance with a preferred embodiment of the invention, a percentage of GP88 stained cells of at least about 1% is indicative of tumorigenicity.

The present invention is also directed to kits for diagnosing tumorigenicity or to determine whether a patient is resistant to the antineoplastic effects of antiestrogen therapy. The preferred kits of the invention comprise a container and a molecule for detecting GP88 (e.g., anti-GP88 antibody, GP88 cDNA probe, GP88 oligomer probe). Kits may also include reagents for immunostaining or in situ hybridization of biological samples. In a preferred embodiment, the kits of the invention include reagents for carrying out an enzyme-linked immunoassay ("ELISA") (e.g., anti-GP88 antibodies, conjugated and unconjugated recombinant GP88 for generated a standard curve, and a substrate for detection). Another preferred embodiment includes reagents for carrying out the reverse polymerase chain reaction method of detecting the presence of GP88 polynucleotides.

The invention also provides methods of treating or preventing cancer, such as breast cancer, comprising determining the amount of GP88 or the percentage of GP88 positive cells in a biological sample obtained from a patient, and administering tamoxifen in an amount sufficient to treat or prevent the breast cancer if the percentage of GP88 positive or stained cells in said breast tissue sample is less than about 5%. In another preferred embodiment of the invention, tamoxifen, or other antiestrogen therapy, is administered to an estrogen receptor positive patient if the percentage of GP88 positive or stained cells in the biological sample is less than about 10%. If the percentage of GP88 positive or stained cells is greater than 5%, anti-GP88 therapy (i.e., use of anti-GP88 antibodies or antisense GP88 polynucleotides) can be administered to restore sensitivity to antiestrogen therapy. The amount of antiestrogen sufficient to treat or prevent cancer is determined on a case-by-case basis. Guidance regarding administrating antiestrogen therapy (e.g., Nolvadex®, raloxifene, aromatase inhibitors, estrogen receptor downregulators etc.) to a patient is readily available and known to the treating physician.

It is to be understood that application of the teachings of the present invention to a specific problem or environment will be within the capability of one having ordinary skill in the art in light of the teachings contained herein. The present invention is more fully illustrated by the following non-limiting examples.

EXAMPLE 1

Mediation of Estrogen Mitogenic Effect in Human Breast Cancer MCF-7 Cells by PC-Cell Derived Growth Factor (GP88)

In estrogen-receptor positive cells, 17-β-estradiol (E2), an estrogen replacement compound, transcriptionally stimulated PCDGF expression in a dose and time-dependent fashion. We demonstrate here that PCDGF mediates the mitogenic effect of estradiol (E2) in MCF-7 cells. PCDGF substituted for E2 to stimulate DNA synthesis. The E2 mitogenic effect was inhibited in a dose-dependent fashion by anti-PCDGF neutralizing antibody. Inhibition of PCDGF expression in MCF-7 cells by antisense transfection also inhibited the E2 mitogenic effect. In contrast, overexpression of PCDGF in MCF-7 cells resulted in cells that were able to proliferate in the absence of estrogen and were tamoxifen resistant. Like E2, PCDGF stimulated mitogen activated protein kinase activity. PCDGF could substitute for E2 in stimulating cyclin D1 expression. The cyclin D1 stimulation by E2 was 50% inhibited by anti-PCDGF antibody. In contrast, PCDGF did not stimulate c-myc expression, another molecular target of E2. We conclude that autocrine PCDGF mediates the E2 mitogenic effect via stimulation of cyclin D1.

Screening of human tumor cell lines for PCDGF expression indicated that it was highly expressed in estrogen receptor negative (ER$^-$) human breast carcinomas. Inhibition of PCDGF expression in these cells by antisense PCDGF cDNA transfection resulted in a 90% inhibition of tumor incidence and tumor size when injected into nude mice. These data implicated PCDGF in the maintenance of the tumor phenotype. As indicated above, in ER+cells, PCDGF produced in response to estrogen receptor stimulation mediates E2 mitogenic activity. When PCDGF becomes overexpressed, then the cells become estrogen independent and resistant to the antineoplastic effects of antiestrogens.

Results

PCDGF Stimulates DNA Synthesis of MCF-7 Cells in the Absence of Estrogen

Figure 16B:
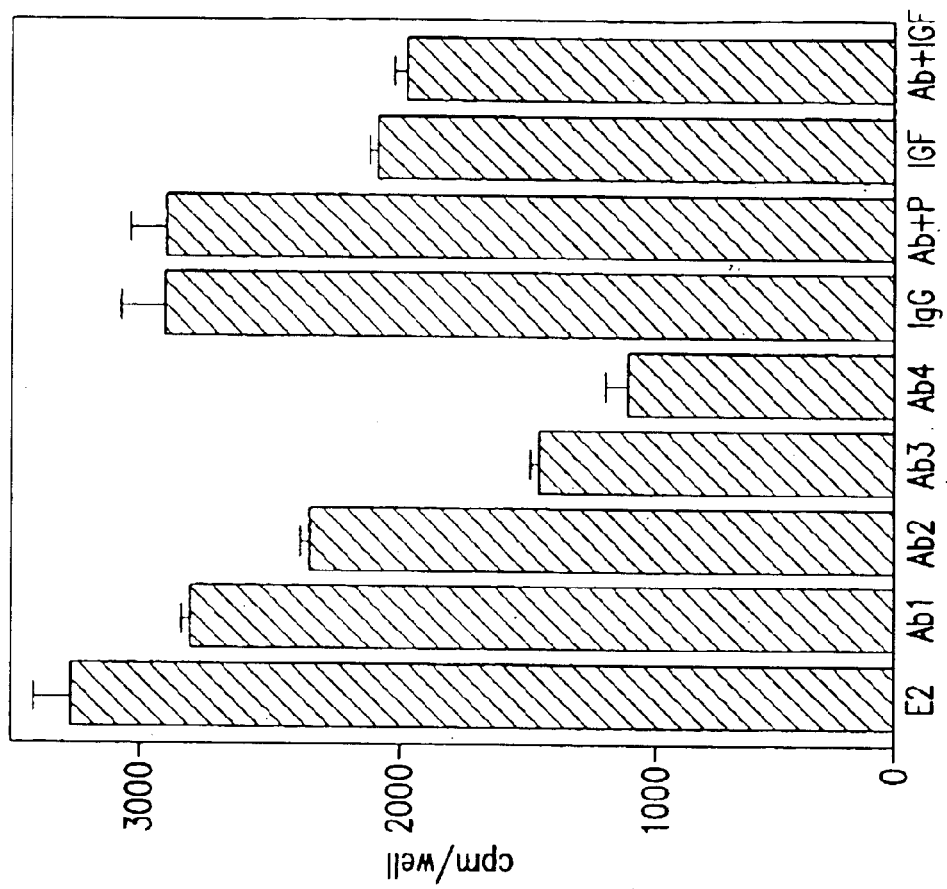
FIG. 16(B) illustrates that anti-PCDGF antibody specifically inhibits the E2 mitogenic effect. The results are expressed as means ±SD of triplicate determinations.
Figure 16A:
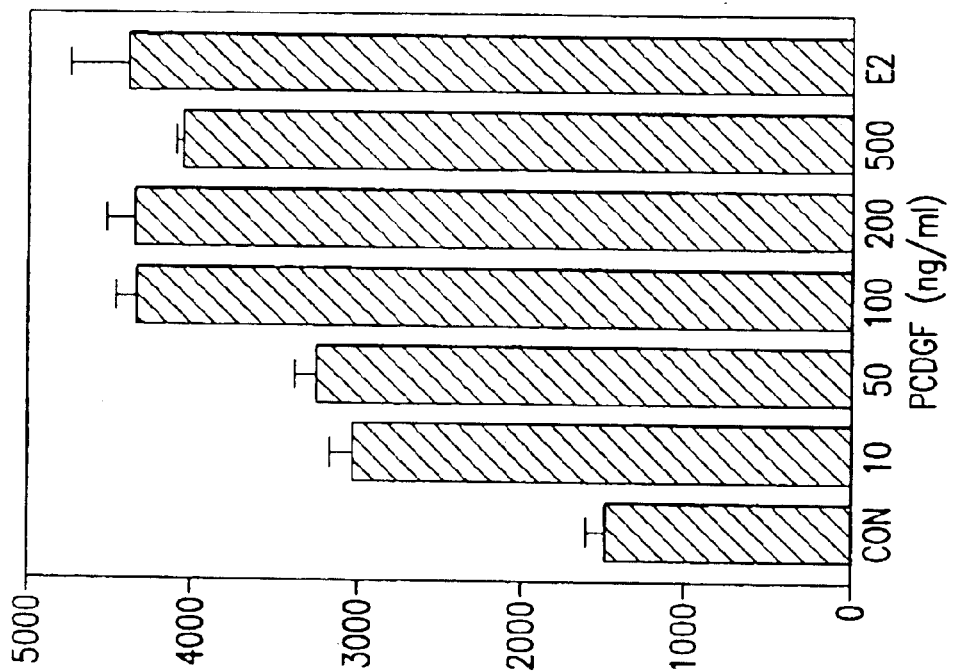
FIG. 16(A) illustrates that PCDGF stimulates DNA synthesis of MCF-7 cells in the absence of 17β-estradiol (E2).

We first examined whether addition of PCDGF stimulated DNA synthesis of MCF-7 cells maintained in the absence of E2. Under these conditions, endogenous production of PCDGF was very low. A 2-fold increase in $^3$H-thymidine incorporation over the control (cells maintained in the absence of E2 and PCDGF) ($P<0.01$) was observed at 10 ng/ml of PCDGF (FIG. 16A). FIG. 16A illustrates that PCDGF stimulates DNA synthesis of MCF-7 cells in the absence of E2. MCF-7 cells ($10^5$ cells per well) were plated in a 1:1 mixture of DMEM and Ham's F-12 medium plus 5% FBS. After 48 h, the medium was replaced with PFMEM, followed 24 hr later by serum-free α-MEM medium. Increasing concentrations of human PCDGF were added in triplicate to the medium. EtOH only (CON) or $10^{-9}$ M E2 (E2) were used as negative and positive controls, respectively. $^3$H-thymidine (1 µCi/ml) was added 24 h later for 5 h. The results are expressed as means ±SD of triplicate determinations. A 4-fold maximal stimulation was observed with 100 ng/ml PCDGF ($P<0.001$), similar to the one observed with $10^{-9}$ M E2. PCDGF stimulated DNA synthesis of another ER+cell line, T47D. A 2.9±0.3-fold stimulation of DNA synthesis was observed with 100 ng/ml PCDGF.

E2 mitogenic effect is inhibited by treatment of the cells with anti-PCDGF antibody. Based on these results and given that E2 stimulates PCDGF expression in MCF-7 cells, we determined whether endogenous PCDGF could mediate the E2 mitogenic effect via an autocrine loop. For this purpose, we first examined whether treatment with anti-PCDGF antibody that blocks PCDGF produced by the MCF-7 cells would inhibit the E2 mitogenic activity. The addition of affinity-purified anti-human PCDGF antibody inhibited in a dose-dependent fashion the growth of the cells stimulated by E2 (FIG. 16B). FIG. 16B illustrates that anti-PCDGF antibody specifically inhibits the E2 mitogenic effect. MCF-7 cells were treated with $10^{-9}$ M E2 (E2) alone or with increasing concentrations of affinity-purified anti-PCDGF antibody: 50 µg/ml (Ab1), 100 µg/ml (Ab2), 200 µg/ml (Ab3) and 300 µg/ml (Ab4). Cells treated with $10^{-9}$ M E2 and 300 µg/ml pre-immune IgG (preIgG) and cells treated with 10 ng/ml of IGF-II (IGF) alone or in the presence of 300 µg/ml anti-PCDGF antibody (Ab+IGF) were used as controls. The results are expressed in the figure as means ±SD of triplicate determinations. A 74% inhibition of E2 mitogenic effect was observed with 300 µg/ml of anti-PCDGF antibody ($P<0.003$), whereas a similar concentration of non-immune IgG had no effect. This antibody concentration displayed no cellular toxicity. Addition of PCDGF (200 ng/ml) restored the proliferation of the cells treated with anti-PCDGF antibody. The specificity of the PCDGF antibody effect was also demonstrated because it could not inhibit the stimulatory effect of insulin-like growth factor-II, a known growth stimulator of MCF-7 cells. These results show that PCDGF acts as an autocrine growth factor to mediate the mitogenic effect of E2 for MCF-7 cells.

Figure 17A:
FIG. 17(A) illustrates inhibition of PCDGF expression by antisense PCDGF cDNA transfection in MCF-7 cells.

Inhibition of PCDGF expression inhibits the growth of MCF-7 cells in the presence of E2. We next attempted to determine whether inhibiting PCDGF expression in MCF-7 cells would prevent the growth stimulatory effect of E2. For this purpose, we examined the E2 mitogenic effect in MCF-7 cells where PCDGF expression had been inhibited by antisense PCDGF cDNA transfection. The PCDGF levels in two representative antisense clones As13 and As22, and empty vector control transfected MCF-7 cells (MCF-7C) were determined by Western blot analysis of samples prepared by using identical cell numbers (FIG. 17A). FIG. 17A illustrates inhibition of PCDGF expression by antisense PCDGF cDNA transfection in MCF-7 cells. PCDGF expression in antisense (As13 and As22) and empty vector control transfected cells (MCF7-C) was examined by Western blot analysis. AS13 (lane 1), AS22 (lane 2) and MCF-7C cells (lane 3) were treated with $10^{-9}$ M E2 in PFMEM. The conditioned media were collected after 24h and normalized to the same cell number ($4\times10^6$ cells) for the measurement of PCDGF expression. As13 cells displayed an 80% inhibition of PCDGF expression, whereas As22 showed a 50% inhibition when compared with MCF-7C cells.

Figure 17B:
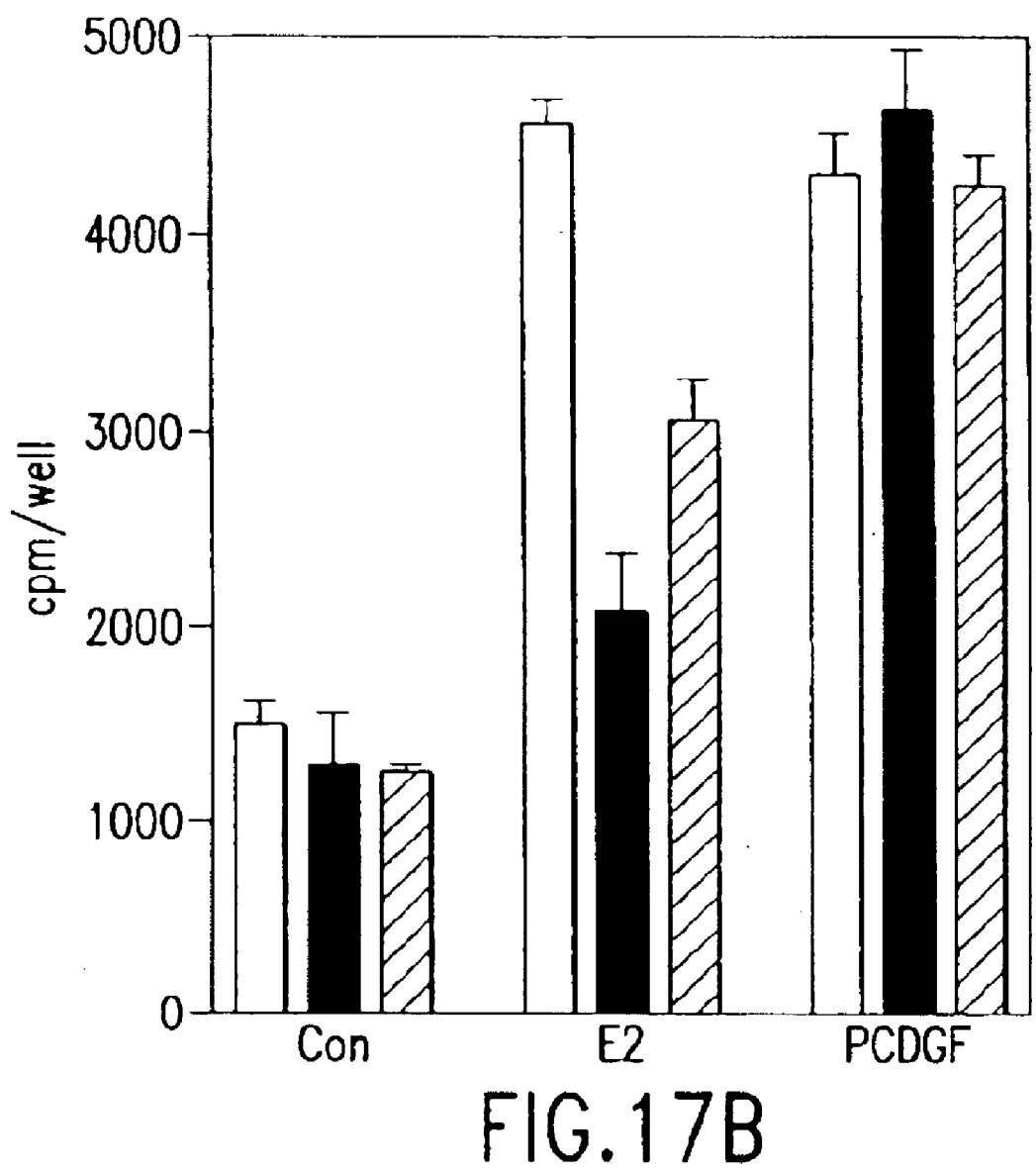
FIG. 17(B) illustrates that inhibition of PCDGF expression in MCF-7 cells inhibits the E2 mitogenic activity.

The effect of E2 on DNA synthesis then was examined in these antisense and control MCF-7C cells. A [-$^3$H] thymidine incorporation assay showed that the E2 stimulatory effect in MCF-7C cells had been reduced in AS13 and AS22 in correlation with the degree of inhibition of PCDGF expression (FIG. 17B). FIG. 17B illustrates that inhibition of PCDGF expression in MCF-7 cells inhibits the E2 mitogenic activity. E2 mitogenic effect was examined in antisense and control MCF-7C cells. AS13 (filled bars), AS22 (hatched bars), and MCF-7C cells (open bars) were treated with $10^{-9}$ M E2 (E2), 100 ng/ml recombinant PCDGF (PCDGF) or 0.1% EtOH only (Con). $^3$H-thymidine incorporation was measured as described above. Results are expressed in the figure as means ±SD. AS 13 showed the highest inhibition of the E2 effect. DNA synthesis mediated by E2 was only 25% ($P<0.001$) in AS13 and 60% ($P<0.001$) in AS22, respectively, of that observed in MCF-7C cells. The addition of PCDGF restored the proliferation of the antisense clones to the level found in the control MCF-7 cells cultivated in the presence of E2.

Overexpression of PCDGF Leads to Estrogen-Independence and Tamoxifen Resistance

Figure 18A:
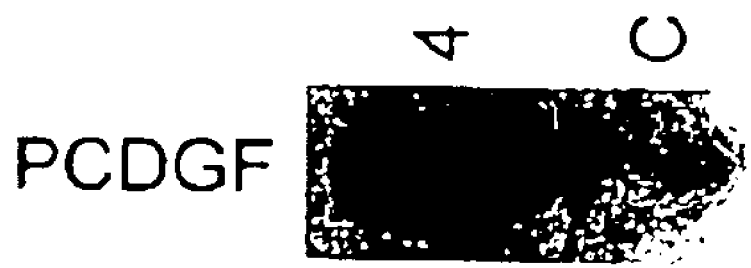
FIG. 18(A) shows PCDGF expression in O4 cells and control MCF-7C cells.

Based on the above results, we examined the effect of the constitutive overexpression of PCDGF in ER+MCF-7 cells on their estrogen and tamoxifen responsiveness. MCF-7 cells were transfected with a pcDNA3 expression vector containing PCDGF cDNA under the control of the cytomegalovirus promoter. Several PCDGF overexpressing clones were obtained including a representative clone termed O4. FIG. 18A shows that O4 cells produced elevated levels of PCDGF when compared with control MCF-7C cells in E2-depleted medium. FIG. 18A illustrates PCDGF expression in O4 cells and control MCF-7C cells. O4 and empty vector control MCF-7 cells were cultivated in PFMEM. The conditioned media were collected after 24 h to determine PCDGF expression.

Figure 18C:
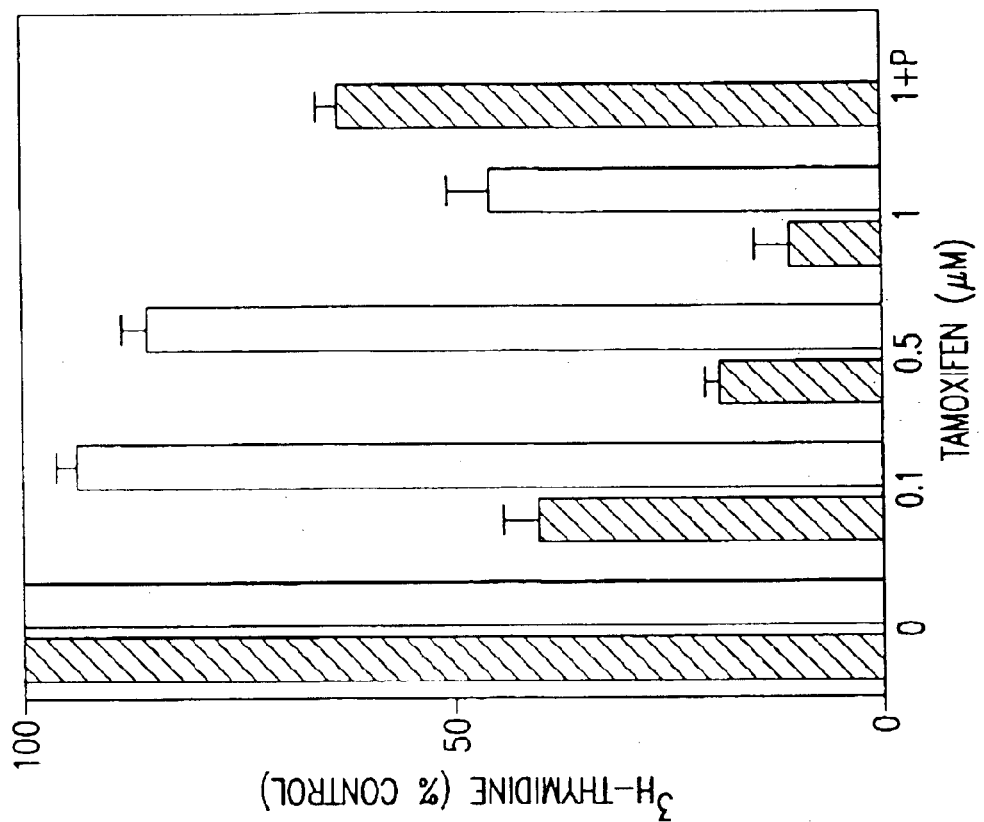
FIG. 18(C) shows a comparison of the response of MCF-7 and O4 cells to tamoxifen. The results are expressed as means ±SD.
Figure 18B:
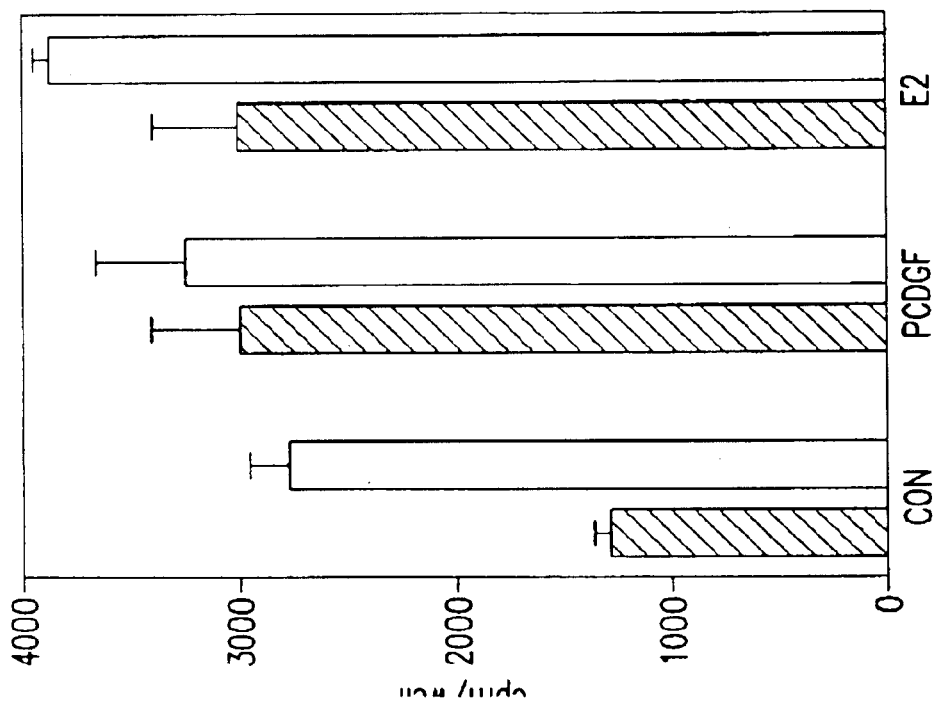
FIG. 18(B) shows proliferation of O4 and control MCF-7 cells in estrogen-depleted PFMEM medium.

Thymidine incorporation in O4 cells was 2.2-fold higher than in MCF-7C cells (P<0.01) demonstrating the ability of )4 cells to proliferate in the absence of E2 (FIG. 18B). FIG. 18B shows proliferation of O4 and control MCF-7 cells in estrogen-depleted PFMEM medium. Cells were plated in triplicate in estrogen-depleted PFMEM medium. Cells were either maintained in the absence of E2 (controls: Con) or were treated for 24 hours with either $10^{-9}$ M E2 or with 200 ng/ml PCDGF. $^3$H-thymidine was then added to measure DNA synthesis. The results are expressed as means ±SD. Moreover, there was no significant difference between the thymidine incorporation level for O4 cells in E2-depleted medium and for MCF-7C cells treated with either PCDGF or E2 (P>0.05). The addition of E2 or PCDGF to O4 cells did not have any significant additional effect in contrast to MCF-7C cells. In long-term growth assays, whereas MCF-7C cells could not grow in the absence of E2, O4 cells proliferated with a doubling time of 42 h, close to the 36 h doubling time of MCF-7C cells in the presence of E2. These data indicate that PCDGF overexpression provided a growth advantage in the absence of E2.

Based on these results, the tamoxifen-responsiveness of O4 and MCF-7C cells was examined. FIG. 18C shows a comparison of the response of MCF-7 and O4 cells to tamoxifen. MCF-7C cells (filled bars) and O4 cells (open bars) received $10^{-9}$ M E2 only or in the presence of increasing concentrations of tamoxifen. MCF-7C cells treated with 200 ng/ml of human PCDGF and 1 $\mu$M tamoxifen (T+P) were also examined. DNA synthesis was measured as described in FIG. 16. The results were expressed as the percentage of the DNA synthesis values in cells treated with E2 only. Tamoxifen inhibited the proliferation of MCF-7C cells in a dose-dependent fashion with a 60% inhibition of E2 effect at 100 nM, an 80% inhibition at 500 nM and a maximal 90% inhibition at 1 $\mu$M tamoxifen (FIG. 18C). In contrast, O4 cells displayed a markedly decreased responsiveness to tamoxifen, inasmuch as their proliferation was not affected by 100 nM tamoxifen, whereas only a 20% and a 55% inhibition of E2 effect was observed at 500 nM and 1 $\mu$M tamoxifen, respectively (P<0.001). Interestingly, the addition of PCDGF to MCF-7 cells reduced the tamoxifen inhibition from 90% to 38% (P<0.0001). These data show that PCDGF can overcome the tamoxifen inhibition and that increased PCDGF expression in MCF-7 cells leads to tamoxifen resistance.

The status of other parameters associated with estrogen responsiveness, such as estrogen receptor expression, activation of an estrogen response element by E2, and stimulation of progesterone receptor mRNA expression by E2, was assessed in all transfected cells. No difference was observed in these assays between antisense, control, and PCDGF overexpressing cells (data not shown). These data indicate that the changes in E2 proliferative response observed in the antisense or overexpressing cells were not due to an overall alteration in ER number or function but rather correlated with changes of PCDGF expression.

PCDGF Stimulates DNA Synthesis in MCF-7 Cells Via Activation of Mitogen Activating Protein Kinase ("MAP Kinase") Pathway We next examined the signal transduction pathways stimulated by PCDGF in MCF-7 cells, in comparison with E2. It has been shown that E2 stimulates progression through the G1 phase of the cell cycle. Some of the underlying molecular targets have now been elucidated. It is known that E2 stimulates MAP kinase activity in MCF-7 cells. Downstream, E2 activates the c-myc pathway and D-type cyclin/cdk complexes. Recent studies have postulated that the c-myc and cyclin D1 pathways were independently activated by E2 in breast cancer cells. Thus, we attempted to determine whether PCDGF could replace E2 to stimulate MAP kinase, cyclin D1 and/or c-myc pathways in MCF-7 cells.

Figure 19A:
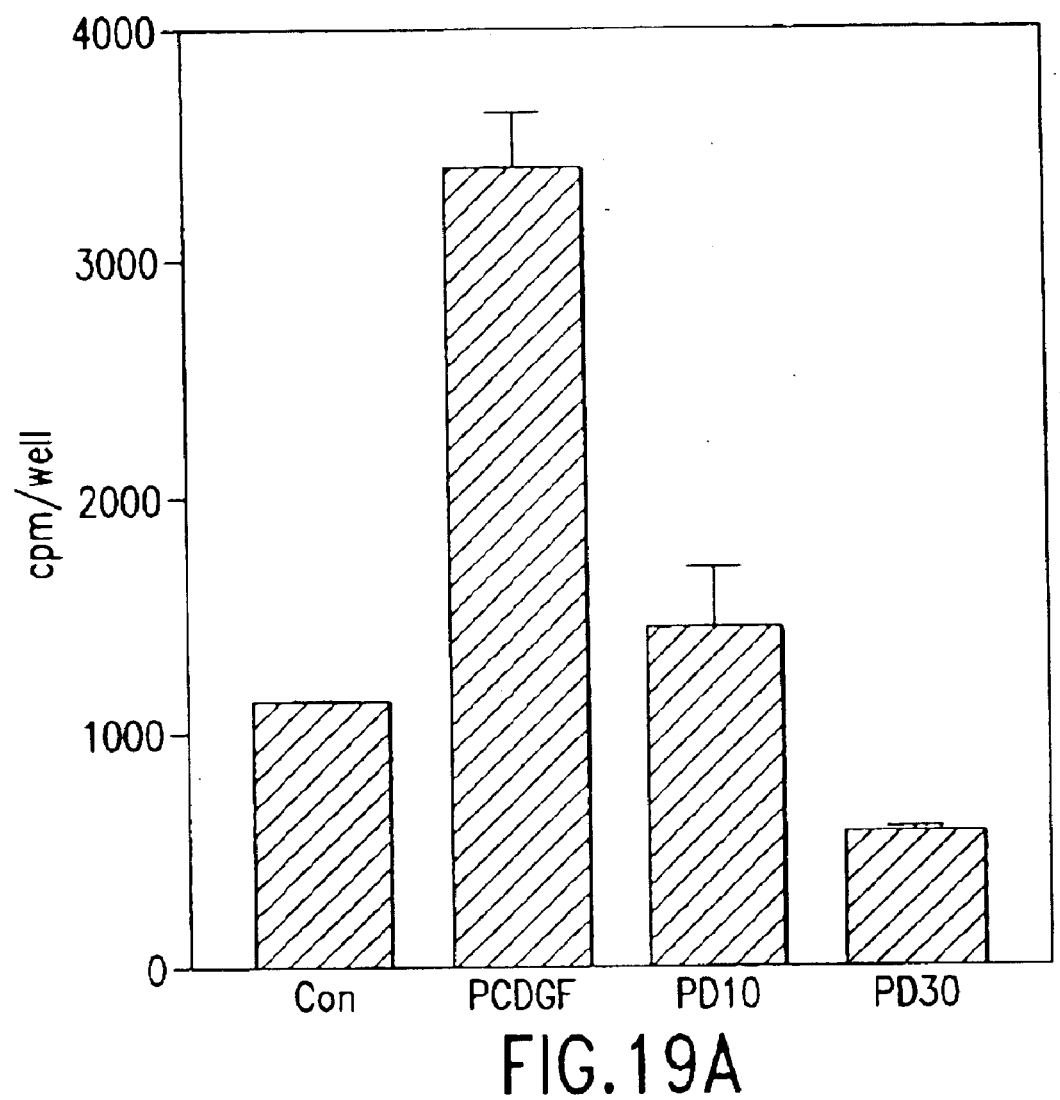
FIG. 19(A) illustrates the effect of MAP kinase inhibitor on the mitogenic effect of PCDGF.
Figure 19B:
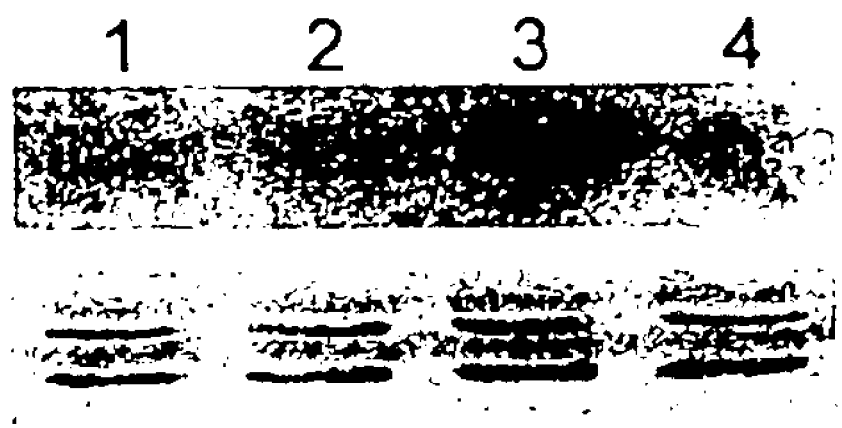
FIG. 19(B) illustrates activation of MAP kinase by PCDGF.

Two approaches showed the involvement of MAP kinase in mediating PCDGF action in MCF-7 cells. First, the stimulatory effect of PCDGF on DNA synthesis was inhibited in a dose-dependent fashion by the MEK inhibitor PD098059 (FIG. 19A). FIG. 19A shows the effect of MAP kinase inhibitor on the mitogenic effect of PCDGF. MCF-7 cells were cultivated as described in FIG. 16. Cells were pretreated for 60 min with 10 $\mu$M (PD10) or 30 $\mu$M (PD30) of PD098059 prior to addition of vehicle only (Con) or 100 ng/ml of recombinant human PCDGF alone (P). Thymidine incorporation data are presented as means ±SD. The PCDGF effect was almost completely abolished by 10 $\mu$M PD098059. Complete inhibition was observed with 30 $\mu$M PD098059, a concentration known to completely inhibit MAP kinase activity in other systems. Second, by using an in vitro MAP kinase assay, we showed that PCDGF (200 ng/ml) caused a three-fold increase in MAP kinase activity in MCF-7 cells (FIG. 19B). This effect was abolished by PD098059 (30 $\mu$M). FIG. 19B illustrates activation of MAP kinase by PCDGF. Cells were cultivated in PFMEM medium for 24 h followed by serum-free α-MEM medium. The samples examined were: MCF-7 cells treated for 10 minutes with 0, 50 ng/ml and 200 ng/ml of human PCDGF, (lanes 1–3, respectively); and MCF-7 cells treated for 10 minutes with 200 ng/ml of PCDGF and 30 $\mu$M PD098059 (lane 4). The kinase assay was conducted as described herein. The intensity of the phosphorylated MBP bands was analyzed by densitometric scanning. An equal amount of original supernatant was used to check the expression of MAP kinase (Erk1 and Erk2) as an internal control to normalize MAP kinase activity.

PCDGF Stimulates Cyclin D1 but not c-myc Expression in MCF-7 Cells

Figure 20A:
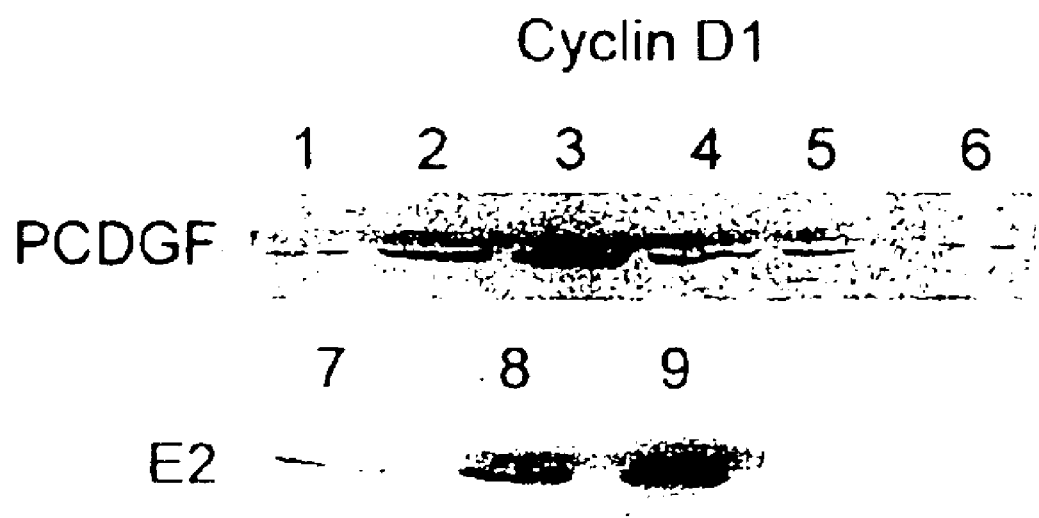
FIG. 20(A) shows stimulation of cyclin D1 expression by PCDGF.

Experiments were performed to determine the effect of PCDGF on cyclin D1 expression. PCDGF in a time-dependent fashion stimulated cyclin D1 expression in MCF-7 cells reaching a maximum of 4-fold over untreated controls after 5 h(FIG. 20A). The cyclin D1 stimulatory effect was abolished by PD98095 in an identical manner to its inhibition of the PCDGF mitogenic effect. FIG. 20A shows stimulation of cyclin D1 expression by PCDGF. MCF-7 cells were cultivated in triplicates in PFMEM medium and synchronized by treatment with 1 $\mu$M tamoxifen. Medium was replaced by fresh medium supplemented with 200 ng /ml PCDGF alone or with 30 $\mu$M PD98095 (upper) or with $10^{-9}$ M E2 (lower). Cells were lysed at the indicated times to determine cyclin D1 expression by Western blot analysis with 60 $\mu$g of whole cell lysates, using anti-cyclin D1 antibody. Samples were MCF-7 cells treated with 200 ng/ml PCDGF at 0 h (lane 1), 3 h(lane 2), 5 h (lane 3) and 12 h(lane 4); untreated MCF-7 cells at 5 hr (lane 5); MCF-7 cells treated with 200 ng/ml PCDGF and PD08950 at 5 hr (lane 6); and MCF-7 cells treated with $10^{-9}$ M E2 at time 0, 3 hr and 5 hr (lanes 7–9, respectively).

The stimulation of cyclin D1 expression by PCDGF was accompanied by the increase in the phosphorylation and expression of pRb, strictly required for G1 phase progression. After 6 hours of PCDGF treatment, pRb became hyperphosphorylated. After 24 hr, all of the pRb was in the hyper-phosphorylated form with a 5-fold increase in protein expression when compared to untreated cells. This effect was also blocked by PD98095 (data not shown).

Figure 20B:
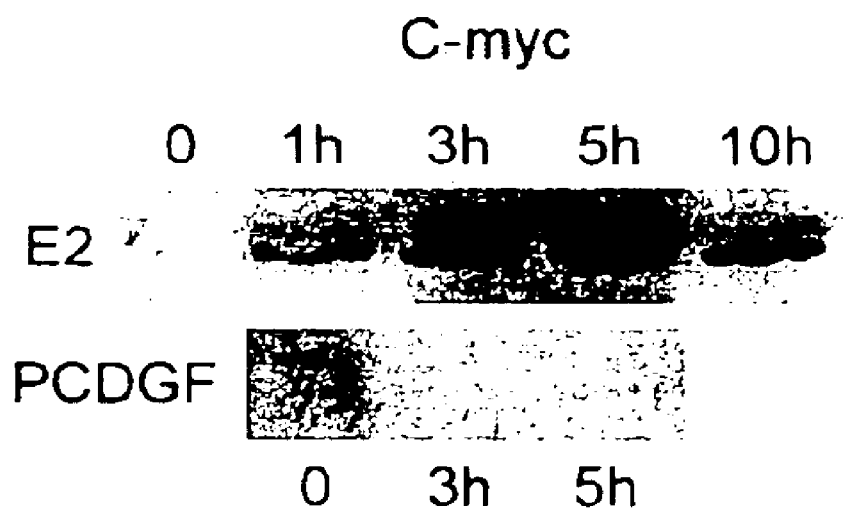
FIG. 20(B) shows the effect of E2 and PCDGF on c-myc expression.

We next compared the abilities of E2 and PCDGF to stimulate c-myc expression, another target for estrogen action in MCF-7 cells. As shown in FIG. 20B, E2 ($10^{-9}$ M) stimulated a rapid increase in c-myc expression in steroid-deprived MCF-7 cells with a maximal 4-fold induction within 3 hours. The level of c-myc induction by E2 was sustained for more than 10 hours. In contrast, PCDGF had no effect on c-myc protein expression during the same period of time (FIG. 20B). FIG. 20B illustrates the effect of E2 and PCDGF on c-myc expression. MCF-7 cells were synchronized by treatment with 1 $\mu$M tamoxifen. Cells were then treated with $10^{-9}$ M E2 (upper) or 200 ng/ml PCDGF (lower) for the indicated periods of time. Western blot detection of c-myc expression was performed by using 60 $\mu$g of whole cell lysates and anti-myc polyclonal antibody.

Because PCDGF induced cyclin D1 but not c-myc expression, we determined whether the increase of endogenous PCDGF was involved in the ability of E2 to stimulate cyclin D1 expression. The treatment of MCF-7 cells with anti-PCDGF neutralizing antibody (300 $\mu$g/ml) resulted in a 52±8% inhibition of the stimulation of cyclin D1 by E2, 5 hrs after addition of the antibody. This degree of inhibition was sustained 12 hours after antibody addition. These data show that the ability of E2 to stimulate cyclin D1 in MCF-7 cells is mediated, at least partially, by the endogenously produced PCDGF.

Discussion

We have reported previously that ER human mammary carcinoma cells express PCDGF and that E2 stimulates PCDGF expression in a dose and time-dependent fashion. We demonstrate herein that PCDGF mediates the growth stimulatory effect of E2. We show that PCDGF stimulates the proliferation of the human breast cancer cells MCF-7 and T47D maintained in the absence of E2. We next show that blocking the PCDGF autocrine pathway with anti-PCDGF antibody inhibits the mitogenic effect of E2. This effect was specific to PCDGF because the antibody was unable to inhibit the IGF-II mitogenic effect. The involvement of PCDGF in the mitogenic effect of E2 was further demonstrated by showing that the inhibition of PCDGF expression by antisense cDNA transfection reduced the E2 mitogenic effect on MCF-7 cells in correlation with the degree of inhibition of PCDGF expression. The addition of exogenous PCDGF restored the proliferation of these antisense cells. In addition, increased expression of PCDGF in MCF-7 cells led to cells able to proliferate in the absence of E2 and that were tamoxifen resistant. The fact that there was no change in other parameters of E2 responsiveness such as ER expression, activation of estrogen-response element-luciferase reporter gene, or stimulation of progesterone receptor expression indicated that alteration of E2 mitogenic effect in transfected cells was not due to a change in E2 receptors but specifically to a change in PCDGF expression.

Our results show that PCDGF upregulates cyclin D1 to mediate the mitogenic effect of E2 in human breast cancer cells. In support of this hypothesis, E2 inhibited the stimulation of cyclin D1 expression was inhibited by 52% within 5–12 hours following treatment of MCF-7 cells with anti-PCDGF neutralizing antibody. In conclusion, the studies described herein identify PCDGF as a novel mediator, at least in part, of the mitogenic effect of E2 on the human breast cancer cell line MCF-7.

EXAMPLE 2

Determination of Tamoxifen Resistance

We have shown that inhibiting the expression of GP88 by antisense cDNA transfection in ER negative breast cancer cells resulted in inhibition of tumorigenicity indicating the importance of GP88 overexpression in the tumorigenic properties of breast cancer cells. Because breast cancer is heterogeneous in nature and can affect various cellular functional compartments of the gland, it is preferable to examine biopsies representative of the various stages of the progression model for expression of GP88. It has been shown that detection of tumor markers is the preferred approach to evaluate and predict the clinical course of breast cancer at the time of diagnosis or primary treatment and is important in determining the choice of therapy. These studies are directly relevant to women's health because they provide an analysis of the novel growth factor PCDGF as a potential prognosis marker of breast cancer.

Expression of GP88 was followed by immunohistochemical analysis of sections from paraffin embedded biopsies using an affinity purified anti-human GP88 antibody. (FIG. 21). The progressive stages of the disease examined include benign hyperplasia→atypical ductal hyperplasia (ADH)→ (Ductal carcinoma in situ) DCIS→Invasive Ductal Carcinoma (IDC)→Metastatic Disease. Selected markers representative of genetic and biological alterations occurring during breast cancer progression were also examined in parallel.

For each stage of the disease examined (i.e.: benign stages including epithelial hyperplasia and fibrocystic changes, atypical ductal hyperplasia, ductal carcinoma in situ, invasive ductal carcinoma; and metastatic mammary carcinoma), GP88 expression was detected in parallel with detection of other markers such as Ki-67 (proliferation marker), p53 (tumor suppressor), ER/PR (responsiveness), cerbB2 expression (growth factor receptor), and correlated with grade, stage of disease and with lymph node status.

The biopsies were classified by histopathological determination of the stage and type of lesion and by examining several other prognostic markers such as Ki-67, and ER/PR status. Results indicated GP88 expression in the epithelial cells in ER-/PR ductal carcinoma grade 3 corresponding to tumors with poor prognosis. GP88 expression in the epithelial cells of normal tissue or benign lobular carcinoma were negative.

Methods

Preparation of tissues. 4 $\mu$m thick tissue sections were cut from paraffin blocks and mounted on electrically charged glass slides. Deparaffinization, fixation, antigen retrieval and rehydration of sections was done by standard procedures.

Preparation of anti-human GP88 antibody: A preferred method of detecting GP88 expression is by immunostaining using affinity purified anti-human PCDGF antibody. Polyclonal or monoclonal anti-human GP88 antibody was developed by immunizing rabbits or mice with human recombinant PCDGF expressed and purified in the inventor's laboratory. For polyclonal antibodies, anti-GP88 IgG fraction was prepared from rabbit antiserum by sodium sulfate precipitation and dialysis. This fraction was affinity purified by chromatography on GP88 conjugated Sepharose column prepared by coupling pure human GP88 to CNBr activated Sepharose. This highly purified antibody fraction was analyzed by SDS-PAGE chromatography and shown to contain a single band corresponding to the IgG and shown by immunostaining to provide a highly specific staining with no background on fixed cells and on tissue sections. Alternatively, anti-GP88 monoclonal antibodies may be employed.

Immunostaining was done by incubation of tissue sections prepared as described above for 1 hour at room temperature in moisture chambers with the specific antibody followed by incubation with anti-GP88 antibody. Antibody binding is preferably detected by incubation with biotinylated secondary antibodies and streptavidin peroxidase complex (Ventana kit). Chromogenic development is preferably obtained by the immersion of sections in 3,3'-diaminobenzidine solution (0.25 mg/mL with 3% hydrogen peroxide). The slides are then counterstained, preferably with hematoxylin, and coverslipped.

Analysis of the immunostaining data was done by microscopic examination. Scoring of selected markers was done using published methods as indicated below. Prior art staining intensity scoring methods include the following: ER and PR status and the presence of p53 mutated form are determined by grading the nuclear staining by universally used method (<5% of nuclei staining–negative; positive staining is assigned an intensity score from weak (1+) to moderate (2+) to strong (3+). c-erbB-2 staining is assessed by the presence and intensity of the membrane staining and is graded as follows: <5% staining–negative; positive staining graded from weak (1+) to moderate (2+) to strong (3+). Stromelysin-3 expression is graded separately in the tumor cells and the surrounding stroma and the scoring is preferably performed using the method used for ER/PR, p53 and c-erbB-2. The staining intensity grading methodologies are directly applicable to detection of GP88.

Our results show that in normal tissue and in benign lesion, the epithelial cells do not stain for GP88. In contrast, in ER–/PR: invasive ductal carcinoma, epithelial cells display a very strong positive staining for GP88. The presence of epithelial cells positive for GP88 can be scored and a grade can be assigned following the methods routinely used for scoring and indexing other prognosis markers of breast cancer. The following scoring and indexing scale was used to assess GP88 staining: less than about 5% staining is negative; about 10–25% positive staining is graded from weak (1+) to (moderate 25–50% positive cells (2+)) to strong (3+) (more than 50% positive cells). The percentage of positive cells for each grade is readjusted downward whenever an analysis of a large number of samples is obtained.

In addition to the method and type of biological samples described above, the detection of GP88 expression for predicting antiestrogen therapy response can be extended to measuring the increase of GP88 expression in biological fluids such as serum or plasma, urine or nipple aspirate. The detection of GP88 expression for predicting antiestrogen therapy response can also be readily extended to measuring the increase of GP88 expression in cell extracts.

The detection methods include, without limitation, enzyme linked immunoassay, such as an antibody directly conjugated to an enzyme (such as, without limitation, peroxidase, alkaline phosphatase, biotin) or to a fluorescent tag, or the use of a conjugated secondary antibody (such as, without limitation, peroxidase, alkaline phosphatase, strepavidin or a fluorescent tag).

Preferred methods for scoring of selected markers are well known in the art and described in the following references, the contents of which are hereby incorporated by reference into this application: (1) Ferno, M. (1998) Prognostic factors in breast cancer, *Anticancer Research*, 18, 2167–2172; (2) Harbeck N., Dettmar, P., Thomssen, C., Henlselmann, B., Kuhn, W., Ulm, K., Janicke, F., Hofler, H., Graeff, H., Schmitt, M. (1998), Prognostic impact of tumor biological factors on survival in node-negative breast cancer, *Anticancer Res.*18, 2187–2198; (3) Allred, D. C., Harvey, J. M., Berardo, M., Clark, G. M. (1998), Prognostic and predictive factors in breast cancer by immunohistochemical analysis, *Mod. Pathol.* 11,155–168; and (4) Thor, A. D., Moore, D. H., Edgerton, S. M., Kawasaki, E. S., Reihsaus, E., Lynch, H. T., Marcus, J. N., Scwartz, L., Chen, L. C., Mayall, B. H. (1992), Increased accumulation of the p53 suppressor gene product is an independent prognostic variable for breast cancer, *I. Natl. Cancer. Inst.*, 84, 845–855.

GP88 Staining with anti-GP88 Antibody

Paraffin embedded breast tissue biopsies from breast cancer patients were stained with anti-GP88 antibody using immunohistochemical techniques. As shown in FIG. 21, benign lesions exhibited no GP88 staining while invasive ductal carcinoma ("IDC") samples exhibited strong staining of GP88 positive cells. GP88 expression is elevated in tumorigenic ductal invasive carcinoma compared to benign lesions.

Figure 22:
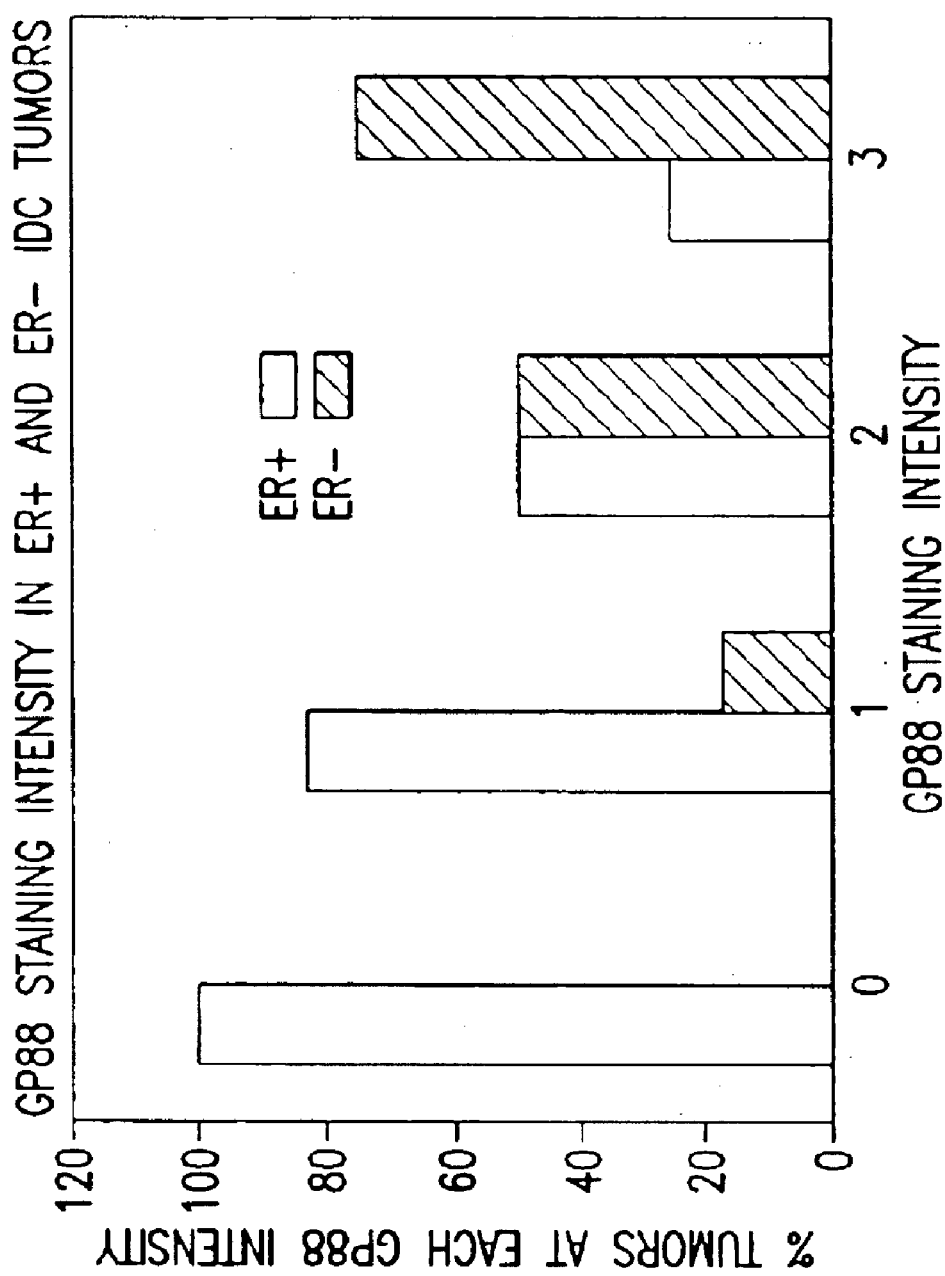
FIG. 22 shows the correlation between estrogen receptor status and GP88 staining intensity in Invasive Ductal Carcinoma (IHC) tumors.

GP88 Staining Intensity In Estrogen Receptor Positive (ER+) and Estrogen Receptor Negative (ER−) Invasive Ductal Carcinoma (IDC) Tumors Biological samples of IDC tumors were immunostained with anti-GP88 antibody and classified according their estrogen receptor status (ER+=estrogen receptor positive, ER−= estrogen receptor negative) and GP88 staining intensity grade. As shown in FIG. 22, an increase in GP88 staining intensity directly correlates with loss of estrogen receptor in IDC tumors. At a staining intensity of 0, all the IDC tumor samples analyzed were ER+. At a staining intensity of 1, 80% of the IDC tumors were ER+and 20% were ER−. At a staining intensity of 2, 50% of the IDC tumors were ER+and 50% were ER−. 20% of the IDC tumors were ER+at a staining intensity of 3 while 80% were ER−. Thus, as GP88 staining intensity increases, the percentage of ER+IDC tumors decreases.

Tamoxifen Responsiveness of ER+IDC Tumors Classified According To GP88 Staining Intensity An increase in GP88 staining intensity indicates a cell has lost dependance on estrogen for growth and has become estrogen independent. The growth of the cell is no longer controlled by external signals from hormones such as estrogen, but rather is controlled by autocrine growth signals from GP88. Previously, it was thought that the presence of the estrogen receptor was indicative of whether the cell was capable of responding to antiestrogen therapy. However, when a cell has converted from estrogen dependant to estrogen independent growth, the presence of the estrogen receptor is irrelevant to whether antiestrogen therapy will be effective since the cellular growth signal is constituitive and not controlled by the presence or absence of estrogens or antiestrogens. Thus, estrogen receptor positive tumors with high levels of GP88 (+2 or greater) are antiestrogen therapy resistant despite the fact the cells display the estrogen receptor.

Figure 23:
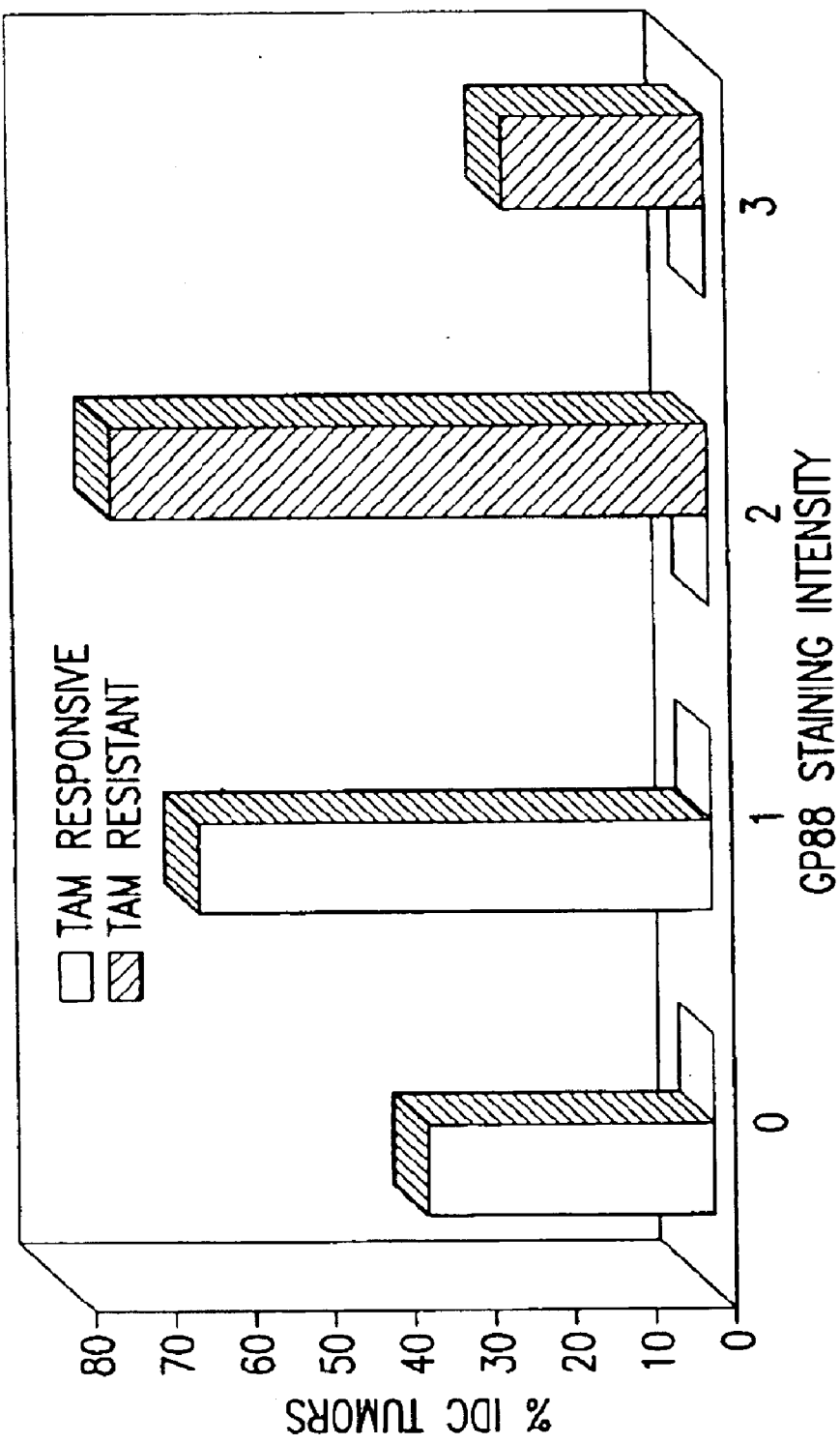
FIG. 23 shows the correlation between tamoxifen responsiveness of $ER_+$ IDC tumors and GP88 staining intensity. As GP88 staining intensity increases, estrogen receptor positive tumors become resistant to antiestrogen therapy.

In order to examine the effect of increased GP88 levels on antiestrogen resistance, IDC tumor samples were obtained from patients resistant to tamoxifen treatment and from patients responsive to tamoxifen treatment. The tumor samples were immunostained with anti-human GP88 antibody as described above. As shown in FIG. 23, IDC tumors were classified according to their GP88 staining intensity on a grading scale of 0 to 3 (x-axis). The percentage of total IDC tumors that were estrogen receptor positive (ER+) was determined and classified as either tamoxifen responsive (white bars) or tamoxifen resistant (black bars)along the y-axis. At a staining intensity grade of 0, all of the ER+IDC tumors (40% of the total number of tumors) were from tamoxifen responsive patients. At staining intensity grade of 1, all of the ER+IDC tumors (60% of the total number of tumors) were from tamoxifen responsive patients. However, as the staining intensity moved from grade 1 to grade 2, all of the ER+IDC tumors (80% of the total number of tumors) were from tamoxifen resistant patients. At a staining intensity grade of 3, all of the ER+tumors (30% of the total number of tumors) were from tamoxifen resistant patients. Thus, even ER+IDC tumors become increasingly resistant to the effects of tamoxifen increases as the GP88 intensity increases from grade 0 through grade 3. Furthermore, when the staining intensity increases from a grade 1 to 2, the ER+IDC tumors completely shifted from tamoxifen responsive to tamoxifen resistant. While not wishing to be bound by theory, it appears that the subsequent decrease in the percentage of tamoxifen resistant tumors from stage 3 to stage 4 is atributable to the loss of estrogen receptor (i.e., the percentage of ER+IDC tumors)as the level of GP88 increases. Therefore, FIG. 23 establishes that increasing levels of GP88 shift cells from an antiestrogen therapy responsive (grades 0 and 1) to antiestrogen therapy resistant (grades 2 and 3) stage even prior to the loss of the estrogen receptor. Thus, compared to the presence of the estrogen receptor, GP88 serves as a more accurate and reliable prognostic indicator of whether a patient will respond to, or be unduly harmed by, antiestrogen therapy.

The above description and accompanying drawings are only illustrative of exemplary embodiments, which can achieve the features and advantages of the present invention. It is not intended that the invention be limited to the embodiments shown and described in detail herein. The invention can be modified to incorporate any number of variations, alterations, substitutions or equivalent arrangements not heretofore described, but which are commensurate with the spirit and scope of the invention. The invention is only limited by the scope of the following claims.

What is claimed is:

1. A method for diagnosing tumorigenicity in a human patient, comprising:
   obtaining a breast tissue sample containing cells from said patient;
   detecting the protein encoded by SEQ ID NO. 16 in said cells of said breast tissue sample;
   determining the number of cells containing said protein in said sample; and
   determining the ratio of cells containing said protein to the total number of cells in said sample, wherein a ratio greater than about 5% is indicative of numorigenicity.

2. The method of claim 1, wherein said breast tissue sample comprises a material selected from the group consisting of blood, serum, and plasma.

3. The mechod of claim 1, wherein said patient has been diagnosed with cancer.

4. The method of claim 3, wherein said cancer is breast cancer.

5. The method of claim 1, wherein said protein is detected by immnunostaning with an anti-human GP88 antibody.

6. The method of claim 5, wherein said antibody is labeled.

7. The method of claim 6, wherein said label is selected from the group consisting of biotin, enzymatic, radioisotopic, fluorescent, and chemical labels.

8. The method of claim 1, wherein said number of cells is determined by microscopic examination.

9. The method of claim 1, wherein said number of cells is determined by a technique selected from group consisting of FACS analysis, luminex detection, antibody microarray digital scanner, and cell sorter.

10. The method of claim 1 wherein said ratio is at least about 10%.

11. The method of claim 1 wherein said ratio is at least about 25%.

12. The method of claim 1 wherein said ratio is at least about 50%.

13. A method of determining whether a human patient is resistant to the antineoplastic effects of antiestrogen therapy, comprising:
   obtaining a breast tissue sample containing cells from said patient; and
   detecting the presence of the protein encoded by SEQ ID NO. 16 in said sample wherein the presence of said protein in a ratio of greater than about 5% of the cells of the sample is indicative of resistance to the antineoplastic effects of antiestrogen therapy.

14. A method of determining whether a human patient is resistant to the antineoplastic effects of antiestrogen therapy, comprising:
   obtaining a breast tissue sample containing cells from said patient;
   detecting the protein encoded by SEQ ID NO. 16 in said cells of said breast tissue sample;
   determining the number of cells containing said protein in said sample; and
   determining the ratio of cells containing said protein to the total number of cells in said breast tissue sample wherein a ratio greater than about 5% is indicative of resistance to the antineoplastic effects of antiestrogen therapy.

15. The method of claim 13, wherein said sample comprises a material selected from the group consisting of blood, serum, and plasma.

16. The method of claim 13, wherein said patient has been diagnosed with cancer.

17. The method of claim 16, wherein said cancer is breast cancer.

18. The method of claim 13, wherein said protein is detected by immunostaining with an anti-human GP88 antibody.

19. The method of claim 18, wherein said antibody is labeled.

20. The method of claim 19, wherein said label is selected from the group consisting of biotin, enzymatic, radioisotopic, fluorescent, and chemical labels.

21. The method of claim 14, wherein said number of cells is determined by a technique selected from group consisting of FACS analysis, luminex detection, antibody microarray, digital scanner, and cell sorter.

22. The method of claim 14 wherein said ratio is at least about 10%.

23. The method of claim 22 wherein said patient is estrogen receptor positive.

24. The method of claim 22 wherein said ratio is at least about 25%.

25. The method of claim 24 wherein said patient is estrogen receptor positive.

26. The method of claim 24 wherein said ratio is at least about 50%.

27. The method of claim 26 wherein said patient is estrogen receptor positive.

28. The method of claim 13 wherein the ratio is at least about 10%.

29. The method of claim 28 wherein said patient is estrogen receptor positive.

30. The method of claim 13 wherein the ratio is at least about 25.

31. The method of claim 30 wherein said patient is estrogen receptor positive.

32. The method of claim 13 wherein the ratio is at least about 50%.

33. The method of claim 32 wherein said patient is estrogen receptor positive.

34. A method for diagnosing tumorigenicity, comprising:
    obtaining a breast tissue sample containing cells from a patient;
    detecting the protein encoded by SEQ ID NO. 16 in said cells of said breast tissue sample by immunostaining with anti-human GP88 antibody;
    determining the number of cells containing said protein in said sample by microscopic examination; and
    determining the ratio of cells containing said protein to the total number of cells in said breast tissue sample wherein a ratio of at least about 5% indicates tumorigenicity.

35. A method of determining whether an estrogen receptor positive patient is resistant to the antineoplastic effects of tamoxifen, comprising:
    obtaining a breast tissue sample containing cells from said patient;
    detecting GP88 in said cells of said breast tissue sample by immunohistochemical staining with anti-human GP88 antibody;
    determining the number of GP88 positive cells in said sample by microscopic examination; and
    determining the ratio of GP88 positive cells to the total number of cells in said biological sample wherein a ratio of at least about 10% indicates said patient is resistant to the antineoplastic effects of tamoxifen.

* * * * *